US011364286B2

(12) United States Patent
Morris et al.

(10) Patent No.: US 11,364,286 B2
(45) Date of Patent: Jun. 21, 2022

(54) COMPOSITIONS AND METHODS FOR THE TREATMENT OF DISEASES INVOLVING MUCIN

(71) Applicant: NewSouth Innovations Pty Limited, New South Wales (AU)

(72) Inventors: David L. Morris, Lugarno (AU); Roger Aston, Manly (AU); Javed Akhter, Prestons (AU); Krishna Pillai, The Ponds (AU)

(73) Assignee: NewSouth Innovations Pty Limited

( * ) Notice: Subject to any disclaimer, the term of this patent is extended or adjusted under 35 U.S.C. 154(b) by 0 days.

(21) Appl. No.: 15/768,091

(22) PCT Filed: Oct. 14, 2016

(86) PCT No.: PCT/AU2016/000351
§ 371 (c)(1),
(2) Date: Apr. 13, 2018

(87) PCT Pub. No.: WO2017/063023
PCT Pub. Date: Apr. 20, 2017

(65) Prior Publication Data
US 2018/0303916 A1    Oct. 25, 2018

(30) Foreign Application Priority Data

Oct. 14, 2015   (AT) .................................. 2015904201

(51) Int. Cl.
| | |
|---|---|
| *A61K 31/145* | (2006.01) |
| *A61K 31/513* | (2006.01) |
| *A61K 31/704* | (2006.01) |
| *A61K 31/7068* | (2006.01) |
| *A61K 33/243* | (2019.01) |
| *A61K 38/48* | (2006.01) |
| *A61K 45/06* | (2006.01) |
| *A61P 35/00* | (2006.01) |

(52) U.S. Cl.
CPC ........ *A61K 38/4873* (2013.01); *A61K 31/145* (2013.01); *A61K 31/513* (2013.01); *A61K 31/704* (2013.01); *A61K 31/7068* (2013.01); *A61K 33/243* (2019.01); *A61K 45/06* (2013.01); *A61P 35/00* (2018.01); *C12Y 304/22032* (2013.01); *C12Y 304/22033* (2013.01)

(58) Field of Classification Search
None
See application file for complete search history.

(56) References Cited

U.S. PATENT DOCUMENTS

| | | | |
|---|---|---|---|
| 3,002,891 A | 10/1961 | Heinicke | |
| 3,442,764 A | 5/1969 | Young et al. | |
| 3,455,787 A | 7/1969 | Makay | |
| 6,335,427 B1 | 1/2002 | Mynott et al. | |
| 8,197,808 B2 * | 6/2012 | Freeman | A61K 9/0014 424/94.65 |
| 2014/0314841 A1 | 10/2014 | Puri et al. | |

FOREIGN PATENT DOCUMENTS

| | | | |
|---|---|---|---|
| FR | 2826569 A1 | 1/2003 | |
| WO | 2013089803 A2 | 6/2013 | |
| WO | WO-2014036445 A2 * | 3/2014 | ............. A61K 31/66 |
| WO | 2014094041 A1 | 6/2014 | |

OTHER PUBLICATIONS

Fujisawa, T. et al. 2012.Cysteamine suppresses invasion, metastasis and prolongs survival by inhibiting matrix metalloproteinases in a mouse model of human pancreatic cancer. PLoS ONE 7(4): 1-10. specif, p. 1.*
Kufe, D.W. 2009. Mucins in cancer: function, prognosis and therapy. Nature Reviews Cancer 9: 874-885. specif, p. 874.*
European Search Report dated May 14, 2019 in European Patent Application No. 16854627.3.
Amini, A., et al., "Abstract LB-007: Synergistic inhibition of human gastric and colorectal cancers by Bromelain and N-acetylcysteine: An in vivo study," Proceedings of the 106th Annual Meeting of the American Association for Cancer Research; Apr. 18-22, 2015; Philadelphia, PA. Philadelphia (PA): AACR: Cancer Research, vol. 75(15Suppl), Abstract No. LB-007 (2015).
Piiiai, K., et al., "Anticancer Effect of Bromelain Alone and in Combination With Cisplatin or Fluorouracil on Malignant Peritoneal Mesothelioma Cells," European Journal of Cancer, vol. 50, Supplement 4, pp. e66, Abstract No. P0203 (2014).
Akhter, J., et al., "Efficacy of a novel mucolytic agent on pseudomyxoma peritonei mucin, with potential for treatment through peritoneal catheters," American Journal of Cancer Research, vol. 4(5), pp. 495-507 (2014).
Harrach, T., et al., "Isolation and Partial Characterization of Basic Proteinases from Stem Bromelain", Journal of Protein Chemistry, vol. 14(1), pp. 41-52 (1995).
Harrach, T., et al., "isolation and Characterization of Two Forms of an Acidic Bromelain Stem Proteinase," Journal of Protein Chemistry, vol. 17(4), pp. 351-361 (1998).
Taliarida, R. J., "The interaction index: a measure of drug synergism," Pain, vol. 98., pp. 163-168 (2002).
Devereux, G. et al., "Cysteamine as a Future Intervention in Cystic Fibrosis Against Current and Emerging Pathogens: A Patient-based ex vivo Study Confirming its Antimicrobial and Mucoactive Potential in Sputum", EBioMedicine, vol. 2, No. 10, pp. 1507-1512 (2015).

(Continued)

*Primary Examiner* — Olivia M. Wise
*Assistant Examiner* — Sharon M. Papciak
(74) *Attorney, Agent, or Firm* — Kim IP Law Group LLC

(57) ABSTRACT

The present invention relates to synergistic compositions comprising bromelain, or a proteolytic fraction thereof, and cysteamine or a metabolite, pharmaceutically acceptable salt, solvate or prodrug thereof The invention also relates to methods and uses of such compositions for the treatment of diseases involving mucin.

13 Claims, 28 Drawing Sheets

(56) References Cited

OTHER PUBLICATIONS

Pauzi, A.Z.M., et al., "Combination of cisplatin and bromelain exerts synergistic cytotoxic effects against breast cancer cell line MDA-MB-213 in vitro", Chinese Medicine, vol. 11, No. 46, pp. 1-11 (2016).
Amini, A., et al., "Potentiation of chemotherapeutics by bromelain and N-acetylcysteine: sequential and combination therapy of gastrointestinal cancer cells", American Journal of Cancer Research, vol. 6, No. 2, pp. 350-369 (2016).
Pillai, et al., "Assessment of a novel mucolytic solution for dissolving mucus in pseudomyxoma peritonei: an ex vivo and in vitro study", Pleura and Peritoneum, 2017, pp. 111-117, vol. 2, issue 2.
Pillai Krishna et al: "Mucolysis by Ascorbic Acid and Hydrogen Peroxide on Compact Mucin Secreated in Pseudomyxoma Peritonei". Journal of Surgical research, vol. 174, No. 2, May 1, 2012 (May 1, 2012), pp. e69-e73, XP055789935, US.
Q. Chen et al: "Pharmacologic doses of ascorbate act as a prooxidant and decrease growth of aggressive tumor xenografts in mice". Proceedings of the National Academy of Sciences, vol. 105, No. 32, Aug. 12, 2008 (Aug. 12, 2008), pp. 11105-11109, XP055457771, US.
Sarah J Davie, Barry J Gould and John S Yudkin: "Effect of Vitamin C on Glycosylation of Proteins", Diabetes, vol. 41, No. 2, Dec. 31, 1992 (Dec. 31, 1992), pp. 167-173, XP009526616.
European Examination Report for EP Application No. 16854627.3, dated Jan. 4, 2021.

\* cited by examiner

A

B

C

D

C

D

A

YOU cells treated with bromelain

B

YOU cell treated with cysteamine

C

PET cells treated with bromelain

D

PET cells treated with cysteamine

A
YOU cells treated with Cisplatin

IC50 = 0.18 ug/ml

B
PET cells treated with Cisplatin

IC50 = 0.21

C
YOU cells treated with a combination of bromelain and cysteamine

ICmax 92 % at 200 ug/ml Br for 0.706 mg/ml Cysteamine

D
PET cells treated with a combination of bromelain and cysteamine

ICmax 95 % at 200 ug/ml Br for 0.706 mg/ml Cysteamine

A

Treatment of YOU cells to 5.65 mg/ml Cysteamine with a combination of bromelain and cisplatin

B

PET cells treated to 5.65mg/ml Cysteamine and in combination with Cisplatin and Bromelain

A

YOUcells treated with 2.82 mg/ml Cysteamine and in combination with bromelain and Cisplatin

B

PET cells treated with 2.82 mg/ml Cysteamine and in combination with cisplatin and bromelain

A

PETcells treated with 1.42 mg/ml cysteamine and in combination with bromelain and cisplatin

B

YOU cells treated with 1.42 mg/ml Cysteine and in combination with bromelain and cisplatin

A

B

C

A

A2780 cells (72 h treatment with drugs)

SRB assay

B

A2780 cells (72 h treatment with drugs)

SRB assay

C

A2780 cells (72 h treatment with drugs)

SRB assay

A

B

C    Cytotoxic effect of Cisplatin on
pancreatic cancer cells(ASPC1) over 72 hours Cytotoxic effect of Cisplatin (CP) + cysteamine(CYS) on
pancreatic cancer cells (ASPC1) over 72 hours Pancreatic cancer cells (ASPC1) treated to a combination of bromelain and cysteamine (72 hours)

Cytotoxic effect of Cisplatin + Bromelain on pancreatic cancer cells (ASPC1) over 72 hours

A

Pancreatic cancer cells(ASPC1) treated to 0.6 mM cysteamine with various combinations of bromelain and cisplatin (72 hrs)

B

Pancreatic cancer cells(ASPC1) treated to 1.25 mM cysteamine and in combination with bromelain and cisplatin (72 hrs)

COMPOSITIONS AND METHODS FOR THE TREATMENT OF DISEASES INVOLVING MUCIN

RELATED APPLICATIONS

This application is a national stage entry, filed pursuant to 35 U.S.C. § 371, of PCT/AU2016/000351, filed Oct. 14, 2016, which claims the benefit of Australian Patent Application No. 2015904201, filed Oct. 14, 2015, which is incorporated herein by reference in its entirety.

FIELD

In general, the present invention relates to compositions for the treatment of diseases involving mucin, and specifically for the treatment of mucin-secreting cancers.

BACKGROUND

Mucins are a family of high molecular weight, heavily glycosylated proteins produced by epithelial tissues including the gastrointestinal tract, lungs, kidneys, ovaries, breast, and pancreas. Under normal physiological conditions, mucin plays a protective role for epithelial tissues. However, mucins can also be involved in disease states (such as cystic fibrosis) and the aberrant accumulation of mucinous material and failure to remove it can cause significant morbidity and mortality. For example, failure to expectorate mucus can lead to respiratory disease.

A high-level expression of mucin is associated with metastasis and poor clinical outcome in patients diagnosed with cancer. The synthesis of mucin on the surface of epithelial cells is normally highly regulated, but in tumors there is increased production of mucin partly due to an increased expression of human mucin (MUC1). Mucus expression and composition is altered in cancers of epithelial origin, and mucus production is known to be a negative prognostic factor. The secreted and transmembrane mucins that constitute the mucus barrier are considered to promote tumour progression.

Pseudomyxoma peritonei (PMP) is a form of cancer characterized by excessive accumulation of mucin, secreted by tumor cells, in the peritoneal cavity. The tumor cells are primarily of appendiceal origin although disseminated cancers of the colon, rectum, stomach, gall bladder, small intestines, urinary bladder, lungs, breast, pancreas and ovary may also contribute to the disease. The mucinous mass that is secreted accumulates in the abdominal cavity causes increased internal pressure on the digestive tract which is associated with significant morbidity and mortality due to nutritional compromise.

Traditionally, laparotomy, removal of mucinous mass and cytoreduction followed by hyperthermic intraperitoneal chemotherapy (HIPEC) has been the preferred treatment for PMP patients. Since the disease is progressive, patients may require several treatments during the course of the disease, which has the consequence of increased morbidity and even death. Additionally, it has been previously demonstrated that there is significant variability in the texture and hardness of PMP mucin.

Accordingly, there is a need for more effective compositions and methods for the disintegration and/or solubilisation of soft, semi-hard or hard mucinous material, in order to facilitate removal of the same from a subject in a manner which is more efficient and less invasive than currently used methods.

Similarly, in other instances where mucin and its accumulation deleteriously affects health such as glue ear, cystic fibrosis, sputum retention, chest infection, blockages in biliary/pancreatic stents, improved therapies for the removal of mucinous material are required.

Bromelain ("Br") is an extract of the pineapple plant (*Ananas Comosus*) comprises different thiol endopeptidases and other components such as phosphatases, glucosidases, peroxidises, cellulases, glycoproteins, carbohydrates and several protease inhibitors, and is known to have proteolytic activity in vitro and in vivo, and anti-edematous, anti-inflammatory, antithrombotic and fibrinolytic activities. The active factors in Br are biochemically characterized only in part. Nonetheless, due to its efficacy after oral administration, its safety and lack of undesired side effects, Br has good compliance among patients as a therapeutic drug.

The inventors have now surprisingly been found that compositions comprising bromelain, or a proteolytic fraction thereof and cysteamine display synergistic mucolytic and anti-cancer effects. Accordingly, the synergistic combination of bromelain and cysteamine provide one or more of enhanced disintegration and/or solubilization of mucinous material, increased efficacy in reducing the production of mucin, facilitation of the removal of mucinous material from the body, a direct inhibitory effect on tumor cell growth and increased efficacy of an anti-cancer agent.

SUMMARY OF INVENTION

The present invention thus relates at least to the following series of numbered embodiments below:

Embodiment 1

A synergistic mucolytic composition comprising bromelain, or a proteolytic fraction thereof, and cysteamine or a metabolite, pharmaceutically acceptable salt, solvate or prodrug thereof.

Embodiment 2

The composition according to embodiment 1, additionally comprising at least one further biologically active compound, or a metabolite, pharmaceutically acceptable salt, solvate or prodrug thereof.

Embodiment 3

The composition according to claim 2, wherein the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent.

Embodiment 4

The composition according to embodiment 3, wherein the biologically active compound is an anti-cancer agent.

Embodiment 5

The composition according to embodiment 4, wherein the anti-cancer agent is cisplatin.

Embodiment 6

A composition comprising bromelain, or a proteolytic fraction thereof, and cysteamine or a metabolite, pharmaceutically acceptable salt, solvate or prodrug thereof for use in the treatment of a disease involving mucin.

Embodiment 7

The composition according to embodiment 6, additionally comprising at least one further biologically active compound, or a metabolite, pharmaceutically acceptable salt, solvate or prodrug thereof.

Embodiment 8

The composition according to embodiment 7, wherein the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent.

9

The composition according to embodiment 8, wherein the biologically active compound is an anti-cancer agent.

10

The composition according to embodiment 9, wherein the anti-cancer agent is cisplatin.

11

The composition according to any one of embodiments 6-10, wherein the disease is cancer or pseudomyxoma peritonei.

12

The composition according to embodiment 11, wherein the cancer is selected from lung cancer, breast cancer, colorectal cancer, thyroid cancer, prostate cancer, stomach cancer, pancreatic cancer, cancer of the appendix and ovarian cancer.

13

The composition according to embodiment 11, wherein the cancer is signet ring cell carcinoma.

14

The composition according to any one of embodiments 6-13, wherein the mucin is characterized as having a semi-hard or hard consistency.

15

The composition according to any one of embodiments 6-14, wherein the treatment comprises a step of removing mucinous material from a subject after a period of time following the administration of said composition.

16

The composition according to embodiment 15, wherein the period of time is selected from of about 5, 10, 15, 20, 30, 40, 50, or 60 minutes.

17

The composition according to embodiment 15, wherein the period of time is selected from of about 1 hour, 1.5, 2, 2.5, 3, 3.5 or 4 hours.

18

Use of a composition comprising bromelain, or a proteolytic fraction thereof, and cysteamine, or a metabolite, pharmaceutically acceptable salt, solvate or prodrug thereof, in the manufacture of a medicament for the treatment of a disease involving mucin.

Embodiment 19

The use according to embodiment 18, wherein the medicament further comprises at least one further biologically active compound or metabolite, pharmaceutically acceptable salt, solvate or prodrug thereof.

Embodiment 20

The use according to embodiment 19, wherein the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent.

Embodiment 21

The use according to embodiment 20, wherein the biologically active compound is an anti-cancer agent.

Embodiment 22

The use according to embodiment 21, wherein the anti-cancer agent is cisplatin.

Embodiment 23

The use according to any one of embodiments 18-22, wherein the disease is cancer or pseudomyxoma peritonei.

Embodiment 24

The use according to embodiment 23, wherein the cancer is selected from lung cancer, breast cancer, colorectal cancer, thyroid cancer, prostate cancer, stomach cancer, pancreatic cancer, cancer of the appendix and ovarian cancer.

Embodiment 25

The use according to embodiment 23, wherein the cancer is signet ring cell carcinoma.

Embodiment 26

The use according to any one of embodiments 18-25, wherein the mucin is characterized as having a semi-hard or hard consistency.

Embodiment 27

The use according to any one of embodiments 18-26, wherein mucinous material is adapted for removal from a subject after a period of time following the administration of said medicament.

Embodiment 28

The use according to embodiment 27, wherein the period of time is selected from of about 5, 10, 15, 20, 30, 40, 50, or 60 minutes.

Embodiment 29

The use according to embodiment 27, wherein the period of time is selected from of about 1 hour, 1.5, 2, 2.5, 3, 3.5 or 4 hours.

Embodiment 30

A method for the treatment of a disease involving mucin, the method comprising administering a therapeutically effective amount of a composition comprising bromelain, or a proteolytic fraction thereof, and cysteamine, or a metabolite, pharmaceutically acceptable salt, solvate or prodrug thereof, to a subject in need thereof.

Embodiment 31

The method according to embodiment 30, wherein the composition additionally comprises at least one further biologically active compound, or a metabolite, pharmaceutically acceptable salt, solvate or prodrug thereof.

Embodiment 32

The method according to embodiment 31, wherein the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent.

Embodiment 33

The method according to embodiment 32, wherein the biologically active compound is an anti-cancer agent.

Embodiment 34

The method according to embodiment 33, wherein the anti-cancer agent is cisplatin.

Embodiment 35

The method according to any one of embodiments 30-34, wherein the disease is cancer or pseudomyxoma peritonei.

Embodiment 36

The method according to embodiment 35, wherein the cancer is selected from lung cancer, breast cancer, colorectal cancer, thyroid cancer, prostate cancer, stomach cancer, pancreatic cancer, cancer of the appendix and ovarian cancer.

Embodiment 37

The composition according to embodiment 35, wherein the cancer is signet ring cell carcinoma.

Embodiment 38

The method according to any one of embodiments 30-37, further comprising a step of removing mucinous material from a subject after a period of time following the administration of said composition or said medicament.

Embodiment 39

The method according to embodiment 38, wherein the period of time is selected from of about 5, 10, 15, 20, 30, 40, 50, or 60 minutes.

Embodiment 40

The method according to embodiment 38, wherein the period of time is selected from of about 1 hour, 1.5, 2, 2.5, 3, 3.5 or 4 hours.

Embodiment 41

A method of disintegrating and/or solubilizing mucinous material in a subject, comprising administering to the subject a therapeutically effective amount of a composition comprising bromelain, or a proteolytic fraction thereof, and cysteamine or a metabolite, pharmaceutically acceptable salt, solvate or prodrug thereof.

Embodiment 42

The method according to embodiment 41, wherein the mucin or mucinous material is characterized as having a semi-hard or hard consistency.

Embodiment 43

A composition comprising bromelain, or a proteolytic fraction thereof, and cysteamine or a metabolite, pharmaceutically acceptable salt, solvate or prodrug thereof, for use in disintegrating and/or solubilizing mucinous material in a subject.

Embodiment 44

The composition according to embodiment 43, wherein the mucin or mucinous material is characterized as having a semi-hard or hard consistency.

Embodiment 45

Use of a composition comprising bromelain, or a proteolytic fraction thereof, and cysteamine or a metabolite, pharmaceutically acceptable salt, solvate or prodrug thereof in the manufacture of a medicament for disintegrating and/or solubilizing mucinous material in a subject.

Embodiment 46

The use according to embodiment 45, wherein the mucin or mucinous material is characterized as having a semi-hard or hard consistency.

Embodiment 47

A kit comprising bromelain, or a proteolytic fraction thereof, cysteamine, or a metabolite, pharmaceutically acceptable salt, solvate or prodrug thereof, and optionally at least one biologically active compound, for simultaneous, separate or sequential use in the treatment of a disease involving mucin.

Embodiment 48

A kit when used for the treatment of a disease involving mucin comprising bromelain, or a proteolytic fraction thereof, cysteamine, or a metabolite, pharmaceutically acceptable salt, solvate or prodrug thereof, and optionally at least one biologically active compound.

Embodiment 49

A composition according to any one of embodiments 1-5, for use in enhancing the therapeutic efficacy of an anti-cancer compound in an anti-cancer regimen for the treatment of cancer or pseudomyxoma peritonei in a subject.

Embodiment 50

The composition according to embodiment 49, wherein the anti-cancer regimen is for the treatment of pseudomyxoma peritonei or a cancer selected from lung cancer, breast cancer, colorectal cancer, thyroid cancer, prostate cancer, stomach cancer, pancreatic cancer, cancer of the appendix and ovarian cancer.

Embodiment 51

The composition according to embodiment 49, wherein the cancer is signet ring cell carcinoma.

Embodiment 52

A composition according to any one of embodiments 1-5, for use in reducing the dose of an anti-cancer compound in an anti-cancer regimen for the treatment of cancer or pseudomyxoma peritonei in a subject.

Embodiment 53

The composition according to embodiment 52, wherein the anti-cancer regimen is for the treatment of pseudomyxoma peritonei or a cancer selected from lung cancer, breast cancer, colorectal cancer, thyroid cancer, prostate cancer, stomach cancer, pancreatic cancer, cancer of the appendix and ovarian cancer.

Embodiment 54

The composition according to embodiment 52, wherein the cancer is signet ring cell carcinoma.

Embodiment 55

A composition according to any one of embodiments 1-5, for use reducing the side effects of an anti-cancer compound in an anti-cancer regimen for the treatment of cancer or pseudomyxoma peritonei in a subject.

Embodiment 56

The composition according to embodiment 55, wherein the anti-cancer regimen is for the treatment of pseudomyxoma peritonei or a cancer selected from lung cancer, breast cancer, colorectal cancer, thyroid cancer, prostate cancer, stomach cancer, pancreatic cancer, cancer of the appendix and ovarian cancer.

Embodiment 57

The composition according to embodiment 55, wherein the cancer is signet ring cell carcinoma.

Embodiment 58

A method for enhancing the therapeutic efficacy of an anti-cancer compound in an anti-cancer regimen, comprising administering to a subject in need thereof a therapeutically effective amount of a composition according to any one of embodiments 1-5.

Embodiment 59

The method according to embodiment 58, wherein the anti-cancer regimen is for the treatment of pseudomyxoma peritonei or a cancer selected from lung cancer, breast cancer, colorectal cancer, thyroid cancer, prostate cancer, stomach cancer, pancreatic cancer, cancer of the appendix and ovarian cancer.

Embodiment 60

The method according to embodiment 59, wherein the cancer is signet ring cell carcinoma.

Embodiment 61

A method for reducing the dose of an anti-cancer compound in an anti-cancer regimen comprising administering to a subject in need thereof a therapeutically effective amount of a composition according to any one of embodiments 1-5.

Embodiment 62

The method according to embodiment 61, wherein the anti-cancer regimen is for the treatment of pseudomyxoma peritonei or a cancer selected from lung cancer, breast cancer, colorectal cancer, thyroid cancer, prostate cancer, stomach cancer, pancreatic cancer, cancer of the appendix and ovarian cancer.

Embodiment 63

The method according to embodiment 61, wherein the cancer is signet ring cell carcinoma.

Embodiment 64

A method for reducing the side effects of an anti-cancer compound in an anti-cancer regimen, comprising administering to a subject in need thereof a therapeutically effective amount of a composition according to any one of embodiments 1-5.

Embodiment 65

The method according to embodiment 64, wherein the anti-cancer regimen is for the treatment of pseudomyxoma peritonei or a cancer selected from lung cancer, breast cancer, colorectal cancer, thyroid cancer, prostate cancer, stomach cancer, pancreatic cancer, cancer of the appendix and ovarian cancer.

Embodiment 66

The method according to embodiment 64, wherein the cancer is signet ring cell carcinoma.

Embodiment 67

Use of bromelain, or a proteolytic fraction thereof, and cysteamine or a metabolite, pharmaceutically acceptable salt, solvate or prodrug thereof, in the manufacture of a medicament for enhancing the therapeutic efficacy of an anti-cancer compound in an anti-cancer regimen for the treatment of cancer or pseudomyxoma peritonei in a subject.

Embodiment 68

The use according to embodiment 67, wherein the medicament further comprises at least one further biologically active compound or metabolite, pharmaceutically acceptable salt, solvate or prodrug thereof.

Embodiment 69

The use according to embodiment 68, wherein the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent.

Embodiment 70

The use according to embodiment 69, wherein the biologically active compound is an anti-cancer agent.

Embodiment 71

The use according to embodiment 70, wherein the anti-cancer agent is cisplatin.

Embodiment 72

The use according to any one of embodiments 67-71, wherein the cancer is selected from lung cancer, breast cancer, colorectal cancer, thyroid cancer, prostate cancer, stomach cancer, pancreatic cancer, cancer of the appendix and ovarian cancer.

Embodiment 73

The use according to any one of embodiments 67-71, wherein the cancer is signet ring cell carcinoma.

Embodiment 74

Use of bromelain, or a proteolytic fraction thereof, and cysteamine or a metabolite, pharmaceutically acceptable salt, solvate or prodrug thereof, in the manufacture of a medicament for reducing the dose of an anti-cancer compound in an anti-cancer regimen for the treatment of cancer or pseudomyxoma peritonei in a subject.

Embodiment 75

The use according to embodiment 74, wherein the medicament further comprises at least one further biologically active compound or metabolite, pharmaceutically acceptable salt, solvate or prodrug thereof.

Embodiment 76

The use according to embodiment 75, wherein the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent.

Embodiment 77

The use according to embodiment 76, wherein the biologically active compound is an anti-cancer agent.

Embodiment 78

The use according to embodiment 77, wherein the anti-cancer agent is cisplatin.

Embodiment 79

The use according to any one of embodiments 74-78, wherein the cancer is selected from lung cancer, breast cancer, colorectal cancer, thyroid cancer, prostate cancer, stomach cancer, pancreatic cancer, cancer of the appendix and ovarian cancer.

Embodiment 80

The use according to any one of embodiments 74-78, wherein the cancer is signet ring cell carcinoma.

Embodiment 81

Use of bromelain, or a proteolytic fraction thereof, and cysteamine or a metabolite, pharmaceutically acceptable salt, solvate or prodrug thereof, in the manufacture of a medicament for reducing the side effects of an anti-cancer compound in an anti-cancer regimen for the treatment of cancer or pseudomyxoma peritonei in a subject.

Embodiment 82

The use according to embodiment 81, wherein the medicament further comprises at least one further biologically active compound or metabolite, pharmaceutically acceptable salt, solvate or prodrug thereof.

Embodiment 83

The use according to embodiment 82, wherein the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent.

Embodiment 84

The use according to embodiment 83, wherein the biologically active compound is an anti-cancer agent.

Embodiment 85

The use according to embodiment 84, wherein the anti-cancer agent is cisplatin.

Embodiment 86

The use according to any one of embodiments 81-85, wherein the cancer is selected from lung cancer, breast cancer, colorectal cancer, thyroid cancer, prostate cancer, stomach cancer, pancreatic cancer, cancer of the appendix and ovarian cancer.

Embodiment 87

The use according to any one of embodiments 81-85, wherein the cancer is signet ring cell carcinoma.

DETAILED DESCRIPTION

Definitions

Figure 1:
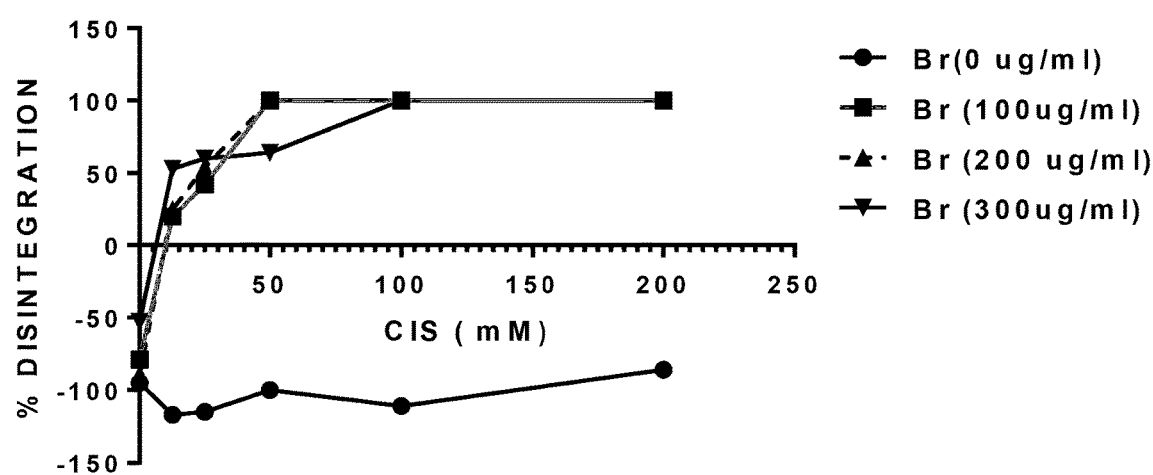
FIG. 1 shows either disintegration (with positive values) or hydration (with negative values) of mucinous material treated with cysteamine (CYS), bromelain (Br) or a combination of the two.
Figure 2:
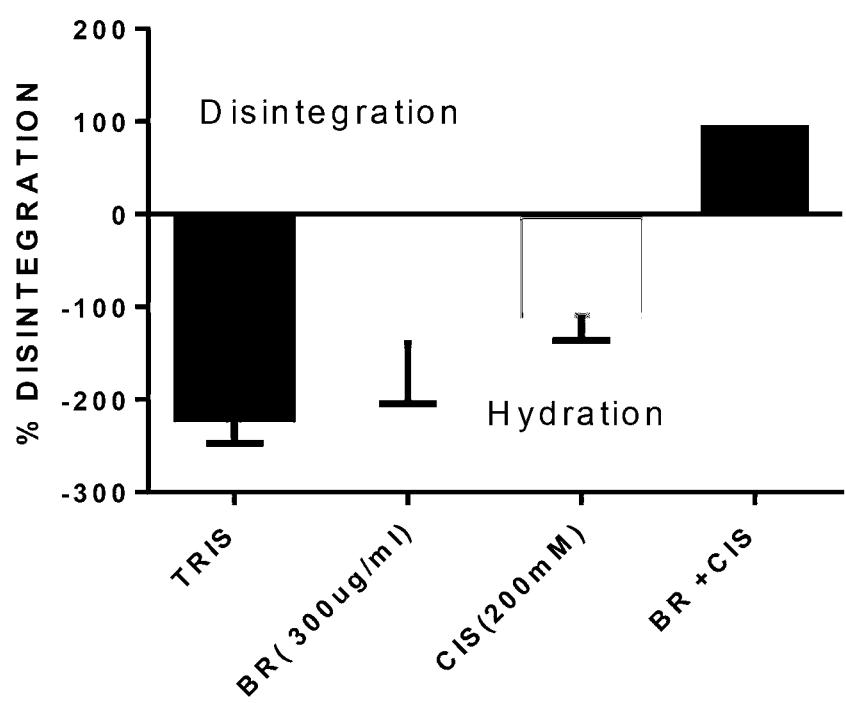
FIG. 2 shows that the combination of 200 µg/ml bromelain and 200 mM cysteamine completely disintegrates the mucin. Br=Bromelain; CIS=cysteamine; TRIS=Tris buffer.

As used herein, the term "cysteamine" refers to a compound of formula (I):

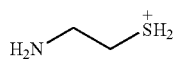

As used herein, reference to "cysteamine" includes, the various cysteamine salts, which include pharmaceutically acceptable salts of a cysteamine product, as well as prodrugs of cysteamine that may, for example, be readily metabolized in the body to produce cysteamine. Also included are esters, amides, alkylated compounds, phosphorylated compounds, sulfated compounds, analogs, derivatives, conjugates, and metabolites of cysteamine, which in combination with bromelain, or a proteolytic fraction thereof, have the ability as described herein to disintegrate and/or solubilize mucinous material and/or enhance the efficacy of an anti-cancer agent. Also included within the scope of the present embodiments are chemically modified forms of cysteamine by such techniques as labeling (for example, with radionuclides or various enzymes), or covalent polymer attachment such as pegylation (derivatization with polyethylene glycol) or mixtures thereof. Various analogs, derivatives, conjugates, and metabolites of cysteamine are well known and may be readily prepared and used by those skilled in the art. The disclosure is not limited with respect to a specific cysteamine salt or ester or derivative.

Pharmaceutically acceptable salts of cysteamine may comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH^{4+}$) and substituted ammonium ($N(R')^{4+}$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate.

The disclosure is not limited with respect to a specific cysteamine salt or ester or derivative; the compositions of the disclosure can contain any cysteamine or cysteamine derivative. Other derivatives and analogs of the active agents may be prepared using standard techniques known to those skilled in the art of synthetic organic chemistry, or may be deduced by reference to the pertinent literature.

The term "bromelain" ("Br") refers an extract of the pineapple plant (*Ananas Comosus*) and may incorporate any of a number of presently commercially available bromelain preparations. Bromelain comprises different thiol endopeptidases, phosphatases, glucosidases, peroxidases, cellulases, glycoproteins, carbohydrates and protease inhibitors. Accordingly, reference to bromelain is understood to encompass a combination of an enzymatic, and/or proteolytic fraction of bromelain which cleaves glycosidic linkages in mucin and a non-enzymatic compound in bromelain. Reference to a "proteolytic fraction" of bromelain refers to a subcomponent of bromelain which possesses proteolytic activity and which cleaves glycosidic linkages in mucin.

"Pharmaceutically acceptable salt" refers to conventional acid-addition salts or base-addition salts that retain the biological effectiveness and properties of the compounds of the compositions described herein and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flow ability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Prodrugs" and "solvates" of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of formula (I) or a metabolite, pharmaceutically acceptable salt or solvate of the compound. The transformation may occur by various mechanisms (e.g., by metabolic or chemical processes). A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

"Metabolites" of the compounds of the invention refer to the intermediates and products of metabolism.

The term "mucin" as used herein refers to any of a class of high molecular weight glycoproteins with a high content of clustered oligosaccharides O-glycosidically linked to tandem repeating peptide sequences which are rich in threonine, serine and proline and includes any member of the human mucin (MUC) family which consists of members designated MUC1 to MUC21 that have been sub-classified into secreted and transmembrane forms.

As used herein the term "mucinous material" refers to a composition comprising mucins or mucin glycoproteins and encompasses mucus and the mucinous secretions of cells, including cancer cells, and may additionally comprise cells and other cell-derived components.

As used herein the term "soft" as applied to the consistency of mucin or mucinous material the terms "soft mucin" or "soft mucinous material" refers mucin or mucinous material of a gelatinous, viscous, jelly-like texture and/or having a hardness index (described herein) as determined by the formula: Weight of mucin (g)/Area mucin occupies on a surface ($mm^2$) of ≤0.6.

As used herein the terms "semi-hard" as applied to the consistency of mucin or mucinous material the terms "semi-hard mucin" or "semi-hard mucinous material" refers mucin or mucinous material which is of a semi-solid texture, which is more compact than soft mucinous material, which is semi-opaque upon visual inspection and/or has a hardness index as determined by the formula: Weight of mucin (g)/Area mucin occupies on a surface (mm$^2$) of >0.6-1.2.

As used herein the terms "hard" as applied to the consistency of mucin or mucinous material the terms "hard mucin" or "hard mucinous material" refers mucin or mucinous material of a solid texture, which is more compact than semi-solid mucinous material, which is opaque upon visual inspection and/or has a hardness index as determined by the formula: Weight of mucin (g)/Area mucin occupies on a surface (mm$^2$) of >1.2.

As used herein, reference to a "disease involving mucin" refers to a disease wherein the overexpression of mucin, the overproduction of mucin or the aberrant accumulation of mucin or mucinous material is associated with the pathology or sequelae of a disease or disorder.

As used herein, the terms "treatment" or "treating" mean: (1) improving or stabilizing the subject's condition or disease or (2) preventing or relieving the development or worsening of symptoms associated with the subject's condition or disease.

As used herein, the terms "administration" or "administering" mean a route of administration for a compound disclosed herein. Exemplary routes of administration include, but are not limited to, oral, intravenous, intraperitoneal, intraarterial, and intramuscular. The preferred route of administration can vary depending on various factors, e.g., the components of the pharmaceutical composition comprising an agent as disclosed herein, site of the potential or actual disease and severity of disease.

As used herein, the terms "amount effective" or "effective amount" mean the amount of an composition disclosed herein that when administered to a subject for treating a disease, is sufficient to effect such treatment of the disease. The term "therapeutically effective amount" as used herein, includes within its meaning a non-toxic but sufficient amount of an agent or composition for use in the present invention to provide the desired therapeutic effect. The exact amount required will vary from subject to subject depending on factors such as the species being treated, the age and general condition of the subject, the severity of the condition being treated, the particular agent being administered, the mode of administration and so forth. Thus, it is not possible to specify an exact "effective amount" applicable to all embodiments. However, for any given case, an appropriate "effective amount" may be determined by one of ordinary skill in the art using only routine experimentation. An effective amount of a composition disclosed herein, used for the treatment of a disease involving mucin can vary depending upon the manner of administration, the age, body weight, and general health of the patient. Ultimately, the prescribers or researchers will decide the appropriate amount and dosage regimen.

The terms "synergy", "synergistic", "synergistic effect" and "synergistic combination" as used herein refers to a mixture of two or more discrete agents which, when combined, display a degree of activity, such as mucolytic activity, anti-cancer activity, anti-proliferative activity or cytotoxicity etc., which is greater than the expected additive effect of said agents. The terms also refer to the combined effect of administering an amount of one therapeutic agent that, when administered alone, produces no significant response but, when administered in combination with one or more other therapeutic compounds, produces an overall response that is significantly greater than that produced by the one or more other compounds alone.

The term "anti-cancer", as used herein, is intended to refer to the activity of suppressing the formation or growth of cancer cells, killing cancer cells, or inhibiting or blocking the metastasis of cancer cells, encompassing the meaning of the inhibition of cancer cell metastasis as well as the prophylaxis and treatment of cancer.

As used herein, the term "anti-cancer regimen" refers to a plan, or a regulated course intended to suppress the formation or growth of cancer cells, kill cancer cells or inhibit or block the metastasis of cancer cells, defining the drugs to be used, their dosage, the frequency of administration and duration of treatments.

As used herein, the terms "subject" and "patient" are used herein interchangeably. They refer to a human or another mammal (e.g., mouse, rat, rabbit, dog, cat, cattle, swine, sheep, horse or primate) that can be afflicted with or is susceptible to a disease or disorder but may or may not have the disease or disorder. In certain embodiments, the subject is a human being.

As used herein, the term "agent" means any small molecule chemical compound, antibody, nucleic acid molecule, or polypeptide or fragment thereof.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

A reference herein to a patent document or other matter which is given as prior art is not to be taken as an admission that that document or matter was known or that the information it contains was part of the common general knowledge as at the priority date of any of the claims.

Mucin

Mucins, the gel-forming components of mucinous secretions, are large polydisperse macromolecules (1,000 kDa) comprising a number of glycoprotein monomers (100-10, 000 kDa). The polymerization of individual glycoprotein units takes place through the formation of glycosidic linkages. The mucin is further cross-linked to each other through the formation of disulfide bonds by oxidation that takes place either enzymatically or through variation in pH.

The mucin family includes proteins that contain tandem repeat structures with a high proportion of prolines, threonines and serines (which constitute the PTS domain). Mucins are further defined by extensive glycosylation of the PTS domain through GalNAC O-linkages at the threonine and serine residues as well as other linkages. The human mucin (MUC) family consists of members designated MUC1 to MUC21 that have been sub-classified into secreted and transmembrane forms.

The secreted mucins (for example, MUC2, MUC5AC, MUC5B and MUC6) may form a physical barrier, which as a mucous gel provides protection for epithelial cells that line the respiratory and gastrointestinal tracts and form the ductal surfaces of organs such as the liver, breast, pancreas and kidney.

The transmembrane mucins (for example, MUC1, MUC4, MUC13 and MUC16) have a single membrane-spanning region and contribute to the protective mucous gel through their ectodomains of O-glycosylated tandem repeats that form rod-like structures that extend over 100 nm from the cell surface and beyond the ~10 nm glycocalyx.

MUC1 is aberrantly expressed in a high proportion of carcinomas and certain hematological malignancies making MUC1 overexpression one of the more common alterations in human cancers.

Clones of HT29 colon cancer with different types of mucin secretion have been found to have varying resistance to the common chemotherapy drugs 5FU and methotrexate. Mucin of colonic immunoreactivity conferring resistance to 5FU (mostly MUC 2) and that of gastric reactivity conferring resistance to methotrexate in patients with colorectal carcinoma mucinous histology is associated with poor response rate to chemotherapy and survival. Mucin is known to impede the cytotoxic effect of 5FU against growth of human pancreatic cancer cells. Thus, mucin can act as a cellular barrier limiting chemo therapeutic action. This is further evidenced by the fact that inhibition of mucin O-glycosylation enhances the cytotoxic effects of 5FU against pancreatic cancer cell lines but not against a mucin deficient cell line.

The isolation of mucinous material from subjects suffering from diseases involving mucin has revealed that there is inter-individual variation in the texture, elasticity, compactness and hydration of mucin. For example, mucinous secretions in PMP patients vary in compactness ranging from low (soft), medium to high (very compact) and may comprise gristly material that may be of cellular origin.

Accordingly, it is possible for mucinous material to be characterized according to its appearance and hardness. For example, a sample of mucin may be characterized by visual inspection and calculation of a hardness index, wherein a mucin sample is first visually assessed as being transparent, semi-opaque or opaque, and then weighed and hydrated for a defined period. Following hydration the area occupied by the mucin placed on a flat surface is then measured and the hardness index calculated according to the following formula: Weight of mucin (g)/Area mucin occupies on a surface ($mm^2$). Following such assessment the mucinous material may be characterized as soft, semi-hard or hard or having a soft, semi-hard or hard consistency, where the mucin is transparent, semi-opaque or opaque, respectively, and/or wherein the mucin is determined to have a hardness index of ≤0.6, >0.6-1.2, or >1.2, respectively (Akhter, J. et al. 2014 *Am J Cancer Res*, 4(5):495-507).

Bromelain

As outlined above, an extract of the pineapple plant (*Ananas Comosus*), comprises different thiol endopeptidases and other components such as phosphatases, glucosidases, peroxidases, cellulases, glycoproteins, carbohydrates and several protease inhibitors. Various preparations of bromelain are commercially available and methods for the extraction and purification of bromelain from the stem of the pineapple plant are known in the art as well as methods for the extraction of proteolytically active components of bromelain have also been described (U.S. Pat. Nos. 3,002,891; 3,442,764; 3,455,787; Harrach et al. 1995. *J Protein Chem*, 14(1):41-52; Harrach et al. 1998. *J Protein Chem*, 17(4): 351-61, incorporated herein by reference).

Disintegration of Mucin

It will be appreciated that mucinous material characterized as soft is easier to disintegrate and/or solubilize than semi-hard mucinous material, and that semi-hard mucinous material is easier to disintegrate and/or solubilize than hard mucinous material.

The inventors have shown that the combination of a mucolytic agent with bromelain may be used for the disintegration of mucin. Herein, the inventors have further surprisingly found that a novel combination of cysteamine and bromelain has enhanced efficacy in the disintegration and/or solubilization of mucin, than either agent alone or other combinations involving bromelain.

Accordingly, in one embodiment the present invention provides a composition comprising a synergistic mucolytic combination of bromelain, or a proteolytic fraction thereof, and cysteamine, or a metabolite, pharmaceutically acceptable salt, solvate or prodrug thereof.

In a further embodiment, the composition additionally comprises at least one further biologically active compound, or a metabolite, pharmaceutically acceptable salt, solvate or prodrug thereof. In a further embodiment, the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent. In a preferred embodiment, the biologically active compound is agent is an anti-cancer agent.

Furthermore, the inventors have surprisingly found that disintegration and/or solubilization of mucinous material which is characterized as having a semi-hard or hard consistency is dramatically enhanced when exposed to a combination of cysteamine and bromelain, when compared to then either agent alone or other combinations involving bromelain.

As outlined above, the mucinous material in a subject may be characterized as being of a soft, semi-hard or hard consistency. As described herein, the present inventors have demonstrated that the time taken to disintegrate and/or solubilize mucinous material may be substantially reduced. In particular the speed and efficiency for the disintegration and/or solubilization of semi-hard or hard mucinous material may be dramatically reduced when such mucin is exposed to a combination of cysteamine and bromelain, or a proteolytic fraction thereof, in comparison to other combinations. Accordingly, such compositions of the present invention may be used to substantially reduce the amount of time taken to disintegrate and/or solubilize mucinous material in subject and thereby facilitate its removal or extraction from the subject.

Therefore it will be appreciated that the use of the compositions of the invention described herein may provide various advantages including, but not limited to, faster, more thorough and more efficient removal of mucinous material from a subject than is obtainable using current therapies.

In another embodiment, the present invention provides a composition comprising bromelain, or a proteolytic fraction thereof, and cysteamine, or a metabolite, pharmaceutically acceptable salt, solvate or prodrug thereof for the treatment of a disease involving mucin. In another embodiment the subject is diagnosed with an accumulation of mucinous material. In a preferred embodiment the mucinous material includes mucinous material characterized as having a semi-hard or hard consistency.

In another embodiment, the present invention provides use of a composition comprising bromelain, or a proteolytic fraction thereof, and cysteamine, or a metabolite, pharmaceutically acceptable salt, solvate or prodrug thereof in the manufacture of a medicament for the treatment of a disease involving mucin. In another embodiment the subject is diagnosed with an accumulation of mucinous material. In a preferred embodiment the mucinous material includes mucinous material characterized as having a semi-hard or hard consistency.

In another embodiment, the present invention provides a method of treating a subject with a disease involving mucin comprising administering the subject a therapeutically effective amount of a composition comprising bromelain, or a proteolytic fraction thereof, and cysteamine, or a metabolite, pharmaceutically acceptable salt, solvate or prodrug thereof. In another embodiment the subject is diagnosed with an accumulation of mucinous material. In a preferred embodiment the mucinous material includes mucinous material characterized as having a semi-hard or hard consistency.

In a further embodiment, the composition administered in the method of the invention additionally comprises at least one further biologically active compound, or a metabolite, pharmaceutically acceptable salt, solvate or prodrug thereof. In a further embodiment, the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent. In a preferred embodiment, the biologically active compound is agent is an anti-cancer agent.

In another embodiment, the present invention provides a composition comprising bromelain, or a proteolytic fraction thereof, and cysteamine, or a metabolite, pharmaceutically acceptable salt, solvate or prodrug thereof for the disintegration and/or solubilization of mucinous material in a subject. In another embodiment the subject is diagnosed with an accumulation of mucinous material. In a preferred embodiment the mucinous material includes mucinous material characterized as having a semi-hard or hard consistency.

In another embodiment, the present invention provides use of a composition comprising bromelain, or a proteolytic fraction thereof, and cysteamine, or a metabolite, pharmaceutically acceptable salt, solvate or prodrug thereof in the manufacture of a medicament for the disintegration and/or solubilization of mucinous material in a subject. In another embodiment the subject is diagnosed with an accumulation of mucinous material. In a preferred embodiment the mucinous material includes mucinous material characterized as having a semi-hard or hard consistency.

In another embodiment, the present invention provides a method of disintegration and/or solubilization of mucinous material in a subject comprising administering the subject a therapeutically effective amount of a composition comprising bromelain, or a proteolytic fraction thereof, and cysteamine, or a metabolite, pharmaceutically acceptable salt, solvate or prodrug thereof. In another embodiment the subject is diagnosed with an accumulation of mucinous material. In a preferred embodiment the mucinous material includes mucinous material characterized as having a semi-hard or hard consistency.

In a further embodiment, the composition administered in the foregoing method of the invention additionally comprises at least one further biologically active compound, or a metabolite, pharmaceutically acceptable salt, solvate or prodrug thereof. In a further embodiment, the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent. In a preferred embodiment, the biologically active compound is agent is an anti-cancer agent.

In another embodiment, the present invention provides a composition comprising bromelain, or a proteolytic fraction thereof, and cysteamine, or a metabolite, pharmaceutically acceptable salt, solvate or prodrug thereof for the treatment of cancer or pseudomyxoma peritonei. In another embodiment, the cancer is selected from lung cancer, breast cancer, colorectal cancer, thyroid cancer, prostate cancer, stomach cancer, pancreatic cancer, cancer of the appendix and ovarian cancer. In another embodiment, the cancer is an adenocarcinoma. In a further embodiment, the adenocarcinoma is a signet ring cell carcinoma. In another embodiment the subject is diagnosed with an accumulation of mucinous material. In a preferred embodiment the mucinous material includes mucinous material characterized as having a semi-hard or hard consistency.

In another embodiment, the present invention provides use of a composition comprising bromelain, or a proteolytic fraction thereof, and cysteamine, or a metabolite, pharmaceutically acceptable salt, solvate or prodrug thereof in the manufacture of a medicament for the treatment of cancer or pseudomyxoma peritonei. In another embodiment, the cancer is selected from lung cancer, breast cancer, colorectal cancer, thyroid cancer, prostate cancer, stomach cancer, pancreatic cancer, cancer of the appendix and ovarian cancer. In another embodiment, the cancer is an adenocarcinoma. In a further embodiment, the adenocarcinoma is a signet ring cell carcinoma. In another embodiment the subject is diagnosed with an accumulation of mucinous material. In a preferred embodiment the mucinous material includes mucinous material characterized as having a semi-hard or hard consistency.

In another embodiment, the present invention provides a method for the treatment of cancer or pseudomyxoma peritonei comprising administering the subject a therapeutically effective amount of a composition comprising bromelain, or a proteolytic fraction thereof, and cysteamine, or a metabolite, pharmaceutically acceptable salt, solvate or prodrug thereof. In another embodiment, the cancer is selected from lung cancer, breast cancer, colorectal cancer, thyroid cancer, prostate cancer, stomach cancer, pancreatic cancer, cancer of the appendix and ovarian cancer. In another embodiment, the cancer is an adenocarcinoma. In a further embodiment, the adenocarcinoma is a signet ring cell carcinoma. In another embodiment the subject is diagnosed with an accumulation of mucinous material. In a preferred embodiment the mucinous material includes mucinous material characterized as having a semi-hard or hard consistency.

In a further embodiment, the composition additionally comprises at least one further biologically active compound, or a metabolite, pharmaceutically acceptable salt, solvate or prodrug thereof. In a further embodiment, the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent. In a preferred embodiment, the biologically active compound is agent is an anti-cancer agent.

Compositions, Medicaments and Kits

The present invention provides pharmaceutical compositions, medicaments and kits of the present invention and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions, for example water or water-propylene glycol solutions for parenteral injection or intraperitoneal administration or injection, or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen. Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Compositions and medicaments of the present invention may comprise a pharmaceutically acceptable carrier, adjuvant, excipient and/or diluent. The carriers, diluents, excipients and adjuvants must be "acceptable" in terms of being compatible with the other ingredients of the composition or medicament, and are generally not deleterious to the recipient thereof. Non-limiting examples of pharmaceutically acceptable carriers or diluents are demineralized or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysiloxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxyl-propyl-methyl-cellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from about 10% to about 99.9% by weight of the composition or medicament.

Compositions and medicaments of the present invention may be in a form suitable for administration by injection (e.g. for parenteral administration including intraperitoneal, subcutaneous, intramuscular or intravenous injection), by oral administration (such as capsules, tablets, caplets, and elixirs, for example), by topical administration (e.g. in the form of an ointment, cream or lotion, or a form suitable for delivery as an eye drop), or by intranasal inhalation (e.g. in the form of aerosols).

For administration as an injectable solution or suspension, non-toxic parenterally acceptable diluents or carriers can include, Ringer's solution, isotonic saline, phosphate buffered saline, ethanol and 1,2 propylene glycol. Methods for preparing parenterally administrable compositions and medicaments are apparent to those of ordinary skill in the art, and are described in more detail in, for example, Remington's Pharmaceutical Science, 15th ed Mack Publishing Company, Easton, Pa.

For oral administration, some examples of suitable carriers, diluents, excipients and adjuvants include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavoring and colorings agents. When used in capsule form the capsules may be coated with compounds such as glyceryl monostearate or glyceryl stearate which delay disintegration. Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavorings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Formulations for oral administration may comprise one or more emulsifying agents. Suitable emulsifying agents include dispersing agents as exemplified above or natural gums such as guar gum, gum acacia or gum tragacanth.

Topical formulations of the present invention may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilized. Sterilization may be achieved by autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturizer such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil, wool fat or its derivatives, or a fatty acid such as stearic or oleic acid together with an alcohol such as propylene glycol or macrogols.

Compositions and medicaments of the present invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions of the present invention may be formulated for targeted delivery or sustained delivery. For example, the compositions can be enterically coated to promote delivery to the small intestine or at a desired pH of the lower gastrointestinal tract. An enterically coated drug or tablet refers, generally, to a drug or tablet that is coated with a substance (an "enteric coating") that remains intact or substantially intact such that the drug or tablet is passed through the stomach but dissolves and releases the drug in the small intestine.

Any of the formulations of the disclosure can be administered in a sustained release form. The sustained release formulation has the advantage of delivery over an extended period of time without the need for repeated administrations of the formulation.

Sustained release can be achieved, for example, with a sustained release material such as a wafer, an immunobead, a micropump or other material that provides for controlled slow release of the composition. Such controlled release materials are well known in the art and available from commercial sources. In addition, a bioerodible or biodegradable material can be formulated with active agents of the invention, such as polylactic acid, polygalactic acid, regenerated collagen, multilamellar liposomes or other conventional depot formulations, can be implanted to slowly release the compositions. The use of infusion pumps, matrix entrapment systems, and transdermal delivery devices also are contemplated in the invention.

Active agents/formulations also can be advantageously enclosed in micelles or liposomes. Liposome encapsulation technology is well known. Liposomes can be targeted to a specific tissue, such as neural tissue, through the use of receptors, ligands or antibodies capable of binding to an antigen or target in the desired tissue. The preparation of these formulations is well known in the art (see, for example, Pardridge, supra (1991), and Radin and Metz, Meth Enzymol. 98:613-618 (1983)).

The compositions of the present invention may also include additional pharmaceutically acceptable carriers or vehicles. A pharmaceutically acceptable carrier or vehicle refers, generally, to materials that are suitable for administration to a subject wherein the carrier or vehicle is not biologically harmful, or otherwise, cause undesirable effects. Such carriers or vehicles are typically inert ingredients of a medicament. Typically a carrier or vehicle is administered to a subject along with an active ingredient without causing any undesirable biological effects or interacting in a deleterious manner with any of the other components of a pharmaceutical composition in which it is contained.

An active ingredient, pharmaceutical or other composition of the disclosure can comprise a stabilizing agent. Stabilizing agents, generally, refer to compounds that lower the rate at which a pharmaceutical degrades, particularly an oral pharmaceutical formulation under environmental conditions of storage. Certain stabilizers are suitable for intravascular delivery. For example, one or more of the following stabilizers can be used in formulating a cysteamine product for intravascular delivery: α-tocopherol, 2,6-di-tert-butyl-4-methylphenol (BHT), tocopherol acetate, 2-tert-butyl-4-hydroxyanisole and/or 3-tert-butyl-4-hydroxyanisole (BHA), dodecyl gallate, acetate and ascorbic acid.

Supplementary active ingredients such as adjuvants or biological response modifiers can also be incorporated into compositions and medicaments of the present invention.

Preferably, the composition of the present invention is delivered by oral, intravenous or intraperitoneal administration when treating mucin-secreting cancers.

Preferably, the composition of the present invention is delivered by intraperitoneal injection when treating PMP.

Another aspect of this invention is a kit comprising a therapeutically effective amount of each of cysteamine, bromelain, or a proteolytic fraction thereof, optionally one or more biologically active compounds, and a pharmaceutically acceptable carrier, vehicle or diluent.

Another aspect of this invention is a kit comprising a therapeutically effective amount of each of cysteamine, bromelain, or a proteolytic fraction thereof, optionally one or more biologically active compounds, and at least one chemotherapeutic agent, wherein the amount of the two or more ingredients results in a desired therapeutic effect.

Kits of the present invention may comprise components to assist in performing the methods of the present invention such as, for example, administration device(s), buffer(s), and/or diluent(s). The kits may include containers for housing the various components and instructions for using the kit components in the methods of the present invention.

In certain embodiments, the kits may be combined kits.

In other embodiments, the kits may be fragmented kits.

Dosages and Routes of Administration

The agents, compositions and medicaments can be administered to a recipient by standard routes, including, but not limited to, parenteral (e.g. intraperitoneal, intravenous, intraspinal, subcutaneous or intramuscular), oral, topical, or mucosal routes (e.g. intranasal). In some embodiments, they may be administered to a recipient in isolation or in combination with other additional therapeutic agent(s). In such embodiments the administration may be simultaneous or sequential.

In general, the agents, compositions and medicaments can be administered in a manner compatible with the route of administration and physical characteristics of the recipient (including health status) and in such a way that the desired effect(s) are induced (i.e. therapeutically effective, immunogenic and/or protective). For example, the appropriate dosage may depend on a variety of factors including, but not limited to, a subject's physical characteristics (e.g. age, weight, sex), whether the agent, composition or medicament is being used as single agent or adjuvant therapy, the progression (i.e. pathological state) of a disease or condition being treated, and other factors readily apparent to those of ordinary skill in the art.

Various general considerations when determining an appropriate dosage of the agents, compositions and medicaments are described, for example, in Gennaro et al. (Eds), (1990), "Remington's Pharmaceutical Sciences", Mack Publishing Co., Easton, Pa., USA; and Gilman et al., (Eds) (1990), "Goodman And Gilman's: The Pharmacological Bases of Therapeutics", Pergamon Press.

In general, an agent, composition or medicament of the present invention may be administered to a patient in an amount of from about 50 micrograms to about 500 mg of active component(s). Generally, an effective dosage is expected to be in the range of about 0.001 mg to about 1000 mg of active component(s) per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; or about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; or about 5.0 mg to about 15 mg per kg body weight per 24 hours.

In other embodiments, it is envisaged that higher does may be used. In certain embodiments it is envisioned that the dosage may vary from between about 1 mg component/Kg body weight to about 5000 mg component/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, and 5000 mg/Kg body weight.

Typically, in treatment applications, the treatment may be for the duration of the disease state or condition. Further, it will be apparent to one of ordinary skill in the art that the optimal quantity and spacing of individual dosages can be determined by the nature and extent of the disease state or condition being treated, the form, route and site of administration, and the nature of the particular subject being treated. Optimum dosages can be determined using conventional techniques.

In many instances (e.g. preventative applications), it may be desirable to have several or multiple administrations of an agent, composition or medicament of the present invention which may, for example, be administered 1, 2, 3, 4, 5, 6, 7, 8, 9, 10, or more times. The administrations may be from about one to about twelve week intervals, and in certain embodiments from about one to about four week intervals. Periodic re-administration is also contemplated.

It will also be apparent to one of ordinary skill in the art that the optimal course of administration can be ascertained using conventional course of treatment determination tests.

Where two or more entities (e.g. agents or medicaments) are administered to a subject "in conjunction", they may be administered in a single composition at the same time, or in separate compositions at the same time, or in separate compositions separated in time.

Certain embodiments of the present invention involve administration of the agents, compositions or medicaments in multiple separate doses. Accordingly, the methods for prophylactic and therapeutic treatment described herein encompass the administration of multiple separated doses to a subject, for example, over a defined period of time. Accordingly, in some embodiments the methods include administering a priming dose, which may be followed by a booster dose. In various embodiments, the agent, composition or medicament is administered at least once, twice, three times or more.

The agents, compositions and medicaments may generally be administered in an effective amount to achieve an intended purpose. More specifically, they may be administered in a therapeutically effective amount which means an amount effective to prevent development of, or to alleviate the existing symptoms of, a target disease or condition. Determination of effective amounts is well within the capability of persons of ordinary skill in the art. For example, a therapeutically effective dose of the agents, compositions and medicaments can be estimated initially from cell culture assays. For example, a dose can be formulated in animal models to achieve a circulating concentration range that includes the IC50 as determined in cell culture. Such information can be used to more accurately determine useful doses in humans and other mammalian subjects.

A therapeutically effective dose refers to that amount of the agent, composition or medicament to prevent development of symptoms, ameliorate symptoms and/or prolong the survival of the subject under treatment. Toxicity and therapeutic efficacy of the agents, compositions and medicaments can be determined by standard pharmaceutical assays in cell cultures, and/or experimental animals (e.g. by determination of the LD50 (the dose lethal to 50% of the population) and the ED50 (the dose therapeutically effective in 50% of the population)). The dose ratio between toxic and therapeutic effects is the therapeutic index which can be expressed as the ratio between LD50 and ED50. Agents, compositions and medicaments which exhibit high therapeutic indices are preferred. The data obtained from such cell culture assays and/or animal studies may be used to formulate a range of dosage for use in humans or other mammals. The dosage of such compounds lies preferably within a range of circulating concentrations that include the ED50 with little or no toxicity. The dosage may vary within this range depending upon the dosage form employed and the administration route utilized. The exact formulation, route of administration and dosage can be selected without difficulty by an individual physician in view of the subject's condition (see, for example, Fingl et al., (1975), in "The Pharmacological Basis of Therapeutics", Ch. 1 p. 1, which is incorporated herein by reference). Dosage amount and interval may be adjusted individually to provide plasma levels of the active agent sufficient to achieve and maintain the desired therapeutic effect/s and/or a minimal effective concentration (MEC). Dosages necessary to achieve the MEC will depend on the route of administration and other individual characteristics. Bioassays and/or HPLC assays may be used to determine plasma concentrations.

Dosage intervals may also be determined using MEC value. In general, the agents, compositions and medicaments may be administered using a regimen which maintains plasma levels above the MEC for between about 10%-90% of the time, preferably between 30%-90% and more preferably between about 50%-90%. In embodiments where local administration or selective uptake is utilized, the effective local concentration of the drug may not be related to plasma concentration.

In one embodiment, the dosage is about 500-50,000 mg/kg of body weight/day of cysteamine, or a metabolite, pharmaceutically acceptable salt, solvate or prodrug thereof. In another embodiment, the dosage when administered into the intraperitoneal cavity or into the tumor itself is about 2000 mg/kg of body weight/day, or about 2500 mg/kg of body weight/day of a cysteamine, or a metabolite, pharmaceutically acceptable salt, solvate or prodrug thereof. In another embodiment, the dosage when administered orally is about 10,000 mg/kg of body weight/day of cysteamine, or a metabolite, pharmaceutically acceptable salt, solvate or prodrug thereof.

In one embodiment, the dosage when administered into the intraperitoneal cavity or into the tumor itself is about 10-50 mg/kg of body weight/day of the one or more compounds in Br, or a metabolite, pharmaceutically acceptable salt, solvate or prodrug of said compound. In another embodiment, the dosage when administered orally is about 50-1000 mg/kg of body weight/day of the one or more compounds in Br, or a metabolite, pharmaceutically acceptable salt, solvate or prodrug of said compound.

In one embodiment the dosage of cisplatin is in the range of 20 mg/m$^2$ to about 120 mg/m$^2$.

A preferred dosage of the biologically active compound, or a metabolite, pharmaceutically acceptable salt, solvate or prodrug of said compound is in accordance with the recommended dosage range as indicated in MIMS (the publication "The Monthly Index of Medical Specialities").

Combinations

As described herein, the compositions of the present invention comprise bromelain, or a proteolytic fraction thereof, and cysteamine or a metabolite, pharmaceutically acceptable salt, solvate or prodrug thereof and may further include one or more biologically active compound. Such agents may include a mucolytic agent, N-glycosylation inhibitor, sialyltransferase inhibitor, multi-drug transport inhibitor, NSAID, antibiotic, anti-cancer agent and anti-inflammatory agent.

Accordingly, the compositions of the present invention may comprise or be used in combination (administered together or sequentially) with one or more anti-cancer treatments such as radiation therapy, and/or one or more chemotherapeutic agents such as cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4~[2-[4-[(11R)-3,10-dibromo-8-chloro-6,11-dihydro-5H-benzo[5,6]cyclohepta [1,2-b]pyridin-11-yl-]-1-piperidinyl]-2-oxoehtyl]-1-piperidinecarboxamide, or SCH 66336 from Schering-Plough Corporation, Kenilworth, N.J.), tipifamib (Zamestra® or R115777 from Janssen Pharmaceuticals), L778.123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, lressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, Cytoxan, and gemcitabine.

In another embodiment the compositions of the invention may comprise or be used in combination (administered together or sequentially) with one or more N-glycosylation inhibitors, sialyltransferase inhibitors, multi-drug transport inhibitors, NSAIDs, antibiotics, and anti-inflammatory agents.

In a preferred embodiment, the present invention provides a synergistic mucolytic and/or anti-cancer combination of bromelain, or a proteolytic fraction thereof, and cysteamine or a metabolite, pharmaceutically acceptable salt, solvate or prodrug thereof and cisplatin.

Therapeutic Methods

The present invention provides methods for the disintegration and/or solubilization of mucinous material and methods of treating a disease involving mucin, wherein disintegration and/or solubilization of mucinous material is desired in order to facilitate its removal from a subject in need thereof.

The methods comprise administering a therapeutically effective amount of a combination of bromelain, or a proteolytic fraction thereof, and cysteamine, or a metabolite, pharmaceutically acceptable salt, solvate or prodrug thereof, described herein, to a subject (e.g., a mammal such as a human). In one embodiment the method includes the step of administering to the subject a therapeutically effective amount of a composition according to the invention in an amount sufficient to treat, prevent, delay, ameliorate, stabilize, a disease involving mucin or one or more side effects thereof. Thus, in one embodiment of the present invention there is provided a method of treating a cancer in a subject comprising administering to the subject a therapeutically effective amount of a composition according to the present invention.

In another embodiment, the present invention provides a method of treating pseudomyxoma peritonei in a subject comprising administering to the subject a therapeutically effective amount of a composition according to the present invention.

As described herein, the compositions of the invention also have a direct anti-cancer effect upon tumor cells and therefore possess both anti-cancer and mucolytic activities.

The compositions of the invention may be used in, or in the manufacture of a medicament for, the treatment of cancer either alone, or in combination with one or more anti-cancer treatments.

On account of the enhanced mucolytic activities observed for the compositions of the present invention, the disintegration and/or solubilization of mucinous material facilitates not only the removal of such material from a subject but also improves the effectiveness of therapeutic agents, increases the cellular uptake of a therapeutic agents; improves access to the surface of a cell, improves the efficacy of chemotherapy, and/or provides a means for reducing the dose of a therapeutic agent required for treating a subject with a disease involving mucin.

Additionally, by the methods of the invention, therapeutic agents can be administered at lower doses to the subject thereby decreasing any side effects associated with increased doses of the therapeutic agent while maintaining its efficacy.

In one embodiment the present invention provides a method of treatment of a disease involving mucin comprising analyzing the consistency of an accumulation of mucinous material within or obtained from a subject, followed by administration of a therapeutically effective amount of a composition comprising bromelain, or a proteolytic fraction thereof, and cysteamine or a metabolite, pharmaceutically acceptable salt, solvate or prodrug thereof. The amount of composition to be administered or the period of time for which the mucinous material is exposed to the composition may be appropriately adjusted where the mucinous material is characterized as having a semi-hard or hard consistency. For example, where the mucinous material is determined to be of a semi-hard, or hard consistency, the concentrations of the respective components of the composition may be increased, and/or the period of time for which the mucinous material is exposed to the composition may be increased.

In one embodiment the present invention provides a method for the treatment of a disease involving mucin comprising the steps of i) analyzing the consistency of mucinous material in a subject; and ii) administering to the subject a therapeutically effective amount of a composition comprising bromelain, or a proteolytic fraction thereof, and cysteamine or a metabolite, pharmaceutically acceptable salt, solvate or prodrug thereof, wherein said therapeutically effective amount is determined on the basis of the analysis performed in step i). In a preferred embodiment, the consistency is analyzed using calculation of a hardness index of mucinous material. In a preferred embodiment, the hardness index is calculated through the use of non-invasive imaging.

In another embodiment, the hardness index is calculated using a sample of mucin obtained from the subject. In a preferred embodiment, the mucinous material is determined to have a semi-hard or hard consistency.

For example, a sample of mucin may be analyzed by visual inspection and/or calculation of a hardness index, wherein a mucin sample obtained from a subject is first visually assessed as being transparent, semi-opaque or opaque, and then weighed and hydrated for a defined period. Following hydration the area occupied by the mucin placed on a flat surface is then measured and the hardness index calculated according to the following formula: Weight of mucin (g)/Area mucin occupies on a surface ($mm^2$). Following such analysis the mucinous material may be characterized as having a soft, semi-hard or hard consistency where the mucin is transparent, semi-opaque or opaque, respectively, and/or wherein the mucin is determined to have a hardness index of ≤0.6, >0.6-1.2, or >1.2, respectively (Akhter, 0.1 et al. 2014 *Am J Cancer Res,* 4(5):495-507).

Alternatively, non-invasive imaging techniques such as magnetic resonance imaging (MRI), ultrasonography or computed tomography (CT) can be used to assess the consistency of accumulated mucinous material in a subject.

In one embodiment, diffusion restriction MRI is performed in order to determine the nature of the mucinous material and calculate a hardness index. The skilled addressee may readily determine a correlation coefficient between the characterization of the mucinous material via a non-invasive imaging technique and the hardness index determined for a sample of the mucinous material taken from a patient using the methods outlined above.

In one embodiment the present invention provides a method for the treatment of a disease involving mucin comprising the steps of i) calculating a hardness index of the mucinous material in or obtained from a subject; and ii) administering to the subject a therapeutically effective amount of a synergistic mucolytic composition comprising bromelain, or a proteolytic fraction thereof, and cysteamine or a metabolite, pharmaceutically acceptable salt, solvate or prodrug thereof, wherein the amount of and/or duration of treatment with the composition is determined on the basis of the hardness index calculated in step i). In a preferred embodiment the calculation of the hardness index is performed using diffusion restricted MRI. In a preferred embodiment, the mucinous material is determined to have a semi-hard or hard consistency.

In one embodiment the present invention provides a method for the treatment of a disease involving mucin comprising the steps of i) obtaining a sample of mucinous material from a subject; ii) calculating a hardness index of the mucinous material in a subject; and iii) administering to the subject a therapeutically effective amount of a composition comprising bromelain, or a proteolytic fraction thereof, and cysteamine or a metabolite, pharmaceutically acceptable salt, solvate or prodrug thereof, wherein the amount of and/or duration of treatment with the composition is determined on the basis of the hardness index calculated in step ii). In a preferred embodiment, the mucinous material is determined to have a semi-hard or hard consistency.

In one embodiment the present invention provides a method for the treatment of a disease involving mucin comprising the steps of i) obtaining a sample of mucinous material from a subject; ii) calculating a hardness index of the mucinous material in a subject according to the formula: Weight of mucin (g)/Area mucin occupies on a surface ($mm^2$); and iii) administering to the subject a therapeutically effective amount of a composition comprising bromelain, or a proteolytic fraction thereof, and cysteamine or a metabolite, pharmaceutically acceptable salt, solvate or prodrug thereof, wherein the amount of and/or duration of treatment with the composition is determined on the basis of the hardness index calculated in step ii). In another embodiment of the methods described herein, solubilized or disintegrated mucinous material is removed from the subject after a period of time following administration of the composition. The removal of the mucinous material may be performed according to any means know to the skilled addressee which are suitable for the removal of such material from a subject. In one embodiment, the mucinous material is removed from the subject via a syringe or catheter.

In another embodiment, the period of time which elapses between administration of the compositions described herein and removal of mucinous material from, the subject may be determined on the basis of analysis of the consistency or hardness index which is calculated for the mucinous material. That is, the period of time for which the mucinous material is exposed to the composition of the present invention may be determined on the basis of the consistency or hardness of the mucinous material. For example, where analysis reveals that the mucinous material has a semi-hard consistency or a hardness index greater than about 0.6 to about 1.2, such material may require a longer exposure to the compositions described herein than mucinous material determined to have a soft or having a hardness index lower than 0.6, in order to achieve a similar degree of disintegration or solubilization. Where analysis reveals that the mucinous material has a hard consistency or has a hardness index greater than about 1.2, such material may require a longer exposure to the compositions described herein than mucinous material determined to have a semi-hard consistency or a hardness index greater than about 0.6 to about 1.2, in order to achieve a similar degree of disintegration or solubilization.

In one embodiment, the mucinous material is removed after a period of time ranging from about 5 minutes to about 4 hours. In one embodiment, the mucinous material is removed after a period of about 5, 10, 15, 20, 30, 40, 50, or 60 minutes following administration of the composition. In another embodiment, the mucinous material is removed after a period of about 1 hour, 1.5, 2, 2.5, 3, 3.5 or 4 hours following administration of the composition.

In a further embodiment of the foregoing methods of the present the composition comprises at least one further biologically active compound, or a metabolite, pharmaceutically acceptable salt, solvate or prodrug thereof. In another embodiment, the biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent. In a further embodiment, the biologically active compound is agent is an anti-cancer agent. In a preferred embodiment the anti-cancer agent is cisplatin.

Typically, in anti-cancer treatment applications, the treatment may be for the duration of the cancer. Further, it will be apparent to one of ordinary skill in the art that the optimal quantity and spacing of individual dosages can be determined by the nature and extent of the disease state or condition being treated, the form, route and site of administration, and the nature of the particular subject being treated. Optimum dosages can be determined using conventional techniques.

It is intended that anti-cancer compounds are used for treating the types of cancer for which they are normally utilized, e.g. first and second line standard of care drugs. In one embodiment, the anti-cancer compound(s) are provided or administered in their normal doses, in which case the provision or administration of synergistic mucolytic composition described herein primarily increases the therapeutic efficacy of the agent.

In one embodiment the therapeutic efficacy of an anti-cancer compound may be enhanced by about 10% to about 2000%. In one embodiment the therapeutic effect may be enhanced by about 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 1050%, 1100%, 1150%, 1200%, 1250%, 1300%, 1350%, 1400%, 1450%, 1500%, 1550%, 1600%, 1650%, 1700%, 1750%, 1800%, 1850%, 1900%, 1950% or about 2000%.

In another embodiment, the dose of an anti-cancer compound may be provided or administered at a reduced dose when combined with a synergistic composition of the present invention. Such dose reduction or enhancement of therapeutic efficacy of the anti-cancer compound may permit the use of particular anti-cancer compound for treating a cancer for which the agent is not currently standard therapy. The reduction in the dose of an anti-cancer compound in a therapeutic anti-cancer regimen in combination with a synergistic composition of the present invention may also reduce the side effects of the anti-cancer compound.

In one embodiment of the dose of an anti-cancer compound present in a synergistic combination of the invention or used in an anti-cancer regimen may be reduced by about 2-fold, to about 100-fold. In one embodiment, the reduction in dose is about 2-, 3-, 4-, 5-, 6-, 7-, 8-, 9-, 10-, 20-, 30-, 40-, 50, 60-, 70-, 80-, 90-, or about 100-fold.

Subjects

Prophylactic and therapeutic methods of the present invention may be applied to any suitable subject. The methods herein include administering to the subject (including a subject identified as in need of such treatment) an effective amount of a composition as described herein to produce such effect.

Identifying a subject in need of such treatment can be in the judgment of a subject or a health care professional and can be subjective (e.g. opinion) or objective (e.g. measurable by a test or diagnostic method). In some embodiments, the subject is a mammalian subject. For example, the subject may be a mouse, rat, dog, cat, cow, sheep, horse or any other mammal of social, economic or research importance. Hence, the subject may be a mammal such as, for example, a human or a non-human mammal.

As outlined above, suitable subjects to be treated according to the methods described herein may be readily identified by the skilled addressee. Such subjects may include those who have been identified as having disease involving mucin, who have aberrant accumulation of mucinous material, and/or who have been diagnosed with a mucin secreting cancer. Further, the subjects may be further characterized using methods known to the skilled addressee and as described herein as having an accumulation of mucinous material having a semi-hard or hard consistency.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

Example 1. Effect of Combinations of Various Concentrations of Bromelain with Cysteamine on Mucinous Samples Obtained from Patients with Pseudomyxoma Peritonei (PMP)

Mucin samples from PMP patients were collected and stored under sterile conditions at −80° C. For experiments, the mucin was thawed to room temperature before use. One gram of soft mucin was transferred to a 50 ml centrifuge tube containing 10 ml of either 0.1 M TRIS buffer (pH. 7.0)—controls or similar arrangement containing various concentrations of cysteamine, bromelain or a mixture of the latter two reagents. The concentrations of bromelain investigated ranged from 100-300 µg/ml whilst for cysteamine it was 12.5, 25, 50, 100 and 200 mM. Stock solutions were prepared under sterile conditions in TRIS buffer pH adjusted to 7.0 using 0.1 M Sodium Hydroxide or 0.1 M Hydrochloric acid and the required quantities were added to the respective centrifuge tubes containing the mucin. The tubes were then transferred to a shaking water bath at 37° C. for 2 hours.

At the end of incubation, the remnant mucin was retrieved and weighed. The experiment was carried out using triplicate tubes and readings averaged. All experiments were performed in triplicate.

Bromelain (100, 200, 300 µg/ml) or Cysteamine (12.5-200 mM), as single agents only showed the mucin gaining weight, indicating hydration. On the other hand the addition of the two agents showed varying percentage of dissolution and at 50 mM cysteamine, the addition of either 100 or 200 µg/ml bromelain showed 100% disintegration. The addition of 300 µg/ml bromelain alone showed a reduction in hydration compared to the other controls indicating that both hydration and dissolution may be taking place. With the addition cysteamine (12.5-25 mM) a moderate disintegration (41-78%) was seen. However, with 50-200 mM cysteamine, all additions of bromelain (100, 200, 300 µg/ml) showed 100% disintegration. (Table 1, FIG. 1).

TABLE 1

Percentage Disintegration of Mucin Samples

| CIS (mM) | 0 µg/ml BR | +100 µg/ml BR | +200 µg/ml BR | +300 µg/ml BR |
|---|---|---|---|---|
| 0 | −95 | −79 | −88 | −63 |
| 12.5 | −117 | +20 | +25 | +53 |
| 25 | −115 | +41 | +53 | +60 |
| 50 | −100 | +100 | +100 | +64 |
| 100 | −111 | +100 | +100 | +100 |
| 200 | −86 | +100 | +100 | +100 |

Table 1 shows the gain in weight (−) negative disintegration or loss in weight (+) disintegration (values expressed as percentage disintegration). CIS=cysteamine; BR=Bromelain.

The addition of cysteamine or bromelain only shows hydration whilst the combination of both the agents shows variable disintegration. Complete disintegration is achieved at 2 hours/37° C. for 100 & 200 µg/ml bromelain with the addition of 50, 100, 200 mM cysteamine. In the case of 300 µg/ml bromelain, complete disintegration is only seen at 100, 200 mM cysteamine.

Further, the concentration (mM) of cysteamine required to achieve 50% disintegration of soft mucin decreases as the bromelain concentration increases showing that initial mucolysis proceeds fast at 300 µg/ml (Table 2, FIG. 1).

TABLE 2

Concentrations of Cysteamine and Bromelain required to achieve 50% and 100% disintegration of mucin samples.

| Bromelain (µg/ml) | 50% Disintegration at CIS Conc. (mM) | 100% Disintegration at CIS Conc. (mM) |
|---|---|---|
| 0 | — | — |
| 100 | 30 | 50 |
| 200 | 25 | 50 |
| 300 | 20 | 50 |

Figure 3:
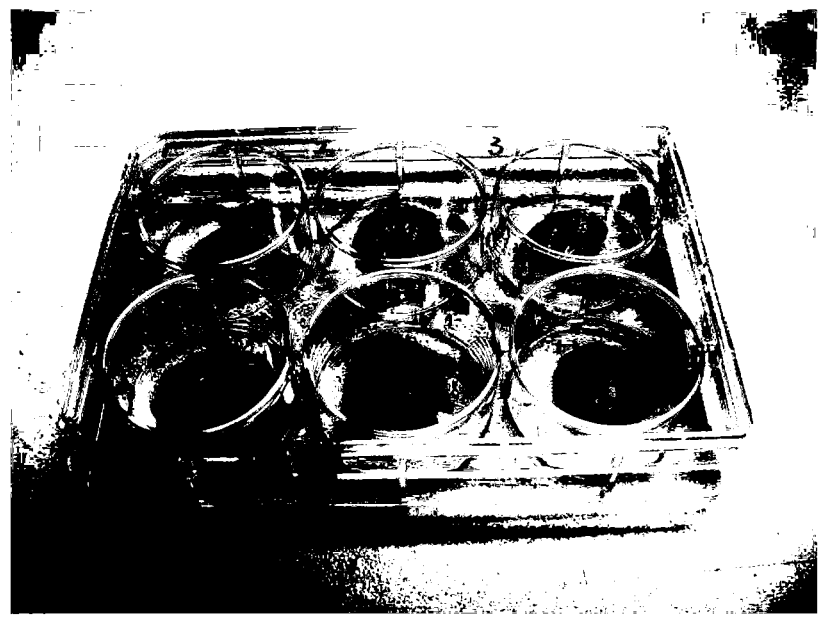
FIG. 3 shows the six soft mucin samples (1 g each) from six different PMP patients.
Figure 4:
FIG. 4 shows the six solubilized forms of the soft mucin that is readily amenable to suction with a catheter.

Similar is the case with addition of 100 or 200 µg/ml bromelain. For both 100 and 200 and 300 µg/ml bromelain, the addition of 50 mM cysteamine produces 100% dissolution of mucin. All the six patient soft mucin samples as shown in FIG. 3 were completely transformed to a free flowing liquid as shown in FIG. 4. Hence, 200 µg/ml bromelain+200 mM cysteamine was chosen for further investigation, since PMP mucin shows a wide variability in texture.

Example 2. Mucolytic Effect of a Combination of Bromelain (200n/ml)+200 mM Cysteamine on Six PMP Mucin Samples The combination of 200 µg/ml bromelain and 200 mM cysteamine was assessed on samples of soft mucinous material obtained from 6 different PMP patients.

To a 50 ml centrifuge tube containing 1 g of mucin was added 10 ml of TRIS pH. 7.0 containing 300 µg/ml bromelain+250 mM NAC. Similarly, to 1 g of mucin was added 10 ml of TRIS buffer containing 200 µg/ml bromelain+200 mM cysteamine. For each time interval (0.5, 1.0, 1.5, 2.0, 2.5 and 3.0 h), a total of 6 tubes in triplicate were prepared. The controls contained, TRIS, Bromelain (300 µg/ml & 200 µg/ml), NAC (250 mM) and Cysteamine (200 mM) with mucin (also prepared for each time interval, in triplicates).

Figure 5:
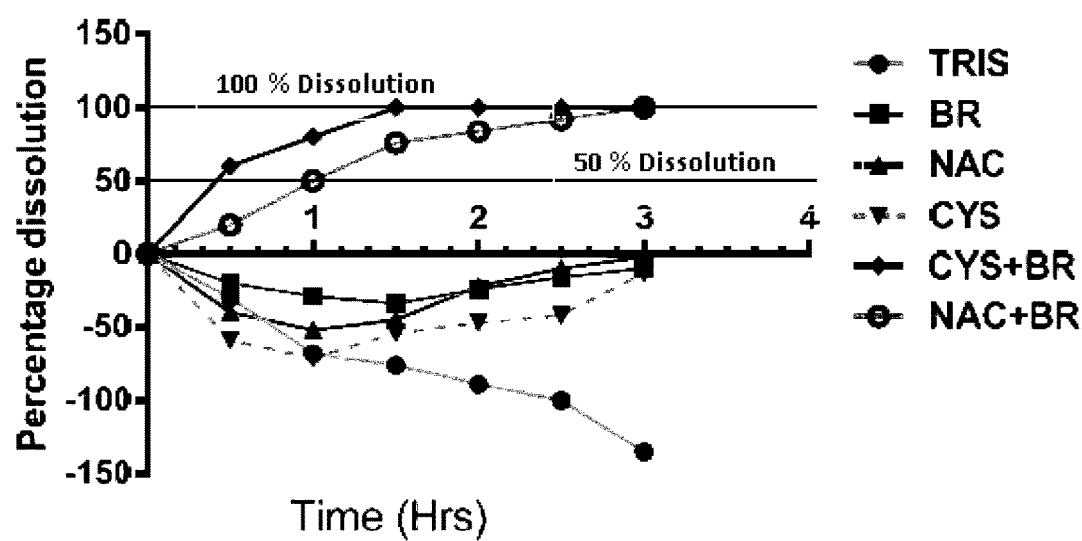
FIG. 5 shows a comparison of the time taken for disintegration of mucin secreted by Pseudomyxoma peritonei treated with 200 mM cysteamine (CYS) and 200 µg/ml bromelain (Br) or 250 mM N-acetyl cysteine (NAC)+bromelain 300 µg/ml.

The tubes were incubated at 37° C., in a shaker water bath, sample tubes were retrieved at time interval of 0.5 hour and remnant mucin was carefully retrieved and weighed. Percentage weight lost was calculated as follows:

Percentage weight lost (disintegration)=[mucin weight (at 0 hr)−mucin weight (2 or 3 hr)]/mucin weight (at 0 hr). The combination of 300 µg/ml bromelain with 250 mM N-acetyl cysteine or 200 µg/ml bromelain and 200 mM cysteamine showed disintegration (FIG. 5), however, cysteamine with bromelain showed accelerated disintegration (100% disintegration at 1.5 hours) compared to NAC with bromelain that took 3 hours (twice as long).

Individual agents such as Bromelain, NAC and cysteamine only showed hydration initially, with subsequent slight disintegration and hydration. At three hours, all the individual agents, except IRIS showed no gain in weight.

The time taken for 50% disintegration for cysteamine+Bromelain was 25 minutes whilst for NAC+Bromelain, it was 60 minutes.

Example 3. Comparison of Disintegration of Different Grades of PMP Mucin (Soft, Semi Hard and Hard) Treated with 200 μg/ml Bromelain+200 mM Cysteamine or 300 μg/ml Bromelain+250 mM N-Acetyl Cysteine for Three Hours Approximately 1 g of mucin sample was placed on a Petri dish and inspected for its firmness and transparency. To classify mucin definitively into grades of hardness, 1 g of mucin was carefully weighed and then soaked in 10 ml of distilled water at ambient room temperature (21° C.) for 30 minutes. The hydrated mucin was removed and placed to rest on a gridded glass slab (mm square gridding). The gridded glass slab was prepared by placing a square transparent glass (1.0 mm thickness) on the top of a 1.0 mm$^2$ gridded paper. The area that the mucin occupied after 1 minute on the gridded glass was traced, and using standard formula, the area was calculated.

A hardness index (HI) was calculated as: Weight of mucin (g)/Area mucin occupies on glass grid slab (mm$^2$). Mucin samples were characterized as soft, semi-hard or hard where the sample was transparent, semi-opaque or opaque, respectively, and/or wherein the mucin was determined to have a hardness index of ≤0.6, >0.6-1.2, or >1.2, respectively.

The experimental set up was similar to that as described in Example 2; however, the disintegration time was extended 3 hours. At the end of 2 hours samples were retrieved and weighed, similarly at end of three hours samples were retrieved and weighed again.

Figure 6:
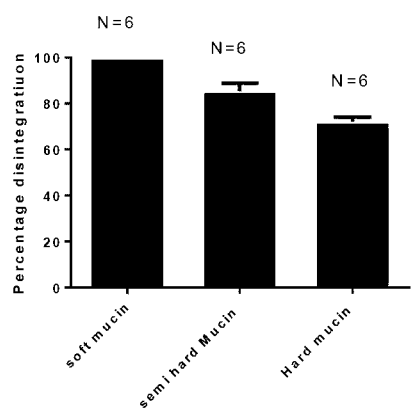
FIG. 6 shows the percentage disintegration of the three grades of, mucin (soft, semi hard and hard) when treated with 200 mM cysteamine+200 µg/ml bromelain (A) or 250 mM NAC+300 µs/ml bromelain (B) for 2 hours, or 200 mM cysteamine+200 µg/ml bromelain or 250 mM NAC+300 µg/ml bromelain for 3 hours (C and D, respectively).
Figure 6:
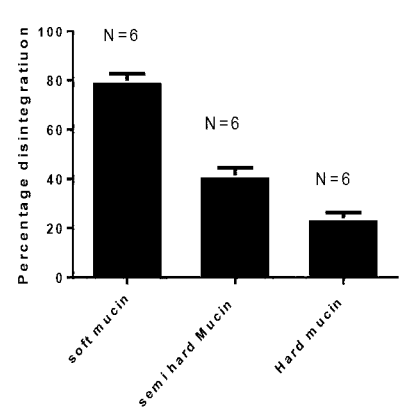
Figure 6:
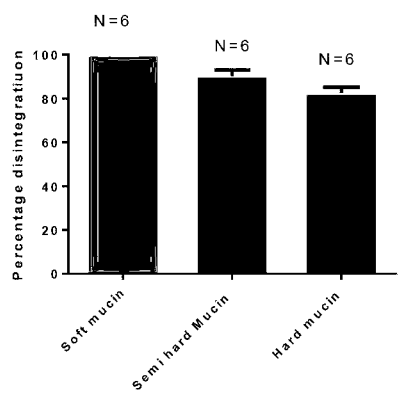
Figure 6:
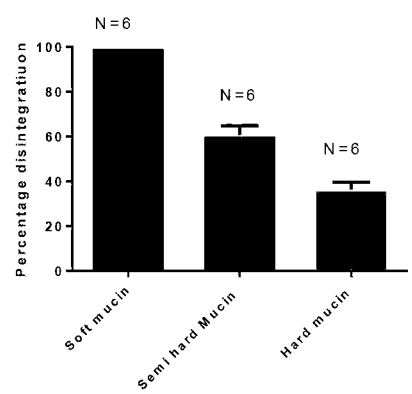

Soft mucin treated with 200 μg/ml bromelain+200 mM cysteamine produced 100% dissolution within 2 hours, however only 89 and 72.6% was observed for both semi soft and hard mucin, respectively, during the 2 hours (Table 3, FIG. 6). At 3 hours the dissolution increased to 94 and 86% for both the semi hard and hard mucin, respectively (P>0.05 vs soft mucin). This is an important observation, since the semi hard mucin was almost completely disintegrated whilst only 14% of the hard original mucin was left. On the other hand 300 μg/ml bromelain+250 mM NAC was only able to achieve 84% dissolution of soft mucin within 2 hours with a much reduced mucolytic efficacy for semi hard (46%) and hard mucin (26%). Whilst at the 3 hour time point complete dissolution of soft mucin was observed, only 64% disintegration of semi hard mucin and only 40% disintegration of hard mucin was observed. These results demonstrate that compared to the combination of NAC and bromelain, the addition of 200 mM cysteamine to 200 μg/ml bromelain is a much more effective mucolytic.

TABLE 3

Percentage disintegration of PMP mucin at time intervals (2 & 3 hours) from the three grades of mucin.

| MUCIN TYPE | % Disintegration (Cysteamine (200 mM) + Bromelain (200 μg/ml)) | | % Disintegration (N-acetyl cysteine (250 mM) + Bromelain (300 μg/ml)) | |
|---|---|---|---|---|
| | 2 hrs | 3 hrs | 2 hrs | 3 hrs |
| Soft Mucin (SM) | 100% | 100% | 84% | 100% |
| Semi-Hard Mucin (SHM) | 89% | 94% | 46% | 64% |
| Hard Mucin (HM) | 72.6% | 86% | 26% | 40% |

Figure 7:
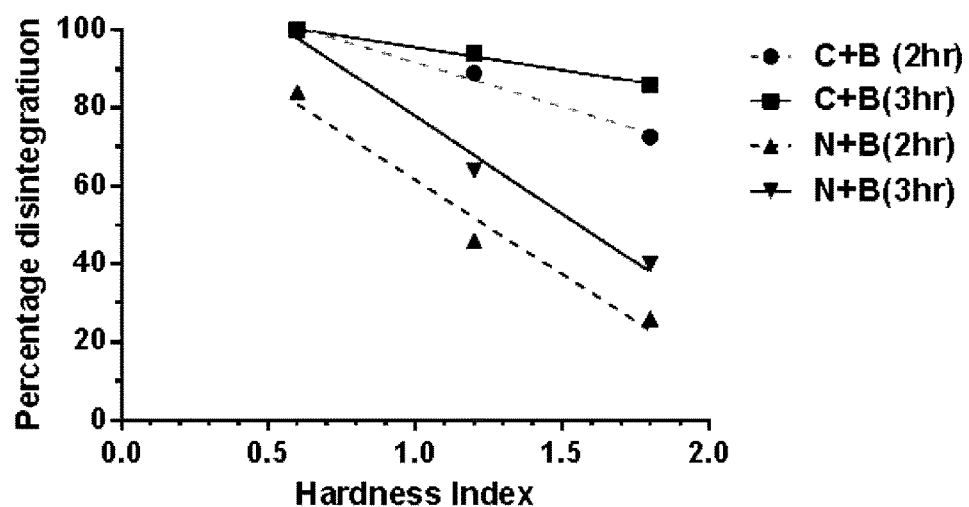
FIG. 7 shows the percentage disintegration of the three grades of mucin classified according to hardness index (HI), soft mucin, HI=0.6, semi hard mucin, HI=1.2 and hard mucin, HI=1.8, with two different incubation time (2 vs 3 hrs). C+B=200 mM cysteamine+200 µg/ml bromelain; N+B=250 mM N-acetyl cysteine+300 µg/ml bromelain.
Figure 8:
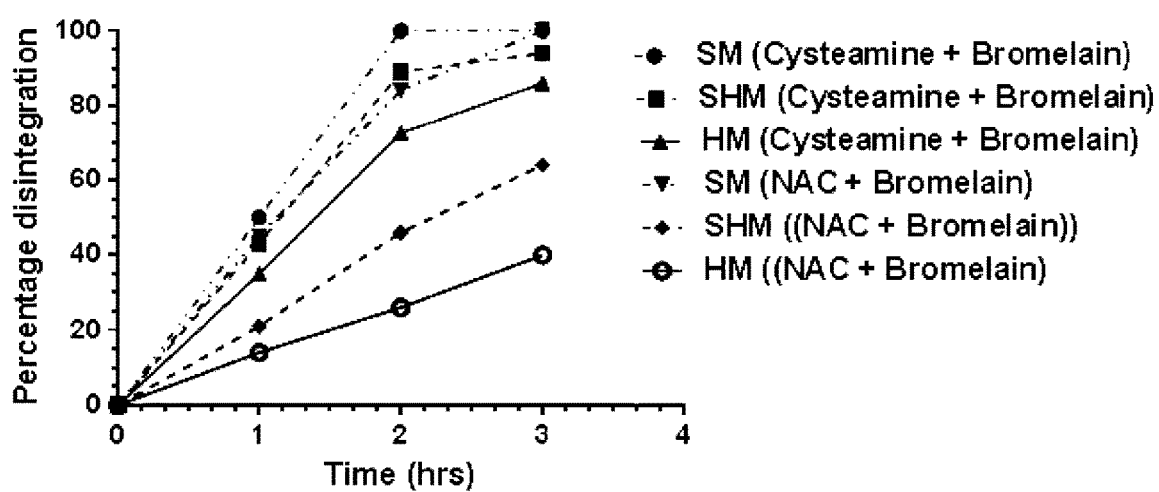
FIG. 8 shows the time (hours) taken for the three grades of mucin to have a 50% and a 100% disintegration when treated with 200 mM cysteamine+200 µg bromelain or 250 mM N-acetyl cysteine+300 µg/ml bromelain. SM=soft mucin; SHM=semi hard mucin; HM=hard mucin.

As demonstrated in FIG. 7 an inverse relationship exists between the hardness index of mucin and the percentage disintegration. Table 4 shows analysis of the data represented in FIG. 7:

TABLE 4

Data analysis for FIG. 7.

| Best-fit values | C + B (2 hr) | C + B(3 hr) | N + B(2 hr) | N + B(3 hr) |
|---|---|---|---|---|
| Slope | −22.83 ± 2.598 | −11.67 ± 0.9623 | −48.33 ± 8.660 | −50.00 ± 5.774 |
| Y-intercept when X = 0.0 | 114.6 ± 3.367 | 107.3 ± 1.247 | 110.0 ± 11.22 | 128.0 ± 7.483 |
| X-intercept when Y = 0.0 | 5.019 | 9.200 | 2.276 | 2.560 |
| 1/slope | −0.04380 | −0.08571 | −0.02069 | −0.0200 |

Comparison of the 200 mM cysteine+200 μg/ml bromelain group (2 hours) with that of similar treated group over 3 hours, it is apparent that the disintegration is more effective for the semi hard and hard mucin as depicted by the comparison of slope of the graph (22.83/11.67=1.95). On the other hand for the NAC+bromelain treatment, a comparison again shows that over two hours the disintegration was less compared to 3 hours (48.33/50=0.967). This further shows that disintegration variability using cysteamine+bromelain over 2 hrs compared to 3 hours was greater for the semi hard and hard mucin, whilst in the case of NAC+bromelain, the variability of time dependent disintegration existed for all the three grades of mucin with 3 hours having better disintegration.

TABLE 5

Time taken by each type of mucin to attain 50% disintegration and the rate of disintegration in minutes.

| Mucin Type | Cysteamine + Bromelain | | NAC + Bromelain | |
|---|---|---|---|---|
| | Time (h) | weight lost (mg)/min | Time (h) | Weight lost (mg)/min |
| Soft (SM) | 1 hr | 8.33 | 1 hr 10 mins | 7.15 |
| Semi hard (SHM) | 1 hr 10 min | 7.14 | 2 hr 10 mins | 3.85 |
| Hard (HM) | 1 hr 23 mins | 6.02 | >3 hrs | <2.77 |

TABLE 6

Time taken by each type of mucin to attain 50% disintegration and the rate of disintegration in minutes.

| Mucin Type | Cysteamine + Bromelain | | NAC + Bromelain | |
|---|---|---|---|---|
| | Time (h) | weight lost (mg)/min | Time (h) | Weight lost (mg)/min |
| Soft (SM) | 1 hr | 8.33 | 1 hr 50 mins | 4.54 |
| Semi hard (SHM) | 1 hr 50 min | 4.0 | 50 mins | 2.8 |
| Hard (HM) | 1 hr 37 mins | 3.71 | >3 hrs | <2.77 |

Further analysis of the time taken and the disintegration rate of the different mucin types classified according to their hardness index indicates that 200 mM cysteamine+300 µg/ml bromelain disintegrates the three types of mucin more readily (based on the disintegration rate and time to disintegrate) (Table 5) as compared to the use of 250 mM NAC+300 µg/ml bromelain. More noticeably, the disintegration of the remaining 50% mucin for soft mucin proceeds at the same rate as for the first 50% disintegration, when using cysteamine and bromelain Table 6). For the semi hard and hard mucin the rate of disintegration is half that of the first 50% disintegration.

In the case of bromelain+NAC, the rate of disintegration of the latter 50% of soft mucin was reduced by 37%, and 28% for semi hard whilst for the hard mucin it was very slow during the 3 hours of study and not even 50% disintegration was achieved.

The 50% disintegration time for both NAC and cysteamine on PMP mucin varies linearly as hardness increases (FIG. 9), however for cysteamine+bromelain group, the variation is small as compared to the NAC+bromelain group. This indicates that cysteamine+bromelain is a more efficient mucolytic since it is capable of acting quite equally on all mucin types. However, this is not the case with NAC+bromelain indicating that the hardness of the mucin affects disintegration of mucin dramatically.

TABLE 7

Figure 9:
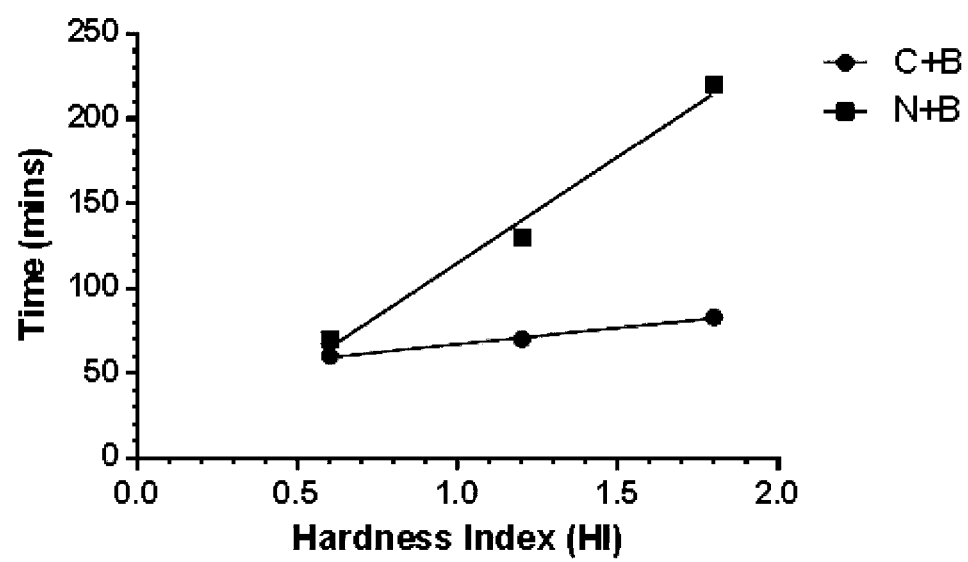
FIG. 9 shows the variation in time for 50% disintegration in the three grades of PMP mucin when subjected to 200 mM cysteamine+200 µg/ml bromelain (C+B) or 250 mM NAC+300 µg/ml bromelain. (N+B)

Analysis of FIG. 9.

| Best-fit values | C + B | N + B |
|---|---|---|
| Slope | 19.17 ± 1.443 | 125.0 ± 14.43 |
| Y-intercept when X = 0.0 | 48.00 ± 1.871 | −10.00 ± 18.71 |
| X-intercept when Y = 0.0 | −2.504 | 0.08000 |
| 1/slope | 0.05217 | 0.008000 |

On a comparative basis the effect of hardness is almost about 6.5 times (125/19.17) greater in 250 mM NAC+300 µg/ml bromelain compared to 200 mM cysteamine+200 µg/ml bromelain.

Example 4. Further Optimization of Bromelain+Cysteamine to Reduce Concentration of Both the Agents Used to Disintegrate Soft Mucin The experiment was set up as outlined above in Examples 1 and 2 above, however using 10, 20, 40, 60, 80 & 100 µg/ml bromelain with varying concentrations of cysteamine (10, 20, 30, 40 & 50 mM) and the incubation was carried out at 37° C. in a shaker for 3 hours. The controls contained TRIS buffer, 10, 20, 40, 60, 80 & 100 µg/ml bromelain and 10, 20, 30, 40 & 50 mM cysteamine. Each tube was prepared in triplicate and readings averaged.

When soft mucin was treated to low concentration of bromelain (10-100 µg/ml) with cysteamine (20-50 mM), cysteamine at 20 mM is able to only disintegrate a 100% of mucin at 100 mM bromelain. Similarly the addition of 30 or 40 mM cysteamine, a 100% disintegration of mucin was observed at only 60 µg/ml bromelain. However, with 50 mM cysteamine addition to 40 µg/ml bromelain, complete disintegration of mucin was observed (Table 5, FIG. 10 A).

TABLE 8

Various combinations of bromelain with cysteamine at which a 100% mucin disintegration is observed.

| Cysteamine (mM) | Bromelain (µg/ml) |
|---|---|
| 20 | 100 |
| 30 | 60 |
| 40 | 60 |
| 50 | 40 |

Example 5. Comparison of Mucolytic Efficacy of 50 mM Cysteamine+50 µg/ml Bromelain on PMP Mucin Experiments were set up as before using 1 g of mucin in a 50 ml centrifuge tube containing either TRIS buffer (pH 7.0), 50 µg/ml bromelain, 50 mM cysteamine or a combination of the last two agents. Six samples from each grades of mucin (soft, semi-hard and hard) were chosen for the experiment and the tubes were incubated in a shaker water bath at 37° C. for duration of 3 hours. The remnant mucin were carefully retrieved and weighed.

Figure 10:
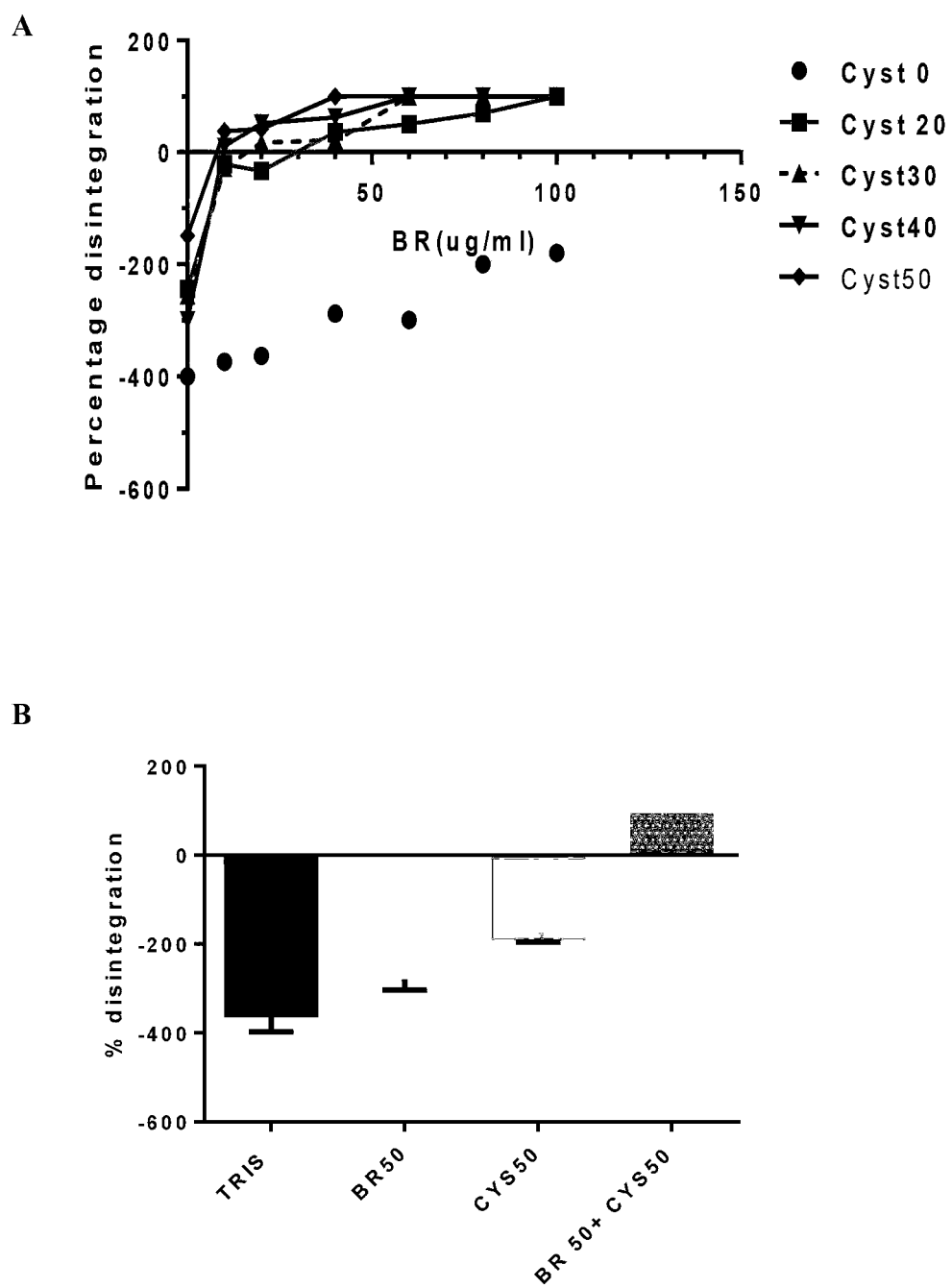
FIG. 10 shows disintegration of mucin when treated with bromelain, cysteamine or a combination thereof for 3 hours at 37° C. (A) Comparison of various combinations of bromelain and cysteamine on the disintegration of soft mucin. (B) Disintegration of soft mucin when subjected to 50 mM cysteamine+50 µg/ml bromelain; (C) Disintegration of semi-hard mucin when subjected to 50 mM cysteamine+50 µg/ml bromelain. (D) Disintegration of hard mucin when subjected to 50 mM cysteamine+50 µg/ml bromelain.
Figure 10:
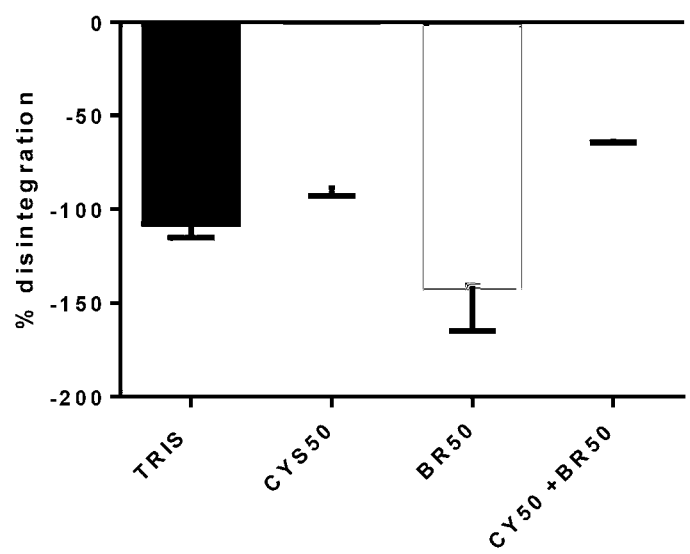
Figure 10:
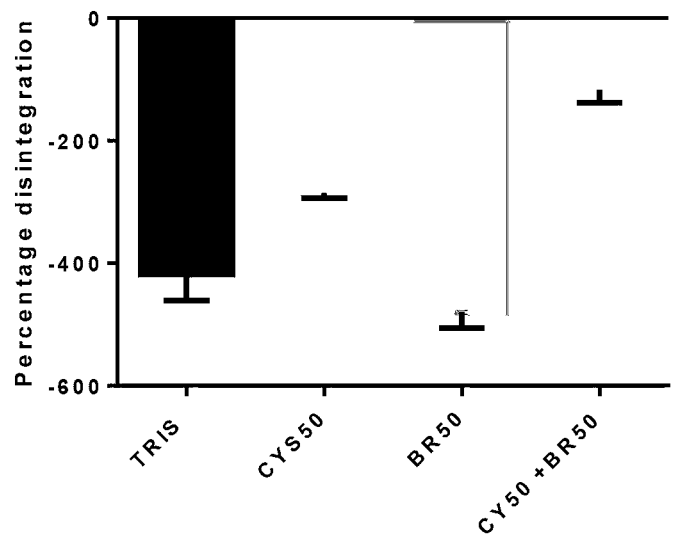

Treatment with low concentration of cysteamine (50 mM)+Bromelain (50 µg/ml) at 37° C. for 3 hours indicated that a 100% of all soft mucin were disintegrated, however, individual agents only showed varying degree of hydration, as indicated by a gain in weight (FIG. 10 B). TRIS showed a higher degree of hydration compared to either bromelain or cysteamine. The lower weight gain as compared to TRIS may indicate that in addition to hydration, some disintegration occurs.

A similar treatment on the semi hard mucin indicated that hydration was lower in the treatment groups of TRIS, bromelain and cysteamine, when compared to soft mucin. This may be due to the composition of the mucin that caused some disintegration as well as hydration with individual agents such as bromelain or cysteamine whilst showing least hydration with the combination of the two agents owing to loss of mucin through disintegration (FIG. 10 C).

In the case of hard mucin a dramatic percentage of hydration took place particularly with TRIS buffer and cysteamine whilst a combination of bromelain and cysteamine produced hydration slightly greater than 100% (FIG. 10 D).

Example 6. In Vitro Simulation of Peritoneal Wash with Time Taken to Disintegrate Mucin Further optimization of the minimum concentrations of bromelain and cysteamine to be used in combination for the disintegration of soft, semi-hard or hard mucin may be undertaken using an in vitro simulation of a peritoneal wash. According to such a simulation, a mass of mucin (5 g) is carefully deposited into a 100 ml or 250 ml beaker that has an inflowing and out flowing tube that is connected to a reservoir containing 100 ml of mucolytic (50 µg/ml bromelain+50 mM cysteamine in TRIS buffer, pH. 7.0). Using a pump, the mucolytic is circulated so that the mucin is completely soaked in the mucolytic with circulation at 37° C. The time to completely disintegrate six different samples from each of three grades of mucin is recorded. Controls will be carried out using TRIS buffer, 50 μg/ml bromelain and 50 mM cysteamine.

Example 7. Effect of Combinations of Various Concentrations of Bromelain with Cysteamine on Mucin Secreting Cancer Cells Proliferation Assay 5000 cells of each cell line were plated in 96 well plates and grown for 48 hrs at 37° C. in humidified $CO_2$ incubator. After this the medium was replaced with drugs, bromelain, cysteamine and cisplatin in alone or in various combinations. Control wells had medium only. Plates were further incubated for 72 hrs. At the end of incubation proliferation was determined by SRB assay.

SRB Assay

Materials and Method:
0.4% (w/v) SRB: 1.0 g SRB— Sulforhodamine B sodium salt—(#S1402, SIGMA) in 250 ml of 1% acetic acid (stored at room temperature)
10% (w/v) TCA: 50 g of Trichloroacetic acid (#T9159, SIGMA) in 500 ml of Milli-Q water (stored at 4° c.)
10 mM Tris Base: 0.6055 g Tris (Trizma® base, #T6066, SIGMA) in 500 ml of Milli-Q water (stored at 4° c.)
1% acetic acid: 10 ml of acetic acid in 1000 ml of Milli-Q water.

1. After an incubation period of 72 hours, the old medium was discarded and cells were fixed with 200 μl of 10% (w/v) ice-cold TCA (trichloroacetic acid) for 30 minutes at 4° C.
2. The plate was washed in distilled water 5 times.
3. 100 μl of 0.4% (w/v) sulphorhodamine (SRB) solution was added to each well of the dry 96-well plates and they were allowed staining at room temperature for 10 mins.
4. The sulphorhodamine (SRB) solution was removed by washing the plate repeatedly (5 times) with 1% (v/v) acetic acid, to remove unbound dye and then the 96-well plate was allowed to dry in the air (overnight).
5. The protein-bound dye (SRB) was dissolved in 10 mM Tris base solution (100 μl/well) after shaking for 20 minutes on a shaker platform.
6. The plate was read in a microplate reader (Power-WaveX, BIO-TEK instruments, Inc, USA) with the working wavelength 570 nm.

Figure 11:
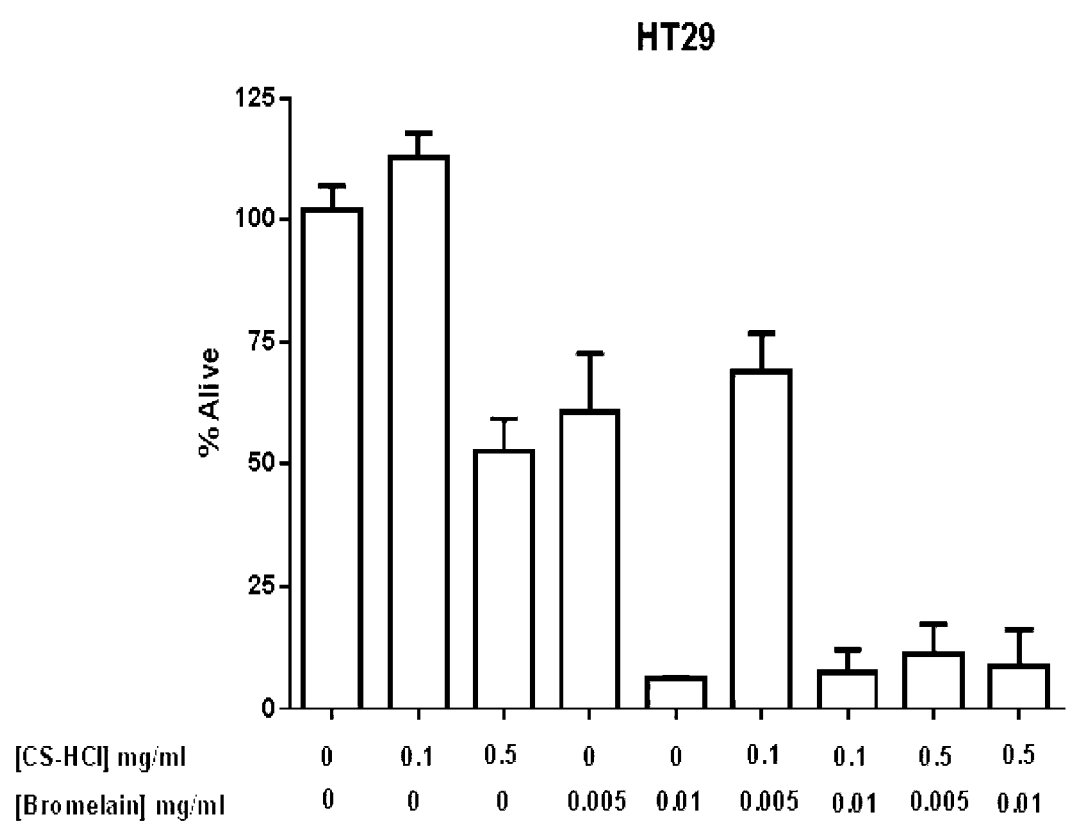
FIG. 11 shows the results of a viability assay demonstrating the effect of the combination of CYS and Br on the in vitro growth of HT29 colorectal cancer cells.

H129 is a colorectal cancer cell line, which secretes gastric type mucin. The effect of CYS, Br and the combination on in vitro growth (SRB assay, 72 hour culture) was studied. FIG. 11 shows these results expressed as % of control. CYS and Br individually had no or little effect, whereas combinations of concentrations of CYS and Br which were ineffective produced up to 90% inhibition of growth.

Figure 12:
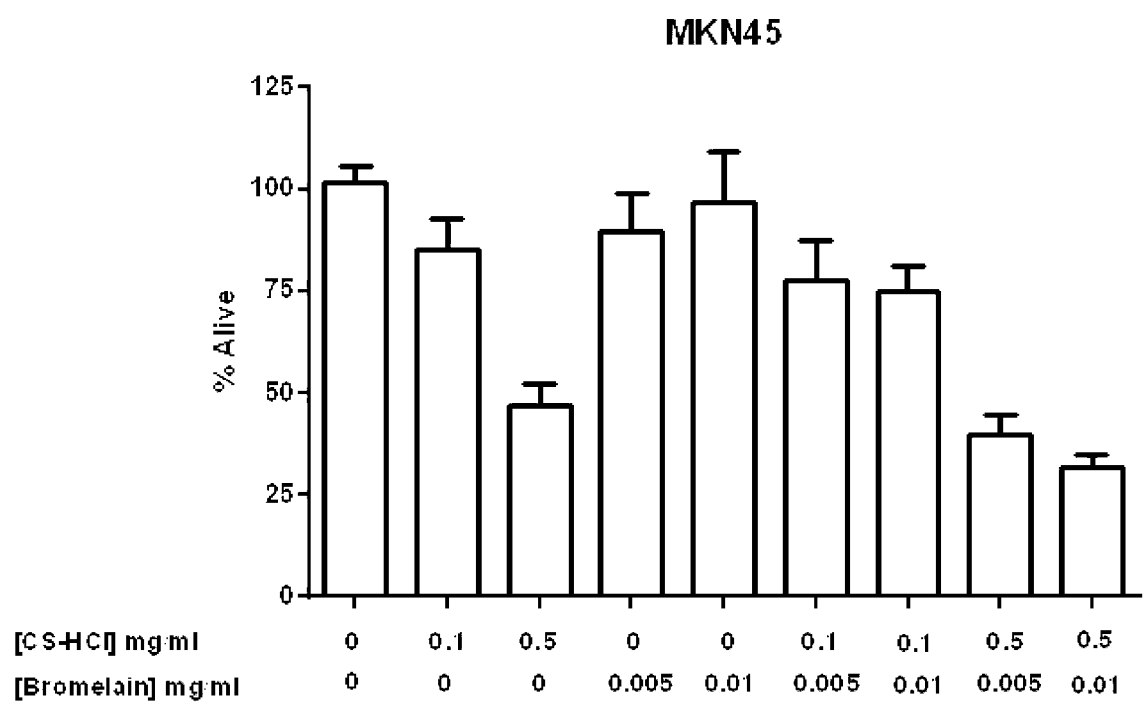
FIG. 12 shows the results of a viability assay demonstrating the effect of the combination of CYS and Br on the in vitro growth of MKN45 gastric cancer cells.

MKN 45 is a human gastric mucin secreting cancer cell line. The effect of CYS, Br and the combination on in vitro growth (SRB assay, 72 hour culture) was studied. FIG. 12 shows these results expressed as % of control. Again CYS and Br individually had no or little effect, whereas the combination of CYS and Br at the highest concentrations tested displayed a synergistic effect.

Figure 23:
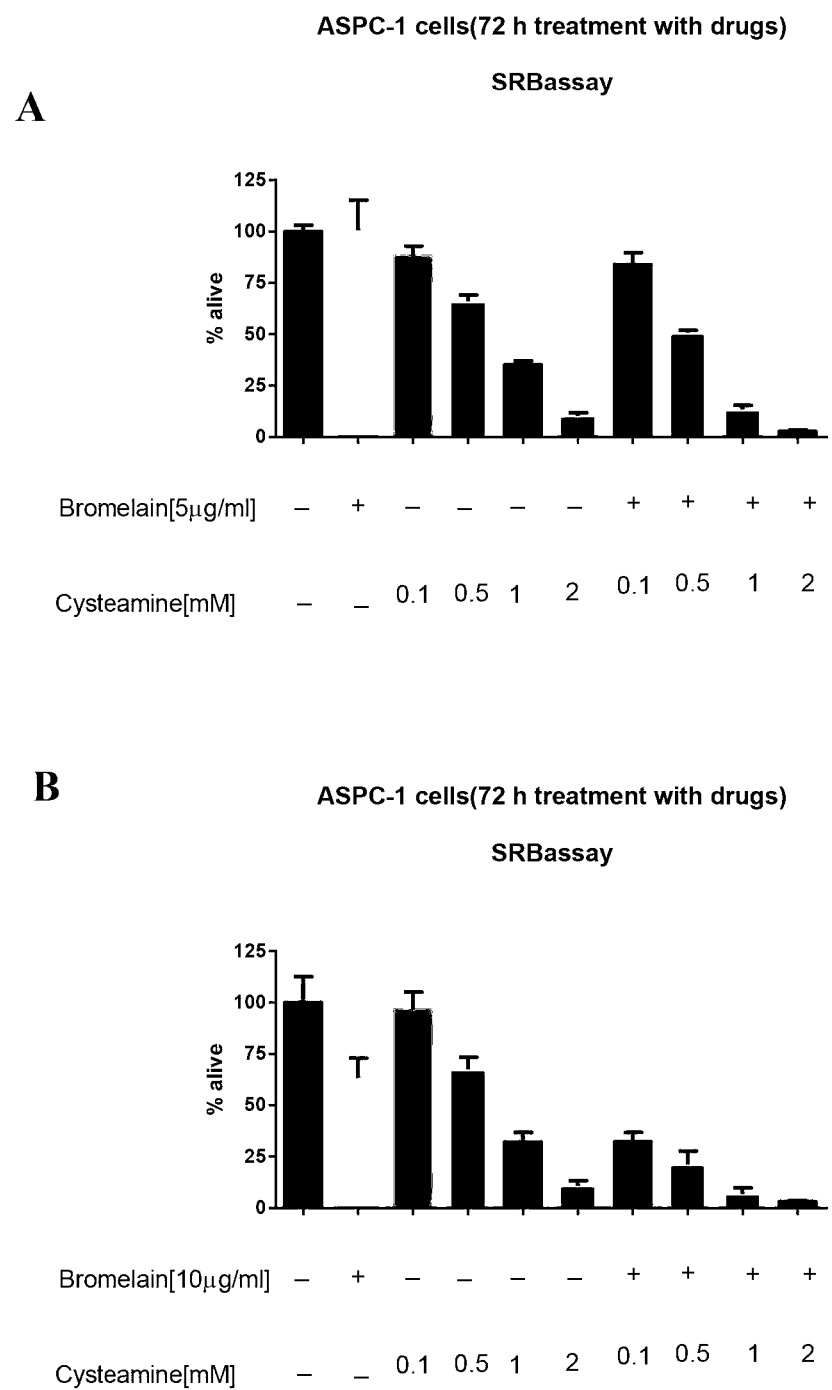
FIG. 23 shows the effect of the combination of different concentrations of Cysteamine and 5 µg/ml of bromelain (A) and 10 µg/ml bromelain (B) on viability of human pancreatic cell line ASPC-1.

AsPC-1 is a cell line which produces abundant mucin. The cell line was derived from ascites of a patient with pancreatic cancer. The effect of CYS, Br and the combination on in vitro growth (SRB assay, 72 hour culture) was studied. FIG. 23 shows these results expressed as % of control for two different concentrations of Br. Data are represented as mean±SD (6 replicates for each treatment group).

Statistical analysis for FIGS. 23 A and B is presented in Table 9A and 9B, respectively, wherein columns from left to right correspond to columns A-J. (e.g. in FIG. 23A, Column A=control, Column B=Bromelain 5 μg/ml, etc.).

TABLE 9A

Statistical analysis for AsPC-1 (Cysteamine 0.1 – 2 mM + Bromelain 5 μg/ml):

| Holm-Sidak's multiple comparisons test | Mean Diff. | Significant? | Summary | Adjusted P Value |
|---|---|---|---|---|
| Column A vs. Column B | −0.6185 | No | ns | 0.9205 |
| Column A vs. Column C | 11.96 | Yes | ** | 0.0046 |
| Column A vs. Column D | 33.98 | Yes | *** | 0.0004 |
| Column A vs. Column E | 64.74 | Yes | **** | <0.0001 |
| Column A vs. Column F | 89.65 | Yes | **** | <0.0001 |
| Column A vs. Column G | 15.97 | Yes | ** | 0.0027 |
| Column A vs. Column H | 49.30 | Yes | **** | <0.0001 |
| Column A vs. Column I | 86.59 | Yes | **** | <0.0001 |
| Column A vs. Column J | 97.20 | Yes | **** | <0.0001 |
| Column B vs. Column C | 12.58 | No | ns | 0.2444 |
| Column B vs. Column D | 34.60 | Yes | ** | 0.0078 |
| Column B vs. Column E | 65.36 | Yes | ** | 0.0019 |
| Column B vs. Column F | 90.27 | Yes | *** | 0.0005 |
| Column B vs. Column G | 16.59 | No | ns | 0.1487 |
| Column B vs. Column H | 49.91 | Yes | ** | 0.0046 |
| Column B vs. Column I | 87.21 | Yes | *** | 0.0007 |
| Column B vs. Column J | 97.81 | Yes | *** | 0.0003 |
| Column C vs. Column D | 22.02 | Yes | ** | 0.0037 |
| Column C vs. Column E | 52.78 | Yes | **** | <0.0001 |
| Column C vs. Column F | 77.69 | Yes | **** | <0.0001 |
| Column C vs. Column G | 4.007 | No | ns | 0.2444 |
| Column C vs. Column H | 37.33 | Yes | *** | 0.0002 |
| Column C vs. Column I | 74.63 | Yes | **** | <0.0001 |
| Column C vs. Column J | 85.23 | Yes | **** | <0.0001 |
| Column D vs. Column E | 30.76 | Yes | **** | <0.0001 |
| Column D vs. Column F | 55.67 | Yes | **** | <0.0001 |
| Column D vs. Column G | −18.01 | Yes | ** | 0.0075 |
| Column D vs. Column H | 15.32 | Yes | ** | 0.0027 |
| Column D vs. Column I | 52.62 | Yes | **** | <0.0001 |
| Column D vs. Column J | 63.22 | Yes | **** | <0.0001 |
| Column E vs. Column F | 24.91 | Yes | **** | <0.0001 |
| Column E vs. Column G | −48.77 | Yes | *** | 0.0002 |
| Column E vs. Column H | −15.44 | Yes | *** | 0.0004 |
| Column E vs. Column I | 21.85 | Yes | **** | <0.0001 |
| Column E vs. Column J | 32.46 | Yes | **** | <0.0001 |
| Column F vs. Column G | −73.68 | Yes | **** | <0.0001 |
| Column F vs. Column H | −40.35 | Yes | **** | <0.0001 |
| Column F vs. Column I | −3.057 | No | ns | 0.1016 |
| Column F vs. Column J | 7.545 | Yes | ** | 0.0012 |
| Column G vs. Column H | 33.33 | Yes | *** | 0.0004 |
| Column G vs. Column I | 70.62 | Yes | **** | <0.0001 |
| Column G vs. Column J | 81.23 | Yes | **** | <0.0001 |
| Column H vs. Column I | 37.30 | Yes | **** | <0.0001 |
| Column H vs. Column J | 47.90 | Yes | **** | <0.0001 |
| Column I vs. Column J | 10.60 | Yes | *** | 0.0009 |

TABLE 9B

Statistical analysis for AsPC-1 (Cysteamine 0.1 – 2 mM + Bromelain 10 μg/ml):

| Holm-Sidak's multiple comparisons test | Mean Diff. | Significant? | Summary | Adjusted P Value |
|---|---|---|---|---|
| Column A vs. Column B | 36.64 | Yes | * | 0.0116 |
| Column A vs. Column C | 3.541 | No | ns | 0.7901 |
| Column A vs. Column D | 32.52 | Yes | * | 0.0142 |
| Column A vs. Column E | 67.75 | Yes | *** | 0.0009 |
| Column A vs. Column F | 89.13 | Yes | *** | 0.0003 |
| Column A vs. Column G | 67.65 | Yes | *** | 0.0003 |
| Column A vs. Column H | 78.69 | Yes | ** | 0.0013 |

TABLE 9B-continued

Statistical analysis for AsPC-1 (Cysteamine 0.1 – 2 mM + Bromelain 10 µg/ml):

| Holm-Sidak's multiple comparisons test | Mean Diff. | Significant? | Summary | Adjusted P Value |
|---|---|---|---|---|
| Column A vs. Column I | 92.92 | Yes | *** | 0.0003 |
| Column A vs. Column J | 96.84 | Yes | *** | 0.0003 |
| Column B vs. Column C | −33.10 | Yes | *** | 0.0001 |
| Column B vs. Column D | −4.121 | No | ns | 0.2299 |
| Column B vs. Column E | 31.11 | Yes | ** | 0.0015 |
| Column B vs. Column F | 52.49 | Yes | *** | 0.0010 |
| Column B vs. Column G | 31.01 | Yes | ** | 0.0029 |
| Column B vs. Column H | 42.06 | Yes | ** | 0.0036 |
| Column B vs. Column I | 56.28 | Yes | *** | 0.0009 |
| Column B vs. Column J | 60.20 | Yes | *** | 0.0006 |
| Column C vs. Column D | 28.98 | Yes | *** | 0.0002 |
| Column C vs. Column E | 64.21 | Yes | **** | <0.0001 |
| Column C vs. Column F | 85.59 | Yes | *** | 0.0001 |
| Column C vs. Column G | 64.11 | Yes | **** | <0.0001 |
| Column C vs. Column H | 75.15 | Yes | *** | 0.0005 |
| Column C vs. Column I | 89.38 | Yes | *** | 0.0001 |
| Column C vs. Column J | 93.30 | Yes | **** | <0.0001 |
| Column D vs. Column E | 35.23 | Yes | *** | 0.0002 |
| Column D vs. Column F | 56.61 | Yes | *** | 0.0002 |
| Column D vs. Column G | 35.13 | Yes | *** | 0.0003 |
| Column D vs. Column H | 46.18 | Yes | ** | 0.0014 |
| Column D vs. Column I | 60.40 | Yes | *** | 0.0001 |
| Column D vs. Column J | 64.32 | Yes | **** | <0.0001 |
| Column E vs. Column F | 21.38 | Yes | ** | 0.0020 |
| Column E vs. Column G | −0.09900 | No | ns | 0.9545 |
| Column E vs. Column H | 10.94 | No | ns | 0.0828 |
| Column E vs. Column I | 25.17 | Yes | ** | 0.0020 |
| Column E vs. Column J | 29.09 | Yes | *** | 0.0006 |
| Column F vs. Column G | −21.48 | Yes | ** | 0.0019 |
| Column F vs. Column H | −10.44 | Yes | * | 0.0305 |
| Column F vs. Column I | 3.787 | Yes | * | 0.0305 |
| Column F vs. Column J | 7.710 | Yes | ** | 0.0094 |
| Column G vs. Column H | 11.04 | No | ns | 0.1274 |
| Column G vs. Column I | 25.27 | Yes | ** | 0.0011 |
| Column G vs. Column J | 29.19 | Yes | *** | 0.0005 |
| Column H vs. Column I | 14.22 | Yes | * | 0.0197 |
| Column H vs. Column J | 18.15 | Yes | * | 0.0116 |
| Column I vs. Column J | 3.923 | No | ns | 0.0828 |

Figure 24:
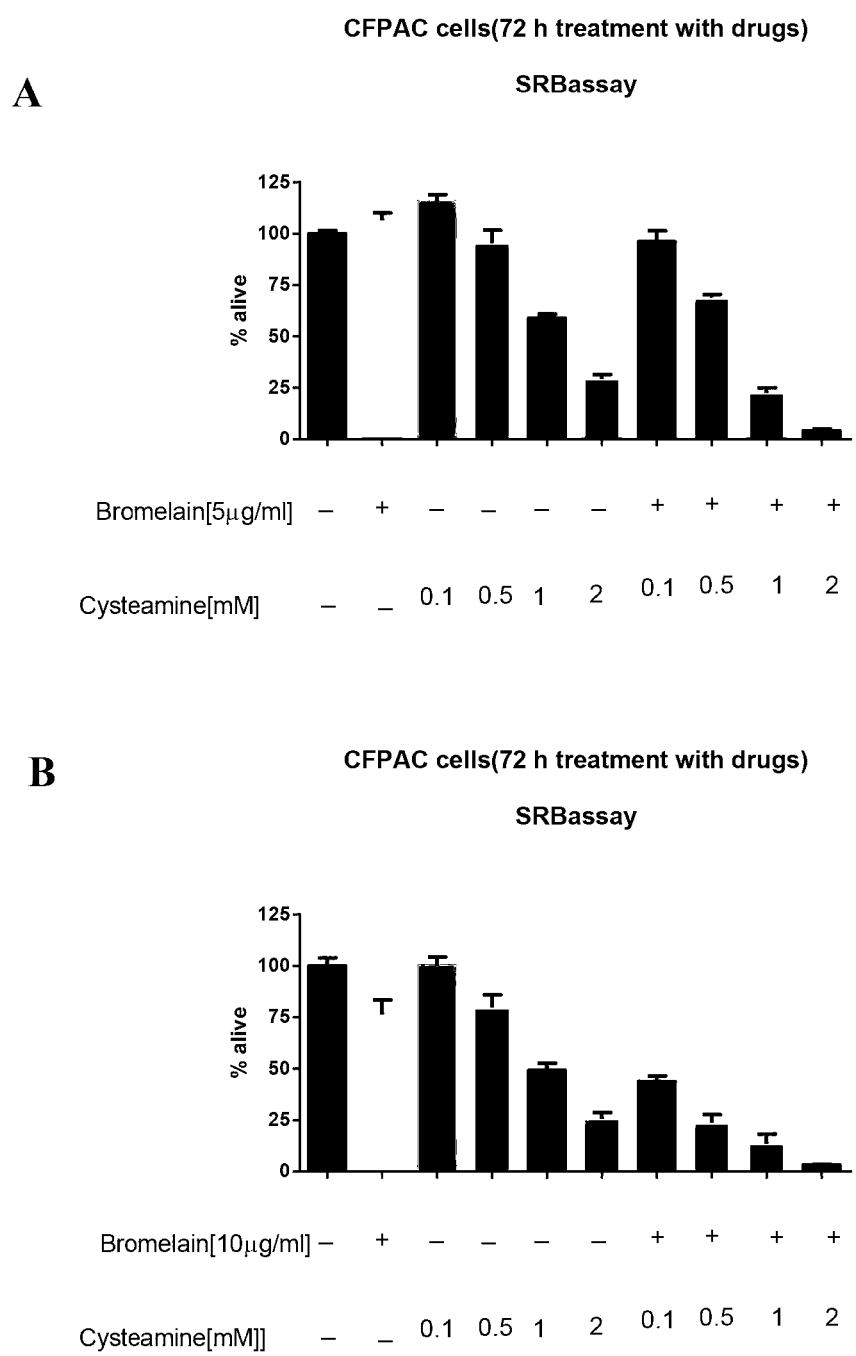
FIG. 24 shows the effect of the combination of different concentrations of Cysteamine and 5 µg/ml of bromelain (A) and 10 µg/ml bromelain (B) on viability of human pancreatic cell line CFPAC.
Figure 25:
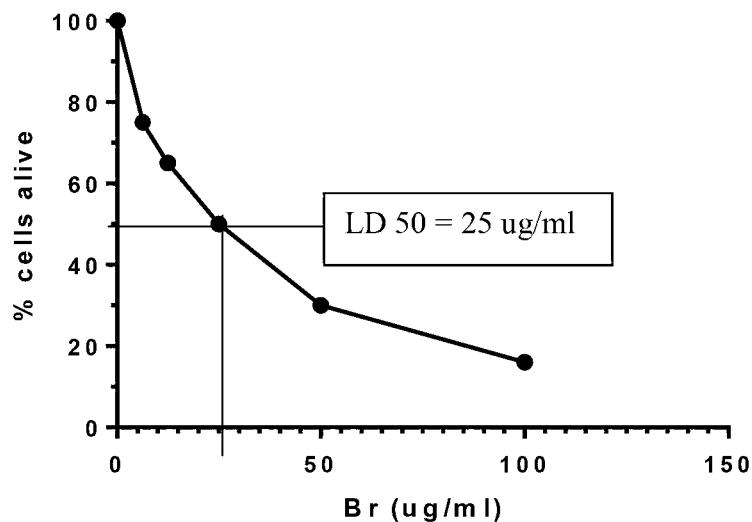
FIG. 25 shows the effect of bromelain (A), Cysteamine (B) or Cisplatin (C) on viability of human pancreatic cell line ASPC-1.
Figure 25:
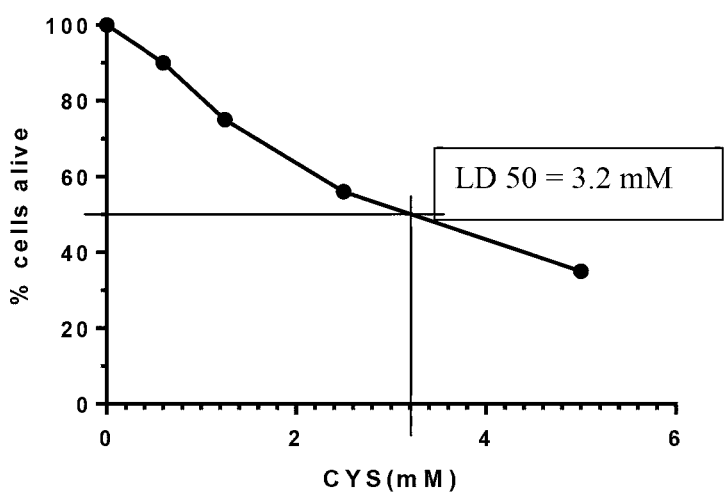
Figure 25:
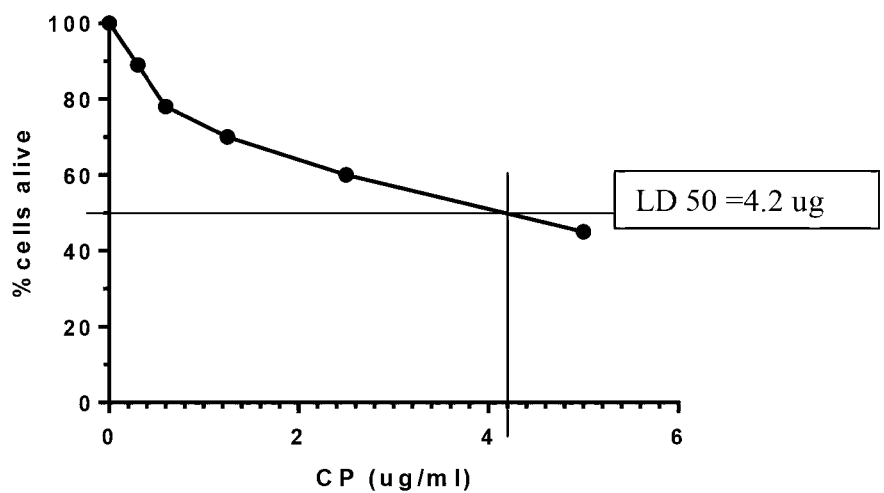
Figure 26:
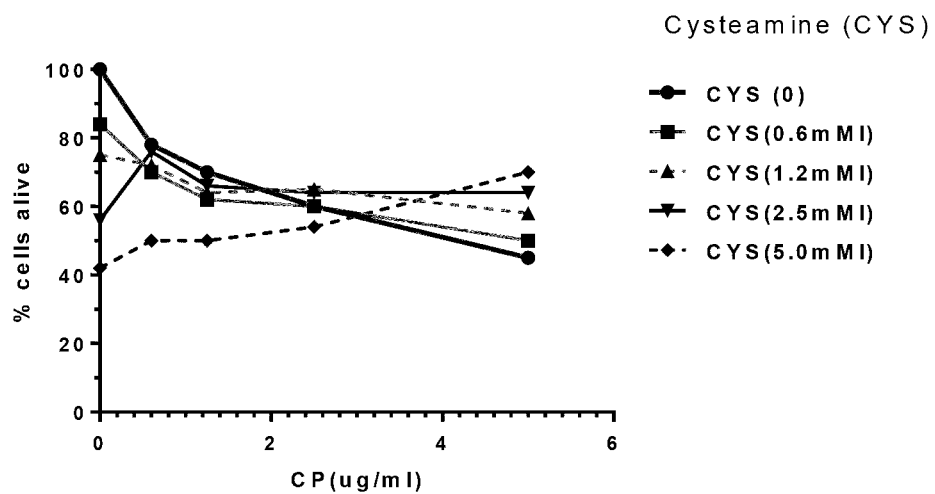
FIG. 26 shows the effect of the combination of different concentrations of Cysteamine and Cisplatin on viability of human pancreatic cell line ASPC-1.
Figure 27:
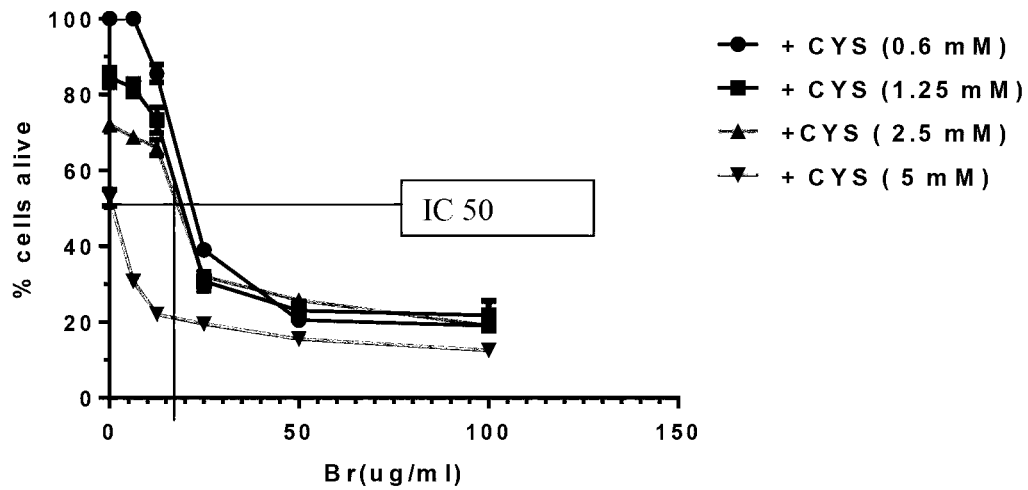
FIG. 27 shows the effect of the combination of different concentrations of Cysteamine and Bromelain on viability of human pancreatic cell line ASPC-1.
Figure 28:
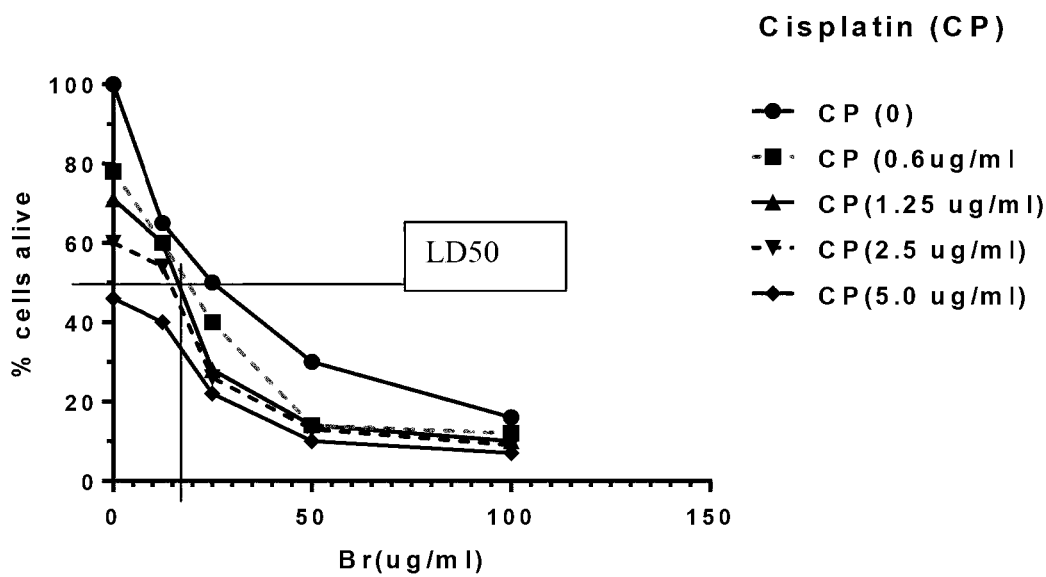
FIG. 28 shows the effect of the combination of different concentrations of Cisplatin and Bromelain on viability of human pancreatic cell line ASPC-1.
Figure 29:
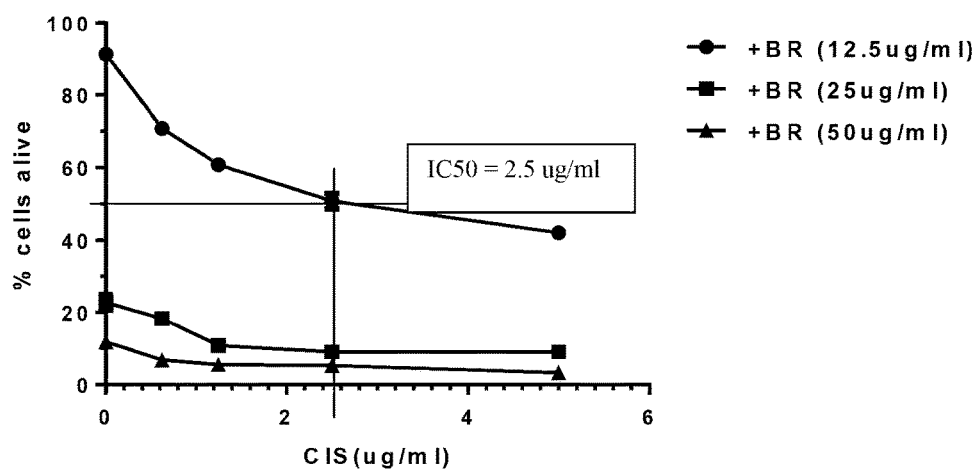
FIG. 29 shows the results of a viability assays (A), (B) and (C) demonstrating the effect of different concentrations of Cysteamine+Bromelain+Cisplatin in combination on the in vitro growth of human pancreatic cell line ASPC-1.
Figure 29:
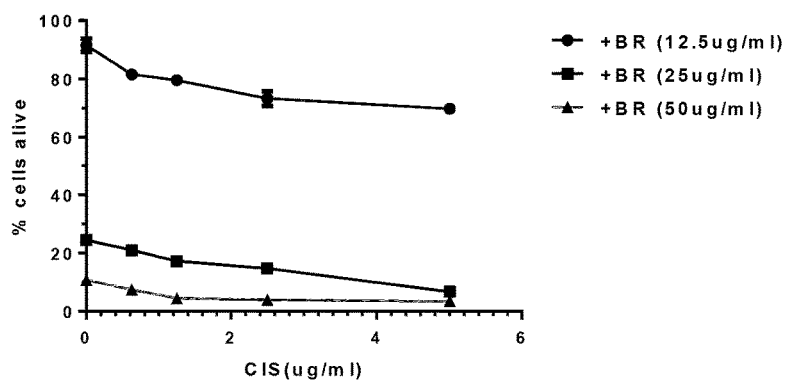
Figure 29:
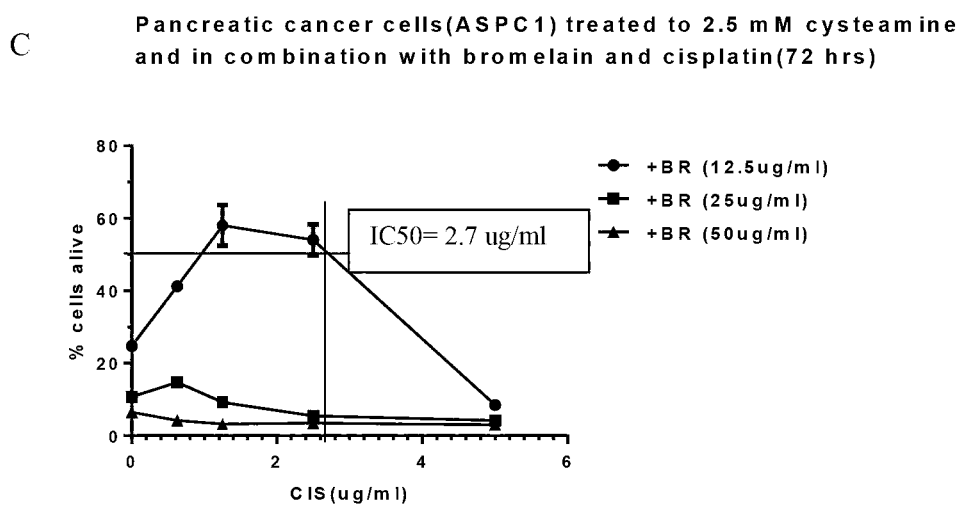

CFPAC is a pancreatic cancer cell line derived from a patient with cystic fibrosis which also secretes abundant mucin. The effect of CYS, Br and the combination on in vitro growth (SRB assay, 72 hour culture) was studied. FIG. 24 shows these results expressed as % of control for two different concentrations of Br. Data are represented as mean±SD (6 replicates for each treatment group).

Statistical analysis for FIGS. 24 A and B is presented in Table 10A and 10B, respectively, wherein columns from left to right correspond to A-J. (e.g. in FIG. 24 A, Column A=control, Column B=Bromelain 5 µg/ml, etc.).

TABLE 10A

Statistical analysis for CFPAC (Cysteamine 0.1 – 2 mM + Bromelain 5 µg/ml):

| Holm-Sidak's multiple comparisons test | Mean Diff. | Significant? | Summary | Adjusted P Value |
|---|---|---|---|---|
| Column A vs. Column B | −6.470 | Yes | ** | 0.0050 |
| Column A vs. Column C | −15.79 | Yes | **** | <0.0001 |
| Column A vs. Column D | 4.522 | No | ns | 0.0604 |
| Column A vs. Column E | 40.95 | Yes | **** | <0.0001 |
| Column A vs. Column F | 70.53 | Yes | **** | <0.0001 |
| Column A vs. Column G | 3.756 | No | ns | 0.1021 |
| Column A vs. Column H | 30.96 | Yes | **** | <0.0001 |
| Column A vs. Column I | 77.34 | Yes | **** | <0.0001 |
| Column A vs. Column J | 95.87 | Yes | **** | <0.0001 |
| Column B vs. Column C | −9.321 | Yes | **** | <0.0001 |
| Column B vs. Column D | 10.99 | Yes | **** | <0.0001 |

TABLE 10A-continued

Statistical analysis for CFPAC (Cysteamine 0.1 – 2 mM + Bromelain 5 µg/ml):

| Holm-Sidak's multiple comparisons test | Mean Diff. | Significant? | Summary | Adjusted P Value |
|---|---|---|---|---|
| Column B vs. Column E | 47.42 | Yes | **** | <0.0001 |
| Column B vs. Column F | 77.00 | Yes | **** | <0.0001 |
| Column B vs. Column G | 10.23 | Yes | **** | <0.0001 |
| Column B vs. Column H | 37.43 | Yes | **** | <0.0001 |
| Column B vs. Column I | 83.81 | Yes | **** | <0.0001 |
| Column B vs. Column J | 102.3 | Yes | **** | <0.0001 |
| Column C vs. Column D | 20.31 | Yes | **** | <0.0001 |
| Column C vs. Column E | 56.74 | Yes | **** | <0.0001 |
| Column C vs. Column F | 86.32 | Yes | **** | <0.0001 |
| Column C vs. Column G | 19.55 | Yes | **** | <0.0001 |
| Column C vs. Column H | 46.76 | Yes | **** | <0.0001 |
| Column C vs. Column I | 93.13 | Yes | **** | <0.0001 |
| Column C vs. Column J | 111.7 | Yes | **** | <0.0001 |
| Column D vs. Column E | 36.43 | Yes | **** | <0.0001 |
| Column D vs. Column F | 66.01 | Yes | **** | <0.0001 |
| Column D vs. Column G | −0.7662 | No | ns | 0.6870 |
| Column D vs. Column H | 26.44 | Yes | **** | <0.0001 |
| Column D vs. Column I | 72.82 | Yes | **** | <0.0001 |
| Column D vs. Column J | 91.34 | Yes | **** | <0.0001 |
| Column E vs. Column F | 29.58 | Yes | **** | <0.0001 |
| Column E vs. Column G | −37.19 | Yes | **** | <0.0001 |
| Column E vs. Column H | −9.986 | Yes | **** | <0.0001 |
| Column E vs. Column I | 36.39 | Yes | **** | <0.0001 |
| Column E vs. Column J | 54.91 | Yes | **** | <0.0001 |
| Column F vs. Column G | −66.77 | Yes | **** | <0.0001 |
| Column F vs. Column H | −39.57 | Yes | **** | <0.0001 |
| Column F vs. Column I | 6.811 | Yes | ** | 0.0036 |
| Column F vs. Column J | 25.33 | Yes | **** | <0.0001 |
| Column G vs. Column H | 27.21 | Yes | **** | <0.0001 |
| Column G vs. Column I | 73.59 | Yes | **** | <0.0001 |
| Column G vs. Column J | 92.11 | Yes | **** | <0.0001 |
| Column H vs. Column I | 46.38 | Yes | **** | <0.0001 |
| Column H vs. Column J | 64.90 | Yes | **** | <0.0001 |
| Column I vs. Column J | 18.52 | Yes | **** | <0.0001 |

TABLE 10B

Statistical analysis for CFPAC (Cysteamine 0.1 – 2 mM + Bromelain 10 µg/ml):

| Holm-Sidak's multiple comparisons testcc | Mean Diff. | Significant? | Summary |
|---|---|---|---|
| Column A vs. Column B | 23.46 | Yes | ** |
| Column A vs. Column C | −0.1145 | No | ns |
| Column A vs. Column D | 20.13 | Yes | ** |
| Column A vs. Column E | 50.66 | Yes | **** |
| Column A vs. Column F | 74.34 | Yes | **** |
| Column A vs. Column G | 56.06 | Yes | **** |
| Column A vs. Column H | 76.24 | Yes | **** |
| Column A vs. Column I | 86.45 | Yes | **** |
| Column A vs. Column J | 96.78 | Yes | **** |
| Column B vs. Column C | −23.57 | Yes | ** |
| Column B vs. Column D | −3.329 | No | ns |
| Column B vs. Column E | 27.20 | Yes | ** |
| Column B vs. Column F | 50.89 | Yes | *** |
| Column B vs. Column G | 32.61 | Yes | ** |
| Column B vs. Column H | 52.78 | Yes | *** |
| Column B vs. Column I | 63.00 | Yes | *** |
| Column B vs. Column J | 73.32 | Yes | **** |
| Column C vs. Column D | 20.24 | Yes | *** |
| Column C vs. Column E | 50.77 | Yes | **** |
| Column C vs. Column F | 74.46 | Yes | **** |
| Column C vs. Column G | 56.18 | Yes | *** |
| Column C vs. Column H | 76.35 | Yes | **** |
| Column C vs. Column I | 86.57 | Yes | **** |
| Column C vs. Column J | 96.89 | Yes | **** |
| Column D vs. Column E | 30.53 | Yes | *** |
| Column D vs. Column F | 54.21 | Yes | **** |
| Column D vs. Column G | 35.94 | Yes | ** |
| Column D vs. Column H | 56.11 | Yes | *** |

TABLE 10B-continued

Statistical analysis for CFPAC (Cysteamine 0.1 – 2 mM + Bromelain 10 µg/ml):

| Holm-Sidak's multiple comparisons testcc | Mean Diff. | Significant? | Summary |
|---|---|---|---|
| Column D vs. Column I | 66.33 | Yes | *** |
| Column D vs. Column J | 76.65 | Yes | **** |
| Column E vs. Column F | 23.69 | Yes | *** |
| Column E vs. Column G | 5.408 | No | ns |
| Column E vs. Column H | 25.58 | Yes | ** |
| Column E vs. Column I | 35.80 | Yes | *** |
| Column E vs. Column J | 46.12 | Yes | **** |
| Column F vs. Column G | −18.28 | Yes | ** |
| Column F vs. Column H | 1.894 | No | ns |
| Column F vs. Column I | 12.11 | Yes | * |
| Column F vs. Column J | 22.43 | Yes | *** |
| Column G vs. Column H | 20.17 | Yes | *** |
| Column G vs. Column I | 30.39 | Yes | **** |
| Column G vs. Column J | 40.71 | Yes | **** |
| Column H vs. Column I | 10.22 | Yes | ** |
| Column H vs. Column J | 20.54 | Yes | *** |
| Column I vs. Column J | 10.32 | Yes | * |

These findings show that the combination of Br and CYS has highly significant inhibition effects on different cancer cell lines growth, when they had little if any effect on their own.

Example 7. Effect of Bromelain, Cysteamine and Cisplatin, on Cancer Cell Viability Mesothelioma (YOU and PET), gastric (KATO-III), Colorectal (LS174T and HT295m21), pancreatic (ASPC-1 and CFPAC) and ovarian (A2780) cell lines were grown in RPMI supplemented with 10% FBS, 100 U/ml penicillin and 100 µg/ml streptomycin. All cells were maintained at 37° C.

The cytotoxic effects of cysteamine, bromelain and the chemotherapeutic agent cisplatin were assessed. Each agent was administered to the cells either alone or in combination with either or both of the other agents. All cells were treated for 72 hours with the reagents and the cell populations were assessed using the SRB assay. Where possible, $IC_{50}$ and $IC_{max}$ were calculated.

These studies demonstrate a synergistic anti-cancer effect for compositions comprising a combination of cysteamine and bromelain, and optionally cisplatin.

The data generated for studies performed on YOU and PET cells are summarized in Table 11.

TABLE 11

Effect of bromelain, cysteamine and cisplatin, on cancer cell viability

| Agents | YOU CELLS | | PET CELLS | |
|---|---|---|---|---|
| | IC50 | ICmax | IC50 | ICmax |
| +Bromelain (single agent) | 10 µg/ml Br | 86% at 200 µg/ml Br | 40 µg/ml Br | 80% at 200 µg/ml Br |
| +Cysteamine (single agent) | 0.56 mg/ml Cysteamine | 94% at 11.3 mg/ml Cysteamine | 0.781 mg/ml Cysteamine | 85% at 11.3 mg/ml cysteamine |
| Bromelain + Cysteamine | | | | |
| Bromelain + 1.412 mg/ml | — | 100% at 200 µg/ml Br | — | 100% at 200 µg/ml Br |
| Bromelain + 0.706 mg/ml | — | 92% at 200 µg/ml Br | 6.25 | 95% at 200 µg/ml Br |
| Bromelain + 0 | 10 µg/ml Br | 85% at 200 µg/ml Br | 40 µg/ml Br | 78% at 200 µg/ml Br |
| Cysteamine + Cisplatin NOT COMPATIBLE Bromelain + Cisplatin | — | — | — | — |
| 0-100 µg/ml + 0.3 µg/ml | — | 90% | — | 88% |
| 0-100 µg/ml + 0.15 µg/ml | 5.0 µg/ml Br | 88% | 55 µg/ml Br | 72% |
| 0-100 µg/ml + 0.075 µg/ml | 25 µg/ml Br | 75% | 85 µg/ml Br | 70% |
| 0-100 µg/ml + 0.0375 µg/ml | 65 µg/ml Br | 60% | 85 µg/ml Br | 65% |
| 0-100 µg/ml + 0 µg/ml | 10 µg/ml Br | 86% | 40 µg/ml Br | 80% |
| BR (0-100 µg/ml) + 5.65 mg/ml Cysteamine + Cisplatin (CPL) | | | | |
| 0.3 µg/ml | — | 100% (at 80 µg/ml Br) | — | 100%(at 100% µg/ml Br) |
| 0.15 µg/ml | — | 100% (100 µg/ml Br) | — | 92% (at 100 µg/ml Br) |
| 0.075 µg/ml | — | 94% (100 µg/ml Br) | — | 87% (at 100 µg/ml Br) |
| 0.0375 µg/ml | — | 80% (100 µg/ml Br) | — | 80% (at 100 µg/ml Br) |
| 0 µg/ml | — | | — | |
| BR (0-100 µg/ml) + 2.82 mg/ml Cysteamine + Cisplatin (CPL) | | | | |
| 0.3 µg/ml | — | 100% (at 100 µg/ml Br) | — | 100% (at 100 µg/ml Br) |
| 0.15 µg/ml | — | 100% (at 100 µg/ml Br) | — | 93% (at 100 µg/ml Br) |
| 0.075 µg/ml | — | 94% (at 100 µg/ml Br) | — | 89% (at 100 µg/ml Br) |
| 0.0375 µg/ml | — | 90% (at 100 µg/ml Br) | — | 85% (at 100 µg/ml Br) |
| 0 µg/ml | — | 80% (at 100 µg/ml Br) | — | 86% (at 100 µg/ml Br) |
| BR (0-100 µg/ml) + 1.42 mg/ml | | | | |

TABLE 11-continued

Effect of bromelain, cysteamine and cisplatin, on cancer cell viability

| Agents | YOU CELLS | | PET CELLS | |
|---|---|---|---|---|
| | IC50 | ICmax | IC50 | ICmax |
| Cysteamine + Cisplatin (CPL) | | | | |
| 0.3 µg/ml | — | 88% (at 100 µg/ml Br) | — | 90% (at 100 µg/ml Br) |
| 0.15 µg/ml | — | 89% (at 100 µg/ml Br)- | — | 85% (at 100 µg/ml Br) |
| 0.075 µg/ml | — | 72% (at 100 µg/ml Br) | — | 84% (at 100 µg/ml Br) |
| 0.0375 µg/ml | — | 65% (at 100 µg/ml Br) | — | 76% (at 100 µg/ml Br) |
| 0 µg/ml | 20 µg/ml Br | 72% (at 100 µg/ml Br) | 22 µg/ml Br | 74% (at 100 µg/ml Br) |

Figure 13:
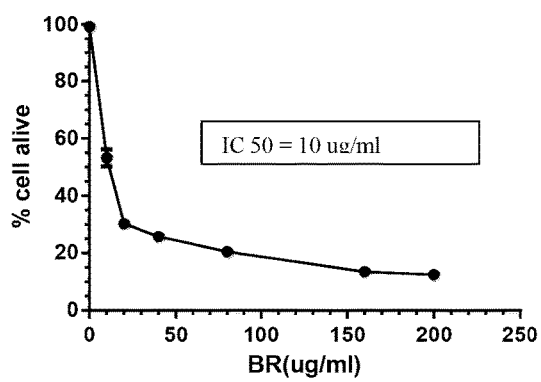
FIG. 13 shows the results of a viability assay demonstrating the effect of the bromelain (Br) or cysteamine (CYS) on the in vitro growth of YOU mesothelioma cells (A) and (B), respectively, and the effect of Br and Cys on PET mesothelioma cells (C) and (D), respectively.
Figure 13:
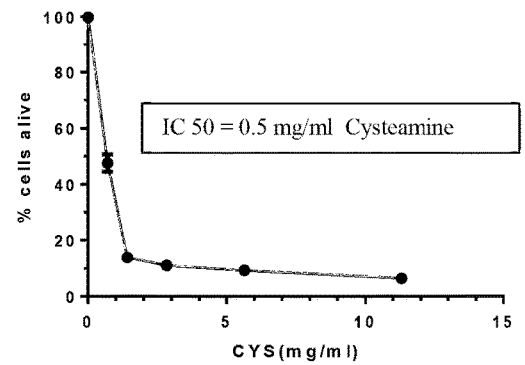
Figure 13:
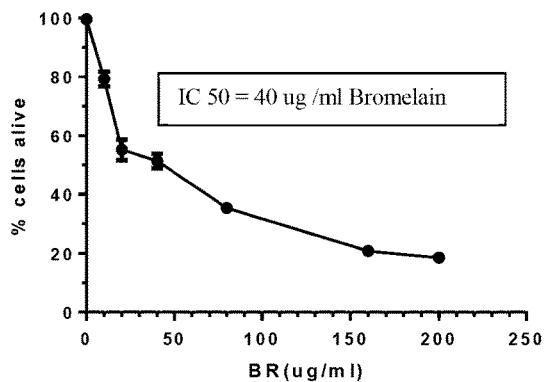
Figure 13:
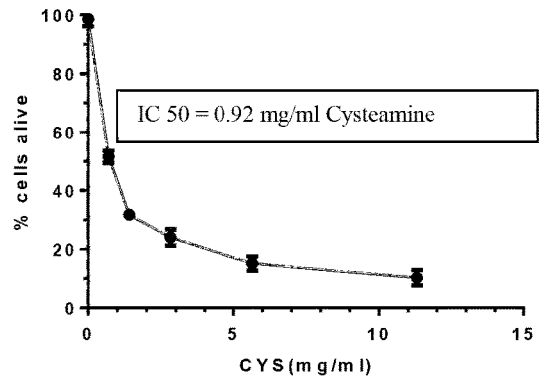
Figure 14:
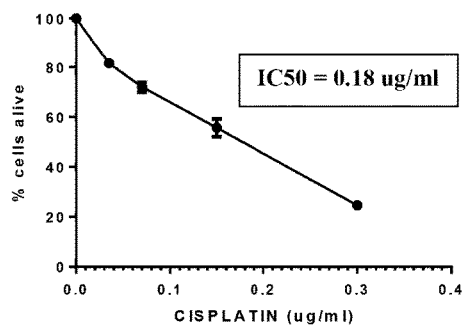
FIG. 14 shows the results of a viability assay demonstrating the effect of the Cisplatin on the in vitro growth of YOU and PET mesothelioma cells (A) and (B) respectively and the combined effects of the combination of cysteamine (CYS) on the in vitro growth of YOU and PET mesothelioma cells, (C) and (D), respectively.
Figure 14:
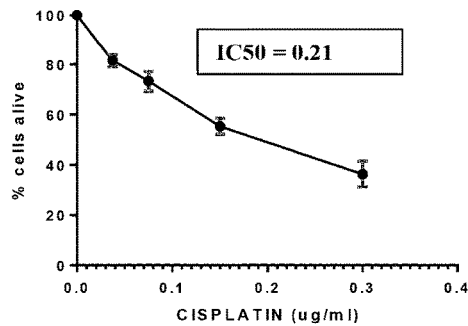
Figure 14:
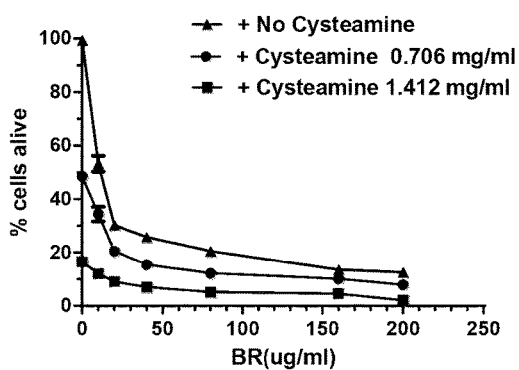
Figure 14:
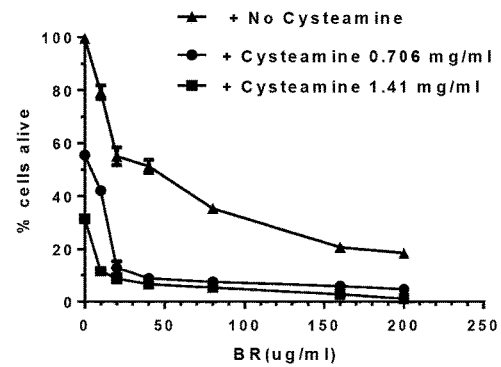

FIGS. 13, 14 (A and B) show the results each agent assessed in isolation. At low concentrations of bromelain, co-treatment with cysteamine showed enhanced cytotoxicity demonstrated by a significant decrease in cell viability in both YOU and PET cells (FIGS. 14 (B) and (C)).

Figure 15:
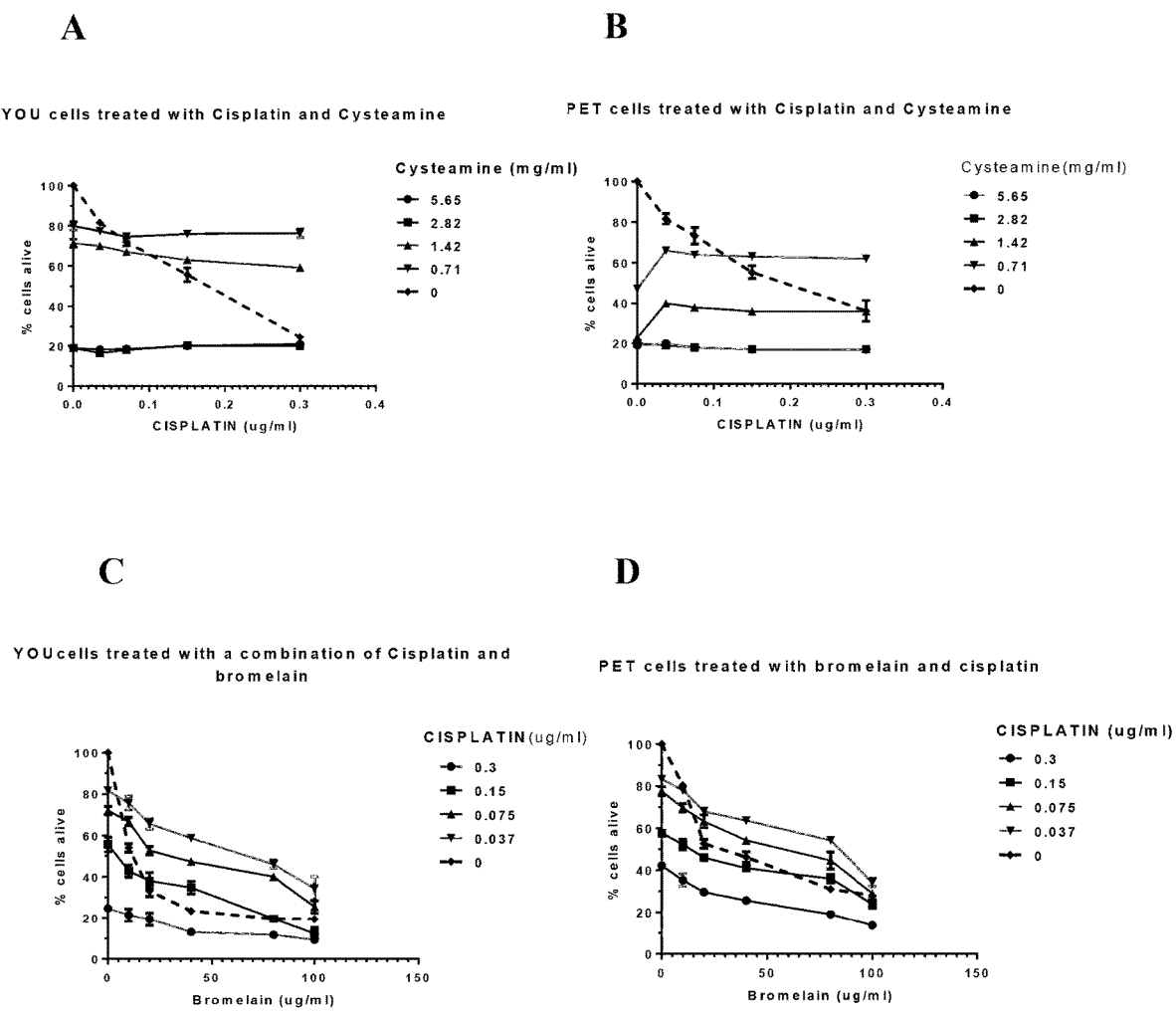
FIG. 15 shows the results of a viability assay demonstrating the combined effect of the combination of cisplatin and cysteamine on the in vitro growth of YOU and PET mesothelioma cells (A) and (B), respectively, and the combined effects of the combination of cisplatin and bromelain on the in vitro growth of YOU and PET mesothelioma cells, (C) and (D), respectively.

In contrast, no synergistic effects were observed for the combination of cysteamine and cisplatin (FIGS. 15 A and B), or bromelain (FIGS. 15 C and D). Indeed, at lower doses of cysteamine, the effects of cisplatin were somewhat inhibited. However, the addition of bromelain enhanced the effects of cisplatin, especially for lower doses of cisplatin (FIGS. 15 C and D).

Figure 16:
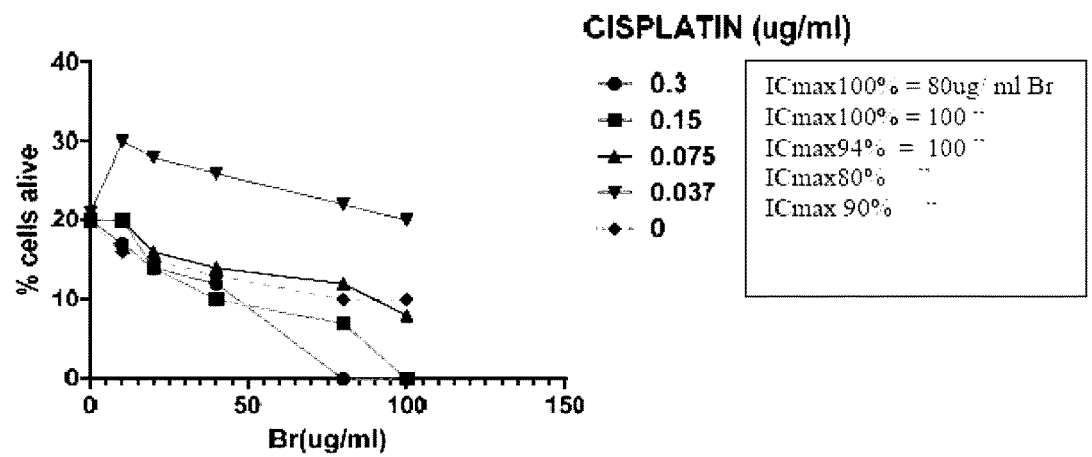
FIG. 16 shows the results of a viability assay demonstrating the combined effect of the combination of cisplatin, bromelain and cysteamine (5.65 mg/ml) on the in vitro growth of YOU and PET mesothelioma cells (A) and (B), respectively.
Figure 16:
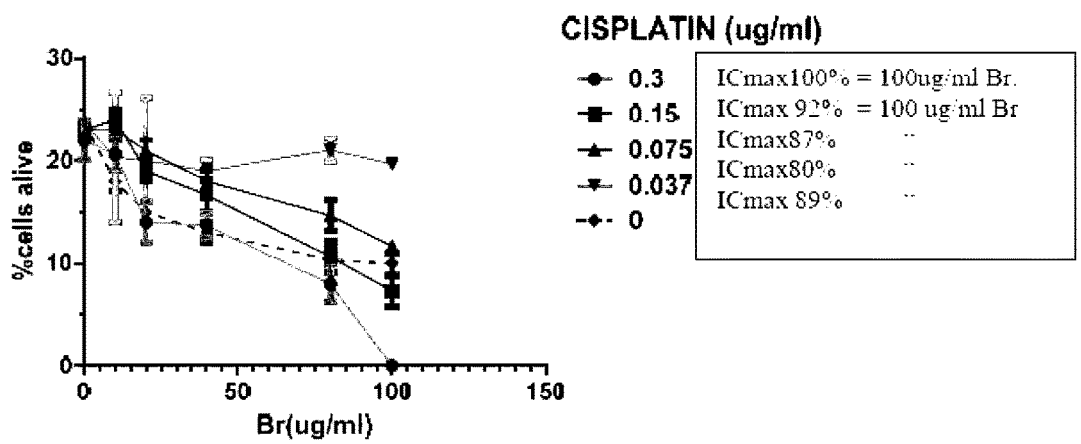
Figure 17:
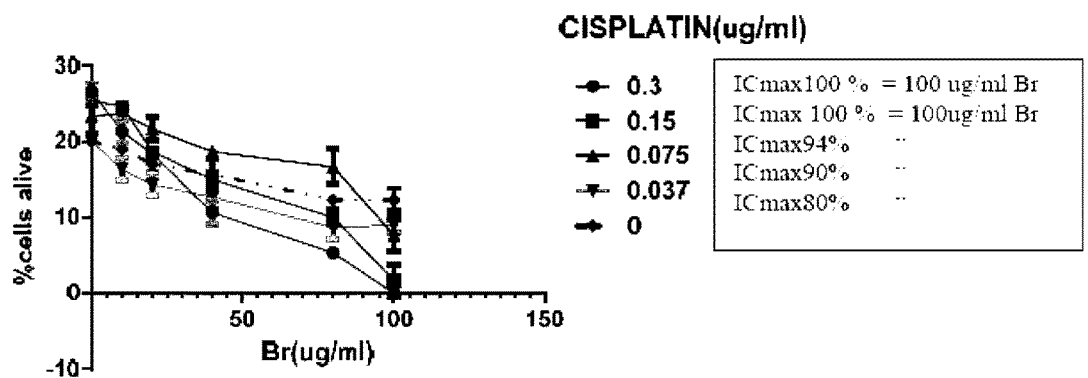
FIG. 17 shows the results of a viability assay demonstrating the combined effect of the combination of cisplatin, bromelain and cysteamine (2.82 mg/ml) on the in vitro growth of YOU and PET mesothelioma cells (A) and (B), respectively.
Figure 17:
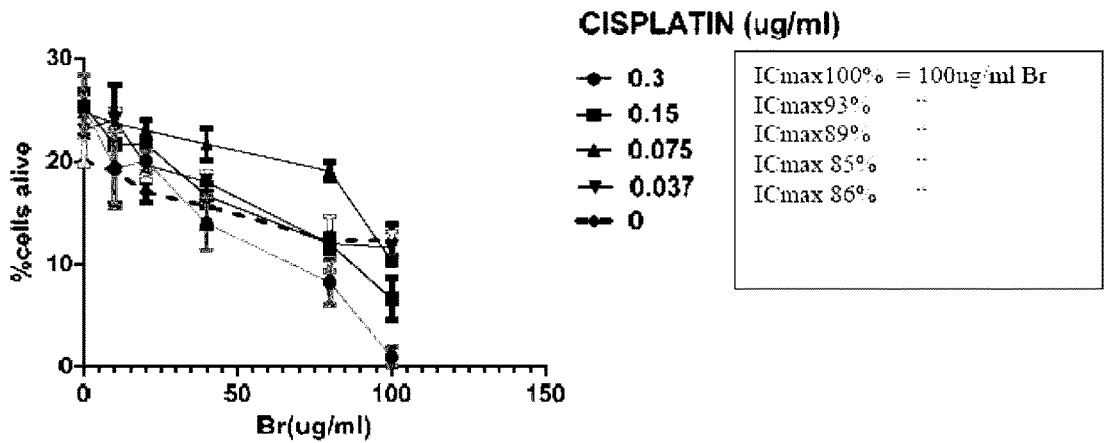
Figure 18:
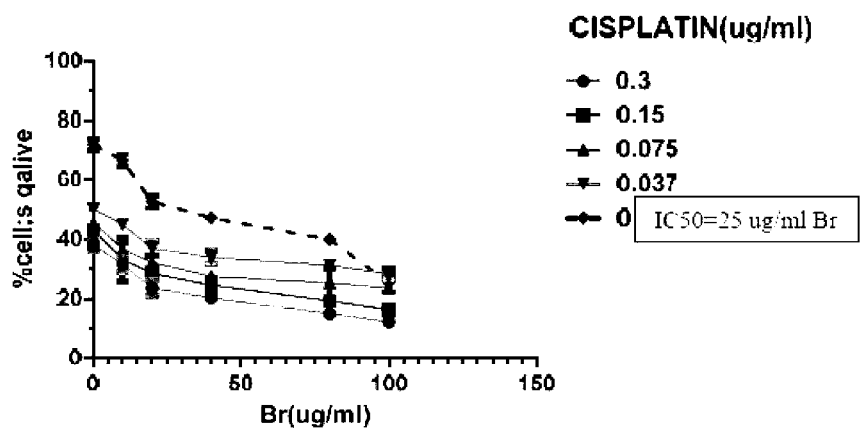
FIG. 18 shows the results of a viability assay demonstrating the combined effect of the combination of cisplatin, bromelain and cysteamine (1.42 mg/ml) on the in vitro growth of YOU and PET mesothelioma cells (A) and (B), respectively.
Figure 18:
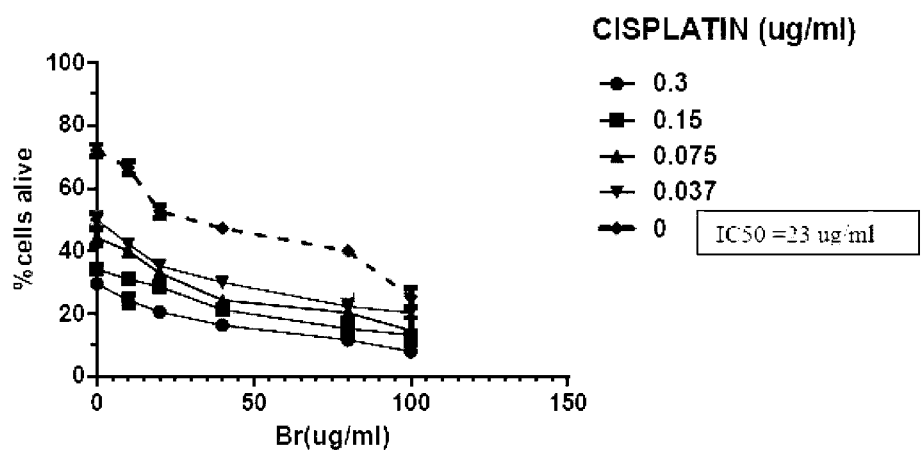

Whereas cells treated with a combination of bromelain (100 µg/ml) and the two highest doses of cisplatin (0.3, and 0.15 µg/ml) demonstrated decreased viability to levels of 10% and 12%, respectively, in YOU cells and 12% and 28%, respectively, in PET cells (FIGS. 15C and D, Table 1), the addition of cysteamine at concentrations of 5.65 mg/ml and 2.82 mg/ml, completely killed both YOU cells (FIG. 16 A and FIG. 17 A, respectively) and PET cells (FIGS. 16 B and 17 B, respectively). Indeed, YOU cells treated with 0.3 µg/ml cisplatin and 5.65 mg/ml cysteamine had zero viability when the dose of bromelain was reduced to 80 µg/ml (FIG. 16 A). The enhancement of cytoxocity was less pronounced when cells treated with a lower dose of cysteamine (1.42 mg/ml) (FIG. 18).

Using Chou and Tallarida Method (Tallarida R J. The interaction index: a measure of drug synergism. *Pain* 2002; 98: 163-168), the Interaction index (γ) was evaluated for a combination of 2 and 3 drugs (γ=1 (additive) (ADD); γ=<1 (synergistic) (SYN) and γ=>1 (sub-additive) (SUB)).

TABLE 12

Interaction index for bromelain, cysteamine and cisplatin in YOU and PET cell lines.

| Drug Combinations | YOU CELLS γ | | PET CELLS γ | |
|---|---|---|---|---|
| Bromelain + Cysteamine | 0.75 | SYN | 0.32 | SYN |
| Bromelain + Cisplatin | 1.23 | SUB | 0.96 | SYN |
| Cysteamine + Cisplatin | 4.0 | SUB | 4.1 | SUB |
| Bromelain + Cysteamine + Cisplatin | 1.0 | ADD | 1.0 | ADD |

Figure 19:
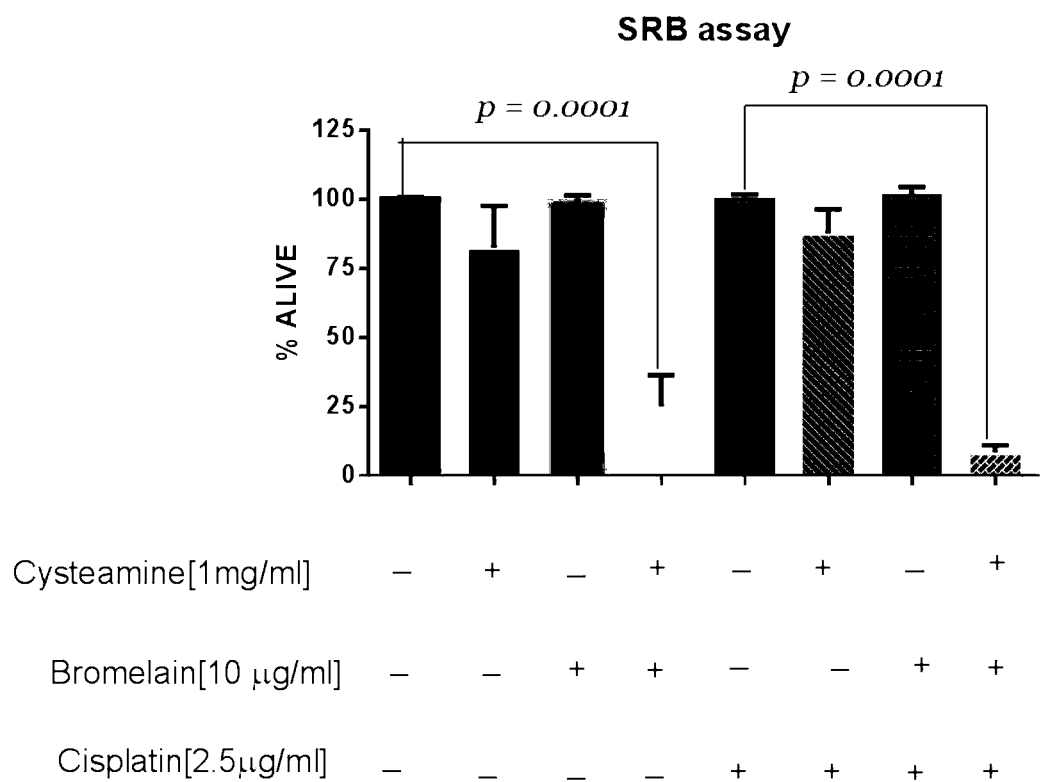
FIG. 19 shows the results of a viability assay demonstrating effect of Cysteamine+Bromelain+Cisplatin combination on the in vitro growth of human colorectal cancer line HT295M12.

FIG. 19 shows the effect of Cysteamine+Bromelain+Cisplatin, either alone or in combination on viability of human colorectal cancer cell line HT295M12 Cells were subjected to various treatment regimens as indicated for 3 days before SRB assays were performed. Data from two independent experiments are represented as mean±SD (6 replicates for each treatment group).

Statistical analysis for FIG. 19 is presented in Table 13, wherein columns from left to right correspond to columns A-H (e.g. Column A=control, Column B=Cysteamine 1 mg/ml, etc.).

TABLE 13

Statistical analysis for HT295M12 cells treated with bromelain, cysteamine and cisplatin:

| Holm-Sidak's multiple comparisons test | Mean Diff. | Significant? | Summary | Adjusted P Value |
|---|---|---|---|---|
| Column A vs. Column B | 9.610 | No | ns | 0.1572 |
| Column A vs. Column C | -3.042 | No | ns | 0.8192 |
| Column A vs. Column D | 49.61 | Yes | **** | <0.0001 |
| Column A vs. Column E | 1.241 | No | ns | 0.9371 |
| Column A vs. Column F | 10.29 | No | ns | 0.1144 |
| Column A vs. Column G | -6.949 | No | ns | 0.3898 |
| Column A vs. Column H | 88.30 | Yes | **** | <0.0001 |
| Column B vs. Column C | -12.65 | Yes | * | 0.0257 |
| Column B vs. Column D | 40.00 | Yes | **** | <0.0001 |
| Column B vs. Column E | -8.369 | No | ns | 0.2540 |
| Column B vs. Column F | 0.6795 | No | ns | 0.9371 |
| Column B vs. Column G | -16.56 | Yes | ** | 0.0016 |
| Column B vs. Column H | 78.69 | Yes | **** | <0.0001 |
| Column C vs. Column D | 52.65 | Yes | **** | <0.0001 |
| Column C vs. Column E | 4.282 | No | ns | 0.7971 |
| Column C vs. Column F | 13.33 | Yes | * | 0.0170 |
| Column C vs. Column G | -3.907 | No | ns | 0.7971 |
| Column C vs. Column H | 91.34 | Yes | **** | <0.0001 |
| Column D vs. Column E | -48.37 | Yes | **** | <0.0001 |
| Column D vs. Column F | -39.32 | Yes | **** | <0.0001 |
| Column D vs. Column G | -56.56 | Yes | **** | <0.0001 |
| Column D vs. Column H | 38.69 | Yes | **** | <0.0001 |
| Column E vs. Column F | 9.049 | No | ns | 0.1964 |
| Column E vs. Column G | -8.189 | No | ns | 0.2540 |
| Column E vs. Column H | 87.06 | Yes | **** | <0.0001 |
| Column F vs. Column G | -17.24 | Yes | *** | 0.0010 |
| Column F vs. Column H | 78.01 | Yes | **** | <0.0001 |
| Column G vs. Column H | 95.25 | Yes | **** | <0.0001 |

Figure 20:
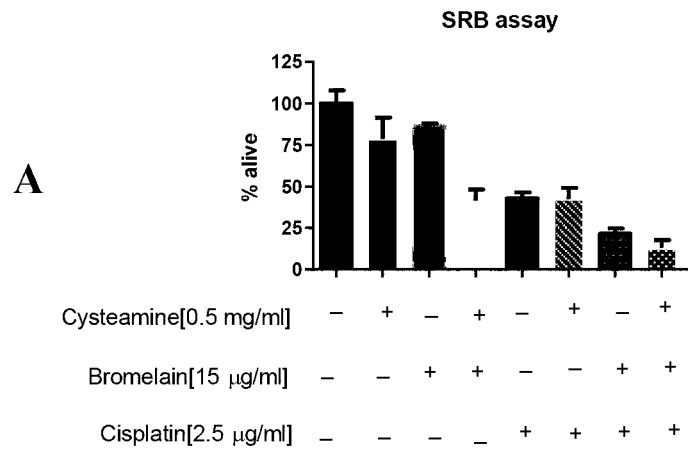
FIG. 20 shows the results of a viability assay demonstrating effect of Cysteamine+Bromelain+Cisplatin combination on the in vitro growth of human gastric cancer cell line KATO-III.
Figure 20:
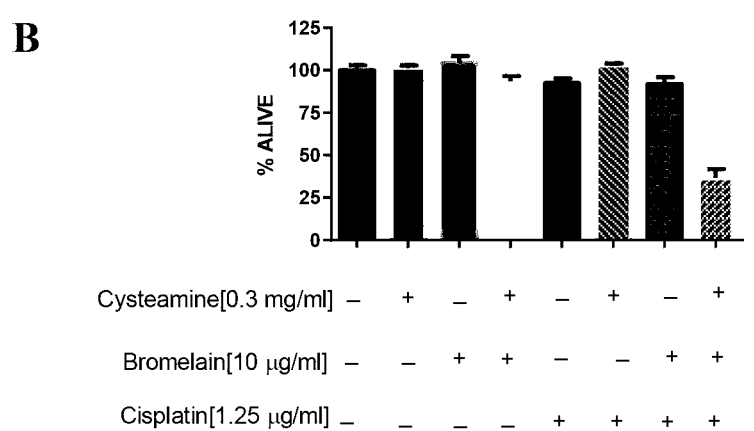
Figure 20:
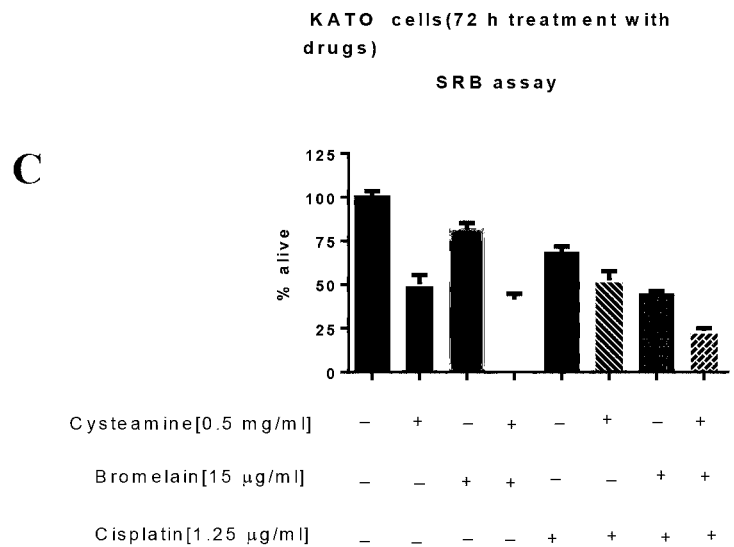

FIG. 20 shows the results of a viability assay demonstrating effect of Cysteamine+Bromelain+Cisplatin combination on the in vitro growth of human gastric cancer cell line KATO-HI. Cells were subjected to various treatment regimens as indicated for 3 days before SRB assays were performed. Data are represented as mean±SD (6 replicates for each treatment group).

Statistical analysis for FIGS. 20 A, B and C is presented in Table 14A, 14B and 14C, respectively, wherein columns from left to right correspond to A-H. (e.g. Column A=control, Column B=Cysteamine only, etc.).

TABLE 14A

Statistical analysis for KATO-III (Cysteamine 0.5 mg/ml + Bromelain 15 μg/ml + Cisplatin 2.5 μg/ml):

| Holm-Sidak's multiple comparisons test | Mean Diff. | Significant? | Summary | Adjusted P Value |
|---|---|---|---|---|
| Column A vs. Column B | 21.10 | Yes | **** | <0.0001 |
| Column A vs. Column C | 13.41 | Yes | ** | 0.0091 |
| Column A vs. Column D | 58.74 | Yes | **** | <0.0001 |
| Column A vs. Column E | 56.89 | Yes | **** | <0.0001 |
| Column A vs. Column F | 57.62 | Yes | **** | <0.0001 |
| Column A vs. Column G | 78.45 | Yes | **** | <0.0001 |
| Column A vs. Column H | 86.85 | Yes | **** | <0.0001 |
| Column B vs. Column C | −7.687 | No | ns | 0.2211 |
| Column B vs. Column D | 37.64 | Yes | **** | <0.0001 |
| Column B vs. Column E | 35.79 | Yes | **** | <0.0001 |
| Column B vs. Column F | 36.52 | Yes | **** | <0.0001 |
| Column B vs. Column G | 57.35 | Yes | **** | <0.0001 |
| Column B vs. Column H | 65.75 | Yes | **** | <0.0001 |
| Column C vs. Column D | 45.33 | Yes | **** | <0.0001 |
| Column C vs. Column E | 43.48 | Yes | **** | <0.0001 |
| Column C vs. Column F | 44.20 | Yes | **** | <0.0001 |
| Column C vs. Column G | 65.04 | Yes | **** | <0.0001 |
| Column C vs. Column H | 73.43 | Yes | **** | <0.0001 |
| Column D vs. Column E | −1.851 | No | ns | 0.9536 |
| Column D vs. Column F | −1.123 | No | ns | 0.9536 |
| Column D vs. Column G | 19.71 | Yes | **** | <0.0001 |
| Column D vs. Column H | 28.11 | Yes | **** | <0.0001 |
| Column E vs. Column F | 0.7277 | No | ns | 0.9536 |
| Column E vs. Column G | 21.56 | Yes | **** | <0.0001 |
| Column E vs. Column H | 29.96 | Yes | **** | <0.0001 |
| Column F vs. Column G | 20.83 | Yes | **** | <0.0001 |
| Column F vs. Column H | 29.23 | Yes | **** | <0.0001 |
| Column G vs. Column H | 8.397 | No | ns | 0.2211 |

TABLE 14B

Statistical analysis for KATO-III (Cysteamine 0.3 mg/ml + Bromelain 10 μg/ml + Cisplatin 1.25 μg/ml):

| Holm-Sidak's multiple comparisons test | Mean Diff. | Significant? | Summary | Adjusted P Value |
|---|---|---|---|---|
| Column A vs. Column B | −1.313 | No | ns | 0.9568 |
| Column A vs. Column C | −4.440 | No | ns | 0.2086 |
| Column A vs. Column D | 6.629 | Yes | * | 0.0129 |
| Column A vs. Column E | 7.406 | Yes | ** | 0.0044 |
| Column A vs. Column F | −2.917 | No | ns | 0.6398 |
| Column A vs. Column G | 7.930 | Yes | ** | 0.0022 |
| Column A vs. Column H | 63.39 | Yes | **** | <0.0001 |
| Column B vs. Column C | −3.127 | No | ns | 0.6082 |
| Column B vs. Column D | 7.943 | Yes | ** | 0.0022 |
| Column B vs. Column E | 8.720 | Yes | *** | 0.0007 |
| Column B vs. Column F | −1.603 | No | ns | 0.9568 |
| Column B vs. Column G | 9.244 | Yes | *** | 0.0003 |
| Column B vs. Column H | 64.70 | Yes | **** | <0.0001 |
| Column C vs. Column D | 11.07 | Yes | **** | <0.0001 |
| Column C vs. Column E | 11.85 | Yes | **** | <0.0001 |
| Column C vs. Column F | 1.523 | No | ns | 0.9568 |
| Column C vs. Column G | 12.37 | Yes | **** | <0.0001 |
| Column C vs. Column H | 67.83 | Yes | **** | <0.0001 |
| Column D vs. Column E | 0.7770 | No | ns | 0.9568 |
| Column D vs. Column F | −9.546 | Yes | *** | 0.0002 |
| Column D vs. Column G | 1.301 | No | ns | 0.9568 |
| Column D vs. Column H | 56.76 | Yes | **** | <0.0001 |
| Column E vs. Column F | −10.32 | Yes | **** | <0.0001 |
| Column E vs. Column G | 0.5242 | No | ns | 0.9568 |
| Column E vs. Column H | 55.98 | Yes | **** | <0.0001 |
| Column F vs. Column G | 10.85 | Yes | **** | <0.0001 |
| Column F vs. Column H | 66.30 | Yes | **** | <0.0001 |
| Column G vs. Column H | 55.46 | Yes | **** | <0.0001 |

TABLE 14C

Statistical analysis for KATO-III (Cysteamine 0.5 mg/ml + Bromelain 15 μg/ml + Cisplatin 1.25 μg/ml):

| Holm-Sidak's multiple comparisons test | Mean Diff. | Significant? | Summary | Adjusted P Value |
|---|---|---|---|---|
| Column A vs. Column B | 49.64 | Yes | **** | <0.0001 |
| Column A vs. Column C | 18.61 | Yes | **** | <0.0001 |
| Column A vs. Column D | 58.41 | Yes | **** | <0.0001 |
| Column A vs. Column E | 32.36 | Yes | **** | <0.0001 |
| Column A vs. Column F | 47.32 | Yes | **** | <0.0001 |
| Column A vs. Column G | 56.20 | Yes | **** | <0.0001 |
| Column A vs. Column H | 76.43 | Yes | **** | <0.0001 |
| Column B vs. Column C | −31.03 | Yes | **** | <0.0001 |
| Column B vs. Column D | 8.766 | Yes | ** | 0.0013 |
| Column B vs. Column E | −17.28 | Yes | **** | <0.0001 |
| Column B vs. Column F | −2.316 | No | ns | 0.5144 |
| Column B vs. Column G | 6.559 | Yes | * | 0.0156 |
| Column B vs. Column H | 26.79 | Yes | **** | <0.0001 |
| Column C vs. Column D | 39.80 | Yes | **** | <0.0001 |
| Column C vs. Column E | 13.75 | Yes | **** | <0.0001 |
| Column C vs. Column F | 28.72 | Yes | **** | <0.0001 |
| Column C vs. Column G | 37.59 | Yes | **** | <0.0001 |
| Column C vs. Column H | 57.82 | Yes | **** | <0.0001 |
| Column D vs. Column E | −26.05 | Yes | **** | <0.0001 |
| Column D vs. Column F | −11.08 | Yes | **** | <0.0001 |
| Column D vs. Column G | −2.207 | No | ns | 0.5144 |
| Column D vs. Column H | 18.02 | Yes | **** | <0.0001 |
| Column E vs. Column F | 14.97 | Yes | **** | <0.0001 |
| Column E vs. Column G | 23.84 | Yes | **** | <0.0001 |
| Column E vs. Column H | 44.08 | Yes | **** | <0.0001 |
| Column F vs. Column G | 8.875 | Yes | ** | 0.0013 |
| Column F vs. Column H | 29.11 | Yes | **** | <0.0001 |
| Column G vs. Column H | 20.23 | Yes | **** | <0.0001 |

Figure 21:
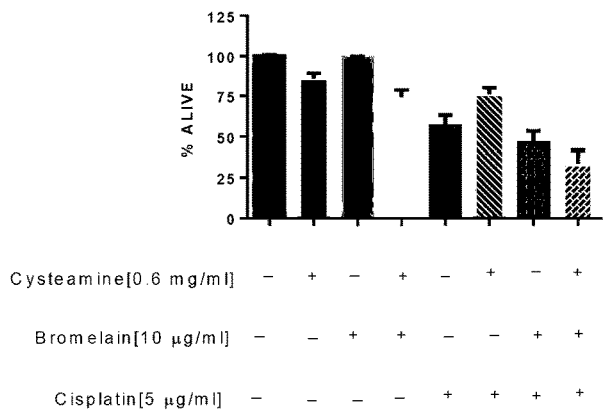
FIG. 21 shows the results of a viability assay demonstrating effect of Cysteamine+Bromelain+Cisplatin combination on the in vitro growth of human colorectal adenocarcinoma cell line LS174T.
Figure 21:
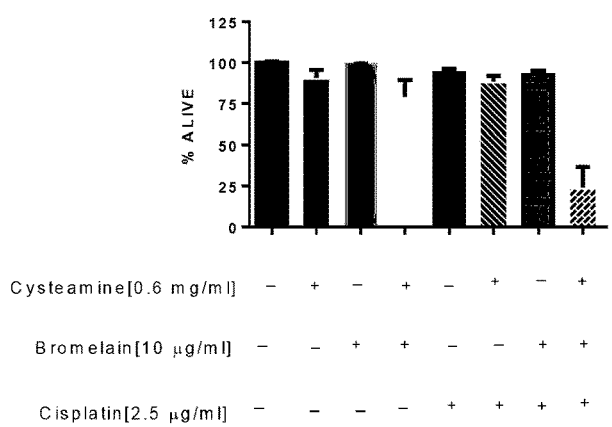
Figure 21:
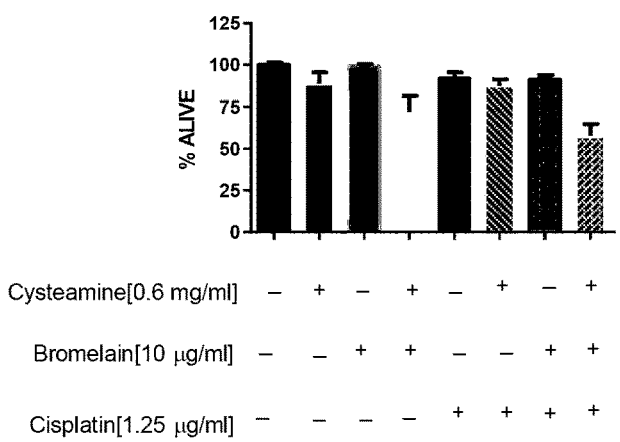

FIG. 21 shows the results of a viability assay demonstrating effect of Cysteamine+Bromelain+Cisplatin combination on the in vitro growth of human colorectal adenocarcinoma cell line LS174T. Cells were subjected to various treatment regimens as indicated for 3 days before SRB assays were performed. Data are represented as mean±SD (6 replicates for each treatment group).

Statistical analysis for FIGS. 21 A, B and C is presented in Table 15A 15B and 15C, respectively, wherein columns from left to right correspond to A-H. (e.g. Column A=control, Column B=Bromelain 5 μg/ml, etc.).

TABLE 15A

Statistical analysis for LS174T cells (Cysteamine 0.6 mg/ml + Bromelain 10 μg/ml + Cisplatin 5 μg/ml):

| Holm-Sidak's multiple comparisons test | Mean Diff. | Significant? | Summary | Adjusted P Value |
|---|---|---|---|---|
| Column A vs. Column B | 13.49 | Yes | *** | 0.0005 |
| Column A vs. Column C | 0.7455 | No | ns | 0.8055 |
| Column A vs. Column D | 25.50 | Yes | **** | <0.0001 |
| Column A vs. Column E | 43.30 | Yes | **** | <0.0001 |
| Column A vs. Column F | 23.51 | Yes | **** | <0.0001 |
| Column A vs. Column G | 53.70 | Yes | **** | <0.0001 |
| Column A vs. Column H | 66.36 | Yes | **** | <0.0001 |
| Column B vs. Column C | −12.75 | Yes | *** | 0.0009 |
| Column B vs. Column D | 12.00 | Yes | ** | 0.0014 |
| Column B vs. Column E | 29.81 | Yes | **** | <0.0001 |
| Column B vs. Column F | 10.01 | Yes | ** | 0.0056 |
| Column B vs. Column G | 40.21 | Yes | **** | <0.0001 |
| Column B vs. Column H | 52.87 | Yes | **** | <0.0001 |
| Column C vs. Column D | 24.75 | Yes | **** | <0.0001 |
| Column C vs. Column E | 42.56 | Yes | **** | <0.0001 |
| Column C vs. Column F | 22.76 | Yes | **** | <0.0001 |
| Column C vs. Column G | 52.96 | Yes | **** | <0.0001 |
| Column C vs. Column H | 65.62 | Yes | **** | <0.0001 |
| Column D vs. Column E | 17.81 | Yes | **** | <0.0001 |
| Column D vs. Column F | −1.988 | No | ns | 0.7623 |
| Column D vs. Column G | 28.21 | Yes | **** | <0.0001 |

TABLE 15A-continued

Statistical analysis for LS174T cells (Cysteamine 0.6 mg/ml + Bromelain 10 μg/ml + Cisplatin 5 μg/ml):

| Holm-Sidak's multiple comparisons test | Mean Diff. | Significant? | Summary | Adjusted P Value |
|---|---|---|---|---|
| Column D vs. Column H | 40.87 | Yes | **** | <0.0001 |
| Column E vs. Column F | −19.80 | Yes | **** | <0.0001 |
| Column E vs. Column G | 10.40 | Yes | ** | 0.0052 |
| Column E vs. Column H | 23.06 | Yes | **** | <0.0001 |
| Column F vs. Column G | 30.20 | Yes | **** | <0.0001 |
| Column F vs. Column H | 42.86 | Yes | **** | <0.0001 |
| Column G vs. Column H | 12.66 | Yes | *** | 0.0009 |

TABLE 15B

Statistical analysis for LS174T cells (Cysteamine 0.6 mg/ml + Bromelain 10 μg/ml + Cisplatin 2.5 μg/ml):

| Holm-Sidak's multiple comparisons test | Mean Diff. | Significant? | Summary | Adjusted P Value |
|---|---|---|---|---|
| Column A vs. Column B | 9.039 | No | ns | 0.1995 |
| Column A vs. Column C | 1.423 | No | ns | 0.9479 |
| Column A vs. Column D | 21.01 | Yes | **** | <0.0001 |
| Column A vs. Column E | 6.189 | No | ns | 0.6348 |
| Column A vs. Column F | 11.38 | Yes | * | 0.0499 |
| Column A vs. Column G | 7.260 | No | ns | 0.4456 |
| Column A vs. Column H | 75.96 | Yes | **** | <0.0001 |
| Column B vs. Column C | −7.616 | No | ns | 0.4036 |
| Column B vs. Column D | 11.97 | Yes | * | 0.0341 |
| Column B vs. Column E | −2.851 | No | ns | 0.9433 |
| Column B vs. Column F | 2.343 | No | ns | 0.9479 |
| Column B vs. Column G | −1.780 | No | ns | 0.9479 |
| Column B vs. Column H | 66.92 | Yes | **** | <0.0001 |
| Column C vs. Column D | 19.59 | Yes | **** | <0.0001 |
| Column C vs. Column E | 4.766 | No | ns | 0.7837 |
| Column C vs. Column F | 9.959 | No | ns | 0.1271 |
| Column C vs. Column G | 5.837 | No | ns | 0.6688 |
| Column C vs. Column H | 74.54 | Yes | **** | <0.0001 |
| Column D vs. Column E | −14.82 | Yes | ** | 0.0039 |
| Column D vs. Column F | −9.629 | No | ns | 0.1478 |
| Column D vs. Column G | −13.75 | Yes | ** | 0.0089 |
| Column D vs. Column H | 54.95 | Yes | **** | <0.0001 |
| Column E vs. Column F | 5.193 | No | ns | 0.7523 |
| Column E vs. Column G | 1.071 | No | ns | 0.9479 |
| Column E vs. Column H | 69.77 | Yes | **** | <0.0001 |
| Column F vs. Column G | −4.122 | No | ns | 0.8393 |
| Column F vs. Column H | 64.58 | Yes | **** | <0.0001 |
| Column G vs. Column H | 68.70 | Yes | **** | <0.0001 |

TABLE 15C

Statistical analysis for LS174T cells (Cysteamine 0.6 mg/ml + Bromelain 10 μg/ml + Cisplatin 1.25 μg/ml):

| Holm-Sidak's multiple comparisons test | Mean Diff. | Significant? | Summary | Adjusted P Value |
|---|---|---|---|---|
| Column A vs. Column B | 11.21 | Yes | ** | 0.0081 |
| Column A vs. Column C | 0.7502 | No | ns | 0.9726 |
| Column A vs. Column D | 27.87 | Yes | **** | <0.0001 |
| Column A vs. Column E | 7.962 | No | ns | 0.1119 |
| Column A vs. Column F | 12.39 | Yes | ** | 0.0029 |
| Column A vs. Column G | 8.717 | No | ns | 0.0665 |
| Column A vs. Column H | 42.22 | Yes | **** | <0.0001 |
| Column B vs. Column C | −10.46 | Yes | * | 0.0152 |
| Column B vs. Column D | 16.65 | Yes | **** | <0.0001 |
| Column B vs. Column E | −3.252 | No | ns | 0.8168 |
| Column B vs. Column F | 1.177 | No | ns | 0.9726 |
| Column B vs. Column G | −2.497 | No | ns | 0.8813 |
| Column B vs. Column H | 31.00 | Yes | **** | <0.0001 |
| Column C vs. Column D | 27.12 | Yes | **** | <0.0001 |
| Column C vs. Column E | 7.211 | No | ns | 0.1611 |
| Column C vs. Column F | 11.64 | Yes | ** | 0.0057 |
| Column C vs. Column G | 7.967 | No | ns | 0.1119 |
| Column C vs. Column H | 41.47 | Yes | **** | <0.0001 |
| Column D vs. Column E | −19.90 | Yes | **** | <0.0001 |
| Column D vs. Column F | −15.47 | Yes | *** | 0.0001 |
| Column D vs. Column G | −19.15 | Yes | **** | <0.0001 |
| Column D vs. Column H | 14.35 | Yes | *** | 0.0004 |
| Column E vs. Column F | 4.429 | No | ns | 0.6798 |
| Column E vs. Column G | 0.7552 | No | ns | 0.9726 |
| Column E vs. Column H | 34.25 | Yes | **** | <0.0001 |
| Column F vs. Column G | −3.674 | No | ns | 0.7928 |
| Column F vs. Column H | 29.83 | Yes | **** | <0.0001 |
| Column G vs. Column H | 33.50 | Yes | **** | <0.0001 |

FIGS. 25 to 29 show the results of a viability assay demonstrating effect of Cysteamine+Bromelain+Cisplatin, either alone or in various combinations, on the in vitro growth of human pancreatic cell line ASPC-1.

Pancreatic cancer cells ASPC1 (5000 cells/well) was seeded into a 96 well plate and treated with varying concentrations of bromelain, cysteamine, cisplatin and in combinations that was dissolved in culture media (RPMI). After 72 hours, the cells were fixed following standard procedures and stained using sulforhodamine dye and read at 570 nm.

As outlined above, drug interaction was carried out using Chou and Tallarida Method, the Interaction index (γ) was evaluated for a combination of 2 and 3 drugs.

TABLE 16 shows the IC50 concentration of Bromelain at various doses of Cysteamine.

| Cysteamine (mM) | IC50 (μg/ml Bromelain) |
|---|---|
| 0 | 25 |
| 0.6 | 22 |
| 1.25 | 19 |
| 2.5 | 17 |
| 5.0 | — |

TABLE 17 shows the LD50 concentration of Bromelain at various doses of Cisplatin.

| Cisplatin (μg/ml) | IC50 (μg/ml Bromelain) |
|---|---|
| 0 | 25 |
| 0.6 | 18 |
| 1.25 | 15 |
| 2.5 | 12 |
| 5.0 | — |

TABLE 18 shows a determination the interaction index of combinations of Cysteamine, Bromelain and Cisplatin in ASPC-1 cells.

| Drug Combination | Interaction index (γ) | Interpretation |
|---|---|---|
| Bromelain with cysteamine | | |
| Bromelain with 0.6 mM | 1.0 | Additive |
| Bromelain with 1.25 mM | 1.19 | Sub-additive |
| Bromelain with 2.5 mM | 1.84 | Sub-additive |
| Bromelain with Cisplatin | | |
| Bromelain with 0.6 µg/ml | 0.9 | Synergistic |
| Bromelain with 1.25 µg/ml | 1.0 | additive |
| Bromelain with 2.5 µg/ml | 1.38 | Sub-additive |
| Bromelain + Cysteamine + Cisplatin | | |
| Bromelain + Cysteamine + 0.6 µg/ml | 1.12 | Sub-additive |
| Bromelain + Cysteamine + 1.25 µg/ml | >2.0 | Sub-additive |
| Bromelain + Cysteamine + 2.5 µg/ml | >2.0 | Sub-additive |

Example 8. Comparison of the Antiproliferative Effect of Mucolytic Agents N-Acetyl Cysteine (NAC), Cysteamine, Cysteamine Dihydrochloride, L-Cysteine and L-Glutathione Reduced on Ovarian Cancer Cell Line A2780

Figure 22:
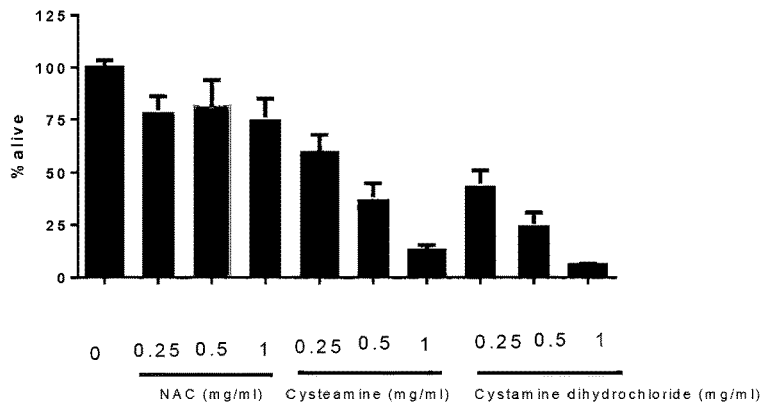
FIG. 22 shows a comparison of the effects of equal concentrations of: NAC, Cysteamine and Cysteamine dihydrochloride (A); NAC, Cysteamine and L-Cysteine (B) and NAC, Cysteamine and L-Glutathione reduced (C) on the viability of human ovarian cancer cell line A2780.
Figure 22:
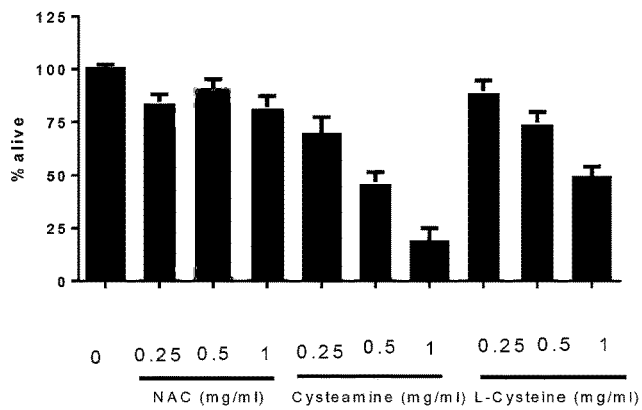
Figure 22:
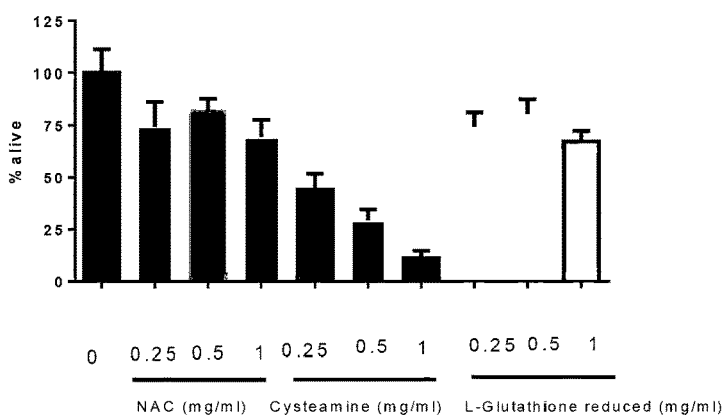

FIG. 22 shows the comparison of the effect of NAC, Cysteamine and Cysteamine dihydrochloride (A), L-Cysteine (B), and L-Glutathione reduced (C) on viability of human ovarian cancer cell line A2780. Cells were subjected to various treatment regimens as indicated for 3 days before SRB assays were performed. Data are represented as mean±SD (6 replicates for each treatment group).

Statistical analysis for FIGS. 22 A, B and C is presented in Table 19A, 19B and 19C, respectively, wherein columns from left to right correspond to A-J. (e.g. Column A=control, Column B=NAC 0.25 mg/ml, etc.).

TABLE 19A

Statistical analysis for A2780 cells treated with N-acetyl Cysteine (NAC), Cysteamine or Cysteamine dihydrochloride (0.25-1 mg/ml).

| Holm-Sidak's multiple comparisons test | Mean Diff. | Significant? | Summary | Adjusted P Value |
|---|---|---|---|---|
| Column A vs. Column B | 20.45 | Yes | **** | <0.0001 |
| Column A vs. Column C | 18.80 | Yes | *** | 0.0002 |
| Column A vs. Column D | 23.92 | Yes | **** | <0.0001 |
| Column A vs. Column E | 40.75 | Yes | **** | <0.0001 |
| Column A vs. Column F | 61.62 | Yes | **** | <0.0001 |
| Column A vs. Column G | 87.12 | Yes | **** | <0.0001 |
| Column A vs. Column H | 55.20 | Yes | **** | <0.0001 |
| Column A vs. Column I | 74.31 | Yes | **** | <0.0001 |
| Column A vs. Column J | 94.04 | Yes | **** | <0.0001 |
| Column B vs. Column C | −1.647 | No | ns | 0.6837 |
| Column B vs. Column D | 3.476 | No | ns | 0.6294 |
| Column B vs. Column E | 20.30 | Yes | **** | <0.0001 |
| Column B vs. Column F | 41.17 | Yes | **** | <0.0001 |
| Column B vs. Column G | 66.67 | Yes | **** | <0.0001 |
| Column B vs. Column H | 34.75 | Yes | **** | <0.0001 |
| Column B vs. Column I | 53.86 | Yes | **** | <0.0001 |
| Column B vs. Column J | 73.59 | Yes | **** | <0.0001 |
| Column C vs. Column D | 5.123 | No | ns | 0.5038 |
| Column C vs. Column E | 21.95 | Yes | **** | <0.0001 |
| Column C vs. Column F | 42.82 | Yes | **** | <0.0001 |
| Column C vs. Column G | 68.32 | Yes | **** | <0.0001 |
| Column C vs. Column H | 36.40 | Yes | **** | <0.0001 |
| Column C vs. Column I | 55.61 | Yes | **** | <0.0001 |
| Column C vs. Column J | 75.24 | Yes | **** | <0.0001 |
| Column D vs. Column E | 16.83 | Yes | ** | 0.0010 |
| Column D vs. Column F | 37.70 | Yes | **** | <0.0001 |
| Column D vs. Column G | 63.19 | Yes | **** | <0.0001 |
| Column D vs. Column H | 31.27 | Yes | **** | <0.0001 |
| Column D vs. Column I | 50.38 | Yes | **** | <0.0001 |
| Column D vs. Column J | 70.12 | Yes | **** | <0.0001 |
| Column E vs. Column F | 20.87 | Yes | **** | <0.0001 |
| Column E vs. Column G | 46.37 | Yes | **** | <0.0001 |
| Column E vs. Column H | 14.45 | Yes | ** | 0.0059 |
| Column E vs. Column I | 33.56 | Yes | **** | <0.0001 |
| Column E vs. Column J | 53.29 | Yes | **** | <0.0001 |
| Column F vs. Column G | 25.50 | Yes | **** | <0.0001 |
| Column F vs. Column H | −6.425 | No | ns | 0.3900 |
| Column F vs. Column I | 12.69 | Yes | * | 0.0172 |
| Column F vs. Column J | 32.42 | Yes | **** | <0.0001 |
| Column G vs. Column H | −31.92 | Yes | **** | <0.0001 |
| Column G vs. Column I | −12.81 | Yes | * | 0.0172 |
| Column G vs. Column J | 6.921 | No | ns | 0.3803 |
| Column H vs. Column I | 19.11 | Yes | *** | 0.0002 |
| Column H vs. Column J | 38.84 | Yes | **** | <0.0001 |
| Column I vs. Column J | 19.73 | Yes | *** | 0.0001 |

TABLE 19B

Statistical analysis for A2780 cells treated with N-acetyl Cysteine (NAC), Cysteamine or L-Cysteine (0.25-1 mg/ml).

| Holm-Sidak's multiple comparisons test | Mean Diff. | Significant? | Summary | Adjusted P Value |
|---|---|---|---|---|
| Column A vs. Column B | 15.35 | Yes | **** | <0.0001 |
| Column A vs. Column C | 9.290 | Yes | * | 0.0345 |
| Column A vs. Column D | 17.73 | Yes | **** | <0.0001 |
| Column A vs. Column E | 30.75 | Yes | **** | <0.0001 |
| Column A vs. Column F | 53.01 | Yes | **** | <0.0001 |
| Column A vs. Column G | 81.49 | Yes | **** | <0.0001 |
| Column A vs. Column H | 10.30 | Yes | * | 0.0160 |
| Column A vs. Column I | 25.30 | Yes | **** | <0.0001 |
| Column A vs. Column J | 51.11 | Yes | **** | <0.0001 |
| Column B vs. Column C | −6.062 | No | ns | 0.2689 |
| Column B vs. Column D | 2.380 | No | ns | 0.8401 |
| Column B vs. Column E | 15.40 | Yes | **** | <0.0001 |
| Column B vs. Column F | 37.66 | Yes | **** | <0.0001 |
| Column B vs. Column G | 66.14 | Yes | **** | <0.0001 |
| Column B vs. Column H | −5.050 | No | ns | 0.3491 |
| Column B vs. Column I | 9.952 | Yes | * | 0.0205 |
| Column B vs. Column J | 35.76 | Yes | **** | <0.0001 |
| Column C vs. Column D | 8.442 | No | ns | 0.0913 |
| Column C vs. Column E | 21.46 | Yes | **** | <0.0001 |
| Column C vs. Column F | 43.72 | Yes | **** | <0.0001 |
| Column C vs. Column G | 72.20 | Yes | **** | <0.0001 |
| Column C vs. Column H | 1.012 | No | ns | 0.8401 |
| Column C vs. Column I | 16.01 | Yes | **** | <0.0001 |
| Column C vs. Column J | 41.82 | Yes | **** | <0.0001 |
| Column D vs. Column E | 13.02 | Yes | ** | 0.0020 |
| Column D vs. Column F | 35.28 | Yes | **** | <0.0001 |
| Column D vs. Column G | 63.76 | Yes | **** | <0.0001 |
| Column D vs. Column H | −7.430 | No | ns | 0.1565 |
| Column D vs. Column I | 7.571 | No | ns | 0.1565 |
| Column D vs. Column J | 33.38 | Yes | **** | <0.0001 |
| Column E vs. Column F | 22.25 | Yes | **** | <0.0001 |
| Column E vs. Column G | 50.74 | Yes | **** | <0.0001 |
| Column E vs. Column H | −20.45 | Yes | **** | <0.0001 |
| Column E vs. Column I | −5.449 | No | ns | 0.3341 |
| Column E vs. Column J | 20.35 | Yes | **** | <0.0001 |
| Column F vs. Column G | 28.48 | Yes | **** | <0.0001 |
| Column F vs. Column H | −42.71 | Yes | **** | <0.0001 |
| Column F vs. Column I | −27.70 | Yes | **** | <0.0001 |
| Column F vs. Column J | −1.900 | No | ns | 0.8401 |
| Column G vs. Column H | −71.19 | Yes | **** | <0.0001 |
| Column G vs. Column I | −56.19 | Yes | **** | <0.0001 |
| Column G vs. Column J | −30.38 | Yes | **** | <0.0001 |

TABLE 19B-continued

Statistical analysis for A2780 cells treated with N-acetyl Cysteine (NAC), Cysteamine or L-Cysteine (0.25-1 mg/ml).

| Holm-Sidak's multiple comparisons test | Mean Diff. | Significant? | Summary | Adjusted P Value |
|---|---|---|---|---|
| Column H vs. Column I | 15.00 | Yes | *** | 0.0001 |
| Column H vs. Column J | 40.81 | Yes | **** | <0.0001 |
| Column I vs. Column J | 25.80 | Yes | **** | <0.0001 |

TABLE 19C

Statistical analysis for A2780 cells treated with N-acetyl Cysteine (NAC), Cysteamine or L-Glutathione (0.25-1 mg/ml).

| Holm-Sidak's multiple comparisons test | Mean Diff. | Significant? | Summary | Adjusted P Value |
|---|---|---|---|---|
| Column A vs. Column B | 25.62 | Yes | **** | <0.0001 |
| Column A vs. Column C | 18.03 | Yes | ** | 0.0030 |
| Column A vs. Column D | 30.51 | Yes | **** | <0.0001 |
| Column A vs. Column E | 55.93 | Yes | **** | <0.0001 |
| Column A vs. Column F | 70.70 | Yes | **** | <0.0001 |
| Column A vs. Column G | 88.77 | Yes | **** | <0.0001 |
| Column A vs. Column H | 25.68 | Yes | **** | <0.0001 |
| Column A vs. Column I | 19.54 | Yes | ** | 0.0011 |
| Column A vs. Column J | 32.71 | Yes | **** | <0.0001 |
| Column B vs. Column C | -7.592 | No | ns | 0.7087 |
| Column B vs. Column D | 4.890 | No | ns | 0.8290 |
| Column B vs. Column E | 30.31 | Yes | **** | <0.0001 |
| Column B vs. Column F | 45.08 | Yes | **** | <0.0001 |
| Column B vs. Column G | 63.15 | Yes | **** | <0.0001 |
| Column B vs. Column H | 0.05700 | No | ns | 0.9907 |
| Column B vs. Column I | -6.077 | No | ns | 0.7767 |
| Column B vs. Column J | 7.087 | No | ns | 0.7247 |
| Column C vs. Column D | 12.48 | No | ns | 0.0870 |
| Column C vs. Column E | 37.90 | Yes | **** | <0.0001 |
| Column C vs. Column F | 52.68 | Yes | **** | <0.0001 |
| Column C vs. Column G | 70.75 | Yes | **** | <0.0001 |
| Column C vs. Column H | 7.649 | No | ns | 0.7087 |
| Column C vs. Column I | 1.515 | No | ns | 0.9460 |
| Column C vs. Column J | 14.68 | Yes | * | 0.0260 |
| Column D vs. Column E | 25.42 | Yes | **** | <0.0001 |
| Column D vs. Column F | 40.19 | Yes | **** | <0.0001 |
| Column D vs. Column G | 58.26 | Yes | **** | <0.0001 |
| Column D vs. Column H | -4.833 | No | ns | 0.8290 |
| Column D vs. Column I | -10.97 | No | ns | 0.1842 |
| Column D vs. Column J | 2.197 | No | ns | 0.9460 |
| Column E vs. Column F | 14.77 | Yes | * | 0.0260 |
| Column E vs. Column G | 32.84 | Yes | **** | <0.0001 |
| Column E vs. Column H | -30.25 | Yes | **** | <0.0001 |
| Column E vs. Column I | -36.39 | Yes | **** | <0.0001 |
| Column E vs. Column J | -23.22 | Yes | **** | <0.0001 |
| Column F vs. Column G | 18.07 | Yes | ** | 0.0030 |
| Column F vs. Column H | -45.03 | Yes | **** | <0.0001 |
| Column F vs. Column I | -51.16 | Yes | **** | <0.0001 |
| Column F vs. Column J | -38.00 | Yes | **** | <0.0001 |
| Column G vs. Column H | -63.10 | Yes | **** | <0.0001 |
| Column G vs. Column I | -69.23 | Yes | **** | <0.0001 |
| Column G vs. Column J | -56.07 | Yes | **** | <0.0001 |
| Column H vs. Column I | -6.134 | No | ns | 0.7767 |
| Column H vs. Column J | 7.030 | No | ns | 0.7247 |
| Column I vs. Column J | 13.16 | No | ns | 0.0625 |

INCORPORATION BY CROSS-REFERENCE

The present invention claims priority from Australian provisional patent application number 2015904201 filed on 14 Oct. 2015 entitled "Compositions and methods for the treatment of diseases involving mucin", the entire contents of which is incorporated herein by cross-reference.

The invention claimed is:

1. A method for the treatment of a disease involving mucin, wherein the mucin is characterized as having a semi-hard or hard consistency, the method comprising administering a therapeutically effective amount of a synergistic mucolytic composition comprising (a) bromelain at a concentration of at least 50 µg/ml and (b) cysteamine or a pharmaceutically acceptable salt of cysteamine at a concentration of at least 50 mM, to a subject in need thereof, the synergistic mucolytic composition effective to synergistically disintegrate the semi-hard or hard consistency mucin.

2. The method according to claim 1, wherein the synergistic mucolytic composition further comprises at least one biologically active compound, or a metabolite, pharmaceutically acceptable salt, solvate or prodrug thereof.

3. The method according to claim 2, wherein the at least one biologically active compound is selected from any one of a mucolytic agent, N-glycosylation inhibitor, sialyltransferase inhibitor, multi-drug transport inhibitor, NSAID, antibiotic, anti-cancer agent and anti-inflammatory agent.

4. The method according to claim 3, wherein the at least one biologically active compound is an anti-cancer agent.

5. The method according claim 1, wherein the disease is cancer or pseudomyxoma peritonei.

6. The method according to claim 5, wherein the cancer is selected from lung cancer, breast cancer, colorectal cancer, thyroid cancer, prostate cancer, stomach cancer, pancreatic cancer, cancer of the appendix and ovarian cancer.

7. The composition according to claim 5, wherein the cancer is signet ring cell carcinoma.

8. The method according to claim 1, further comprising a step of removing mucinous material from the subject after a period of time following the administration of said composition.

9. The method according to claim 1, wherein the bromelain is at a concentration of from 50 µg/ml to 300 µg/ml.

10. The method of claim 9, wherein cysteamine or the pharmaceutically acceptable salt of cysteamine is at a concentration of from 50 mM to 200 mM.

11. The method of claim 1, wherein the cysteamine or the pharmaceutically acceptable salt of cysteamine is at a concentration of from 50 mM to 200 mM.

12. A method of disintegrating and/or solubilizing semi-hard or hard consistency mucinous material in a subject, comprising administering to the subject a therapeutically effective amount of a synergistic mucolytic composition comprising bromelain at a concentration of at least 50 µg/ml, and cysteamine or a pharmaceutically acceptable salt thereof at a concentration of at least 50 mM, the synergistic mucolytic composition effective to synergistically disintegrate the semi-hard or hard mucinous material.

13. The method of claim 12, wherein the subject suffers from cancer or pseudomyxoma peritonei.

* * * * *